United States Patent [19]

Chakraborty et al.

[11] Patent Number: 5,449,768
[45] Date of Patent: Sep. 12, 1995

[54] EIMERIA PRAECOX 16S RDNA PROBES

[75] Inventors: Prasanta R. Chakraborty, Scotch Plains; Michael Dashkevicz, Jamesburg; Alex Elbrecht, Watchung; Scott D. Feighner, Scotch Plains; Paul A. Liberator, Holmdel, all of N.J.; Helen Profous-Juchelka, Staten Island, N.Y.

[73] Assignee: Merck and Co., Inc., Rahway, N.J.

[21] Appl. No.: 879,594

[22] Filed: May 12, 1992

Related U.S. Application Data

[63] Continuation-in-part of Ser. No. 707,360, May 29, 1991, abandoned.

[51] Int. Cl.⁶ .................. C07H 21/04; C12Q 1/68; C12P 19/34
[52] U.S. Cl. .................. 536/24.32; 435/6; 935/787; 935/78
[58] Field of Search .......... 536/27, 23.1, 24.23, 536/24.33; 435/6, 91

[56] References Cited

U.S. PATENT DOCUMENTS

| | | | |
|---|---|---|---|
| 4,544,548 | 10/1985 | Davis et al. | 424/93 |
| 4,552,759 | 11/1985 | Davis et al. | 424/93 |
| 4,752,475 | 6/1988 | Davis et al. | 424/93 |
| 4,863,731 | 9/1989 | Davis et al. | 424/93 |

FOREIGN PATENT DOCUMENTS

| | | |
|---|---|---|
| 155360 | 9/1982 | European Pat. Off. |
| WO85/00752 | 8/1984 | WIPO . |

OTHER PUBLICATIONS

Hans et al., Biochemistry (1987), vol. 26, pp. 1617–1625.
Joyner & Long, Avian Path. 3:145–157, 1974.
Shirley, Research in Avian Coccidiosis, pp. 13–35, 1985.
Hasegawa et al., J. Mol. Evol. 22:32–38, 1985.
Johnson et al., Exp. Parasitol. 63:272–278, 1987.
Dame & McCutchan, J. Biol. Chem. 258:6984–6990, 1983.
Langsley et al., Nucleic Acids Res. 11:8703–8717, 1983.
Ellis & Blumstead, Parasitol. 101:1–6, 1990.
Johnson et al., System Parasitol. 18:1–8, 1991.
McCutchan et al., Mol. Biochem. Parasitol. 28:63–68, 1988.
Forsman et al., Appld. Environ. Microbiol. 56:949–955, 1990.
Dans et al., Nucleic Acid Res. 165:r87–r173, 1988.
Ferreira et al., Mol. Biochem. Parasitol. 19:103–109, 1986.350121
Arreaza et al., Exp. Parasitol. 72:103–105, 1991.
Saiki et al., Science 239:487–491, 1988.
Labarca & Paigen, Anal. Biochem. 102:344–352, 1980.
Johnston et al., Electrophoresis 11:355–360, 1990.
Jackson, Parasiotol 54:87–93, 1964.
Edgar, Trans. Am. Micro. Soc. 62:237–242, 1954.
Neefs et al., Nucleic Acids Res. 18S:2237–2317, 1990.
Clark, Nucleic Acids Res. 16:9677–9686, 1988.
Vogelstein & Gillespie, Proc. Natl. Acad. Sci. USA 76:615–619, 1979.
Sanger et al, J. Mol. Biol. 143:161–178, 1980.
Chen & Seeburg, DNA, 4:165–170, 1985.
Tabor & Richardson, Proc. Natl. Acad. Sci. USA 84:4767–4771, 1987.
Freier et al., Proc. Natl. Acad. Sci. USA 83:9373–9377, 1986.
Suggs et al., ICN-UCLA Symp. Dev. Biol. Using Purified Genes, 23:683–693, 1981.
Chirgwin et al., Biochemistry 18:5294–5299, 1979.

Primary Examiner—Margaret Moskowitz
Assistant Examiner—Lisa Bennett
Attorney, Agent, or Firm—Christine E. Carty; Jack L. Tribble; Hesna J. Pfeiffer

[57] ABSTRACT

Unique species-specific *Eimeria praecox* DNA probes comprising divergent DNA sequences are disclosed. The probes are complementary to a small subunit ribosomal RNA gene of *Eimeria praecox*.

2 Claims, 40 Drawing Sheets

```
  1  TAGTCATATG CTTGTCTCAA AGATTAAGCC ATGCATGTCT   40
 41  AAGTATAAGC TTTTATACGG TGAAACTGCG AATGGCTCAT   80
 81  TAAAACAGTT ATAGTTTATT TGATGGTCTC TTTTACATGG  120
121  ATAACCATGG TAATTCTATG CTAATACAT GCGCAAGGGC   160
161  CTCCTCCTCT GGAGGGGCTG TGTTTATTAG ATACAAAACC  200
201  AACCCACCTT GTGTGGAGTC TTGGTGATTC ATAGTAACCG  240
241  AACGGATCGC AGTTGGCTTT CGGGCCCGCG ATGGATCATT  280
281  CAAGTTTCTG ACCTATCAGC TTTCGACGGT AGGGTATTGG  320
321  CCTACCGTGG CAGTGACGGG TAACGGGGAA TTAGGGTTCG  360
361  ATTCCGGAGA GGGAGCCTGA GAAACGGCTA CCACATCTAA  400
401  GGAAGGCAGC AGGCGCGCAA ATTACCCAAT GAAAACAGTT  440
441  TCGAGGTAGT GACGAGAAAT AACAATACAG GGCATCTTAT  480
481  GCTTTGTAAT TGGAATGATG GAATGTAAA ACCCTTCCAG   520
521  AGTAACAATT GGAGGGCAAG TCTGGTGCCA GCAGCCGCGG  560
561  TAATTCCAGC TCCAATAGTG TATATTAGAG TTGTTGCAGT  600
601  TAAAAAGCTC GTAGTTGGAT TTCTGTCGTG GTCAGCCTGC  640
641  GCTGCCCGTA TGGGTGTGCG CGTGGTTTGC CCTCGGCTTT  680
681  TTTCTGGTAG CCTCCTGCGC TTAATTGCGT GGGCTGGTGT  720
721  TCCGGAACTT TTACTTTGAG AAAAATAGAG TGTTTCAAGC  760
761  AGGCTTGTCG CCCTGAATAC TGCAGCATGG AATAATAAGA  800
801  TAGGACCTCG GTTCTATTTT GTTGGTTTCT AGGACCAAGG  840
841  TAATGATTAA TAGGGACAGT TGGGGGCATT CGTATTTAAC  880
881  TGTCAGAGGT GAAATTCTTA GATTTGTTAA AGACGAACTA  920
921  CTGCGAAAGC ATTTGCCAAG GATGTTTTCA TTAATCAAGA  960
```

FIG.1A

```
 961  ACGACAGTAG GGGGTTTGAA GACGATTAGA TACCGTCGTA  1000
1001  ATCTCTACCA TAAACTATGC CGACTAGAGA TAGGGAAATG  1040
1041  CCTACCTTGG CTTCTCCTGC ACCTCATGAG AAATCAAAGT  1080
1081  CTCTGGGTTC TGGGGGGAGT ATGGTCGCAA GGCTGAAACT  1120
1121  TAAAGGAATT GACGGAGGGG CACCACCAGG CGTGGAGCCT  1160
1161  GCGGCTTAAT TTGACTCAAC ACGGGGAAAC TCACCAGGTC  1200
1201  CAGACATGGG AAGGATTGAC AGATTGATAG CTCTTTCTTG  1240
1241  ATTCTATGGG TGGTGGTGCA TGGCCGTTCT TAGTTGGTGG  1280
1281  AGTGATCTGT CTGGTTAATT TCGATAACGA ACGAGACCTT  1320
1321  GGCCTGCTAA ATAGGGTCGG TAACTTCGGT TATCGTATCA  1360
1361  CTTCTTAGAG GGACTTTGCG TGTCTAACGC AAGGAAGTTT  1400
1401  GAGGCAATAA CAGGTCTGTG ATGCCCTTAG ATGTTCTGGG  1440
1441  CTGCACGCGC GCTACACTGA TGCATGCAAC GAGTTTTTAC  1480
1481  CTTGACCGAC GGGGCTGGGT AATCTTCTGA GGGTGCATCG  1520
1521  TGATGGGGAT AGATTATTGC AATTATTAGT CTTCAACGAG  1560
1561  GAATGCCTAG TAGGCGCAAG TCAGCAGCTT GCGCCGATTA  1600
1601  CGTCCCTGCC TCTTGTACAC ACCGCCCGTC GCTGCAACCG  1640
1641  ATCGGAGGGT CCTGTGAATT CATCGGACTG GCCATTCTCA  1680
1681  CTTTGGGGCT GGCCGGGAAG TTGCGTAAAT AGAGCCCTCT  1720
1721  AAAGGATGCA AAAGTCGTAA CACGGTTT  1748
```

FIG.1B

| | | | | |
|---|---|---|---|---|
| TAGTCATATG | CTTGTCTCAA | AGATTAAGCC | ATGCATGTCT | 40 |
| AAGTATAAAC | TTTTATACGG | TGAAACTGCG | AATGGCTCAT | 80 |
| TAAAACAGTT | ATAGTTTATT | TGATGGTCAT | TTTTACATGG | 120 |
| ATAACCATGG | TAATTCTATG | GCTAATACAT | GCGCATAGGC | 160 |
| TTCCTTCTTT | GAAGGGGCTG | TGTTTATTAG | ATACAAAACC | 200 |
| AACCCACCTT | GTGGAGCCTT | GGTGATTCAT | AGTAACCGAA | 240 |
| CGGATCGCAG | TTGGCTTTCG | GCCCGCGAT | GGATCATTCA | 280 |
| AGTTTCTGAC | CTATCAGCTT | TCGACGGTAG | GGTATTGGCC | 320 |
| TACCGTGGCA | GTGACGGGTA | ACGGGAATT | AGGGTTCGAT | 360 |
| TCCGGAGAGG | GAGCCTGAGA | AACGGCTACC | ACATCTAAGG | 400 |
| AAGGCAGCAG | GCGCGCAAAT | TACCCAATGA | AACAGTTTC | 440 |
| GAGGTAGTGA | CGAGAAATAA | CAATACAGGG | CATTTAATGC | 480 |
| TTTGTAATTG | GAATGATGGG | AATGTAAAAC | CCTTCCAGAG | 520 |
| TAACAATTGG | AGGGCAAGTC | TGGTGCCAGC | AGCCGCGGTA | 560 |
| ATTCCAGCTC | CAATAGTGTA | TATTAGAGTT | GTTGCAGTTA | 600 |
| AAAAGCTCGT | AGTTGGATTT | CTGTCGTGGT | CAGCCTGCGC | 640 |
| TGCCCGTATG | GGTGTGCGCG | TGGTTTGCCC | GCGGCTTTCT | 680 |
| TCCGGTAGCC | TCCGGCTCTT | AATTGCGTCG | GTGGGTGTTC | 720 |
| TGGAACTTTT | ACTTTGAGAA | AAATAGAGTG | TTTCAAGCAG | 760 |
| GCTTGTCGCC | CTGAATACTG | CAGCATGGAA | TAATAAGATA | 800 |
| GGACCTCGGT | TCTATTTTGT | TGGTTTCTAG | GACCAAGGTA | 840 |
| ATGATTAATA | GGGACAGTTG | GGGGCATTCG | TATTTAACTG | 880 |
| TCAGAGGTGA | AATTCTTAGA | TTTGTTAAAG | ACGAACTACT | 920 |
| GCGAAAGCAT | TTGCCAAGGA | TGTTTTCATT | AATCAAGAAC | 960 |

FIG.2A

```
GACAGTAGGG GGTTTGAAGA CGATTAGATA CCGTCGTAAT    1000

CTCTACCATA AACTATGCCG ACTAGAGATA GGGAAATGCC    1040

TACCTTGGCT TCTCCTGCAC CTCATGAGAA ATCAAAGTCT    1080

CTGGGTTCTG GGGGAGTAT  GGTCGCAAGG CTGAAACTTA    1120

AAGGAATTGA CGGAGGGGCA CCACCAGGCG TGGAGCCTGC    1160

GGCTTAATTT GACTCAACAC GGGGAAACTC ACCAGGTCCA    1200

GACATGGGAA GGATTGACAG ATTGATAGCT CTTTCTTGAT    1240

TCTATGGGTG GTGGTGCATG GCCGTTCTTA GTTGGTGGAG    1280

TGATCTGTCT GGTTAATTTC GATAACGAAC GAGACCTTGG    1320

CCTGCTAAAT AGGGTCGGTG ACCTCGGTCA CGCATCGCTT    1360

CTTAGAGGGA CTTTGCGTGT CTAACGCAGG GAAGTTCGAG    1400

GCAATAACAG GTCTGTGATG CCCTTAGATG TTCTGGGCTG    1440

CACGCGCGCT ACACTGATGC ATGCAACGAG TTCTTACCTT    1480

GGCCGACGGG GCTGGGTAAT CTTGTGGGG  TGCATCGTGA    1520

TGGGATAGA  TTATTGCAAT TATTAGTCTT CAACGAGGAA    1560

TGCCTAGTAG GCGCAAGTCA GCAGCTTGCG CCGATTACGT    1600

CCCTGCCTCT TGTACACACC GCCCGTCGCT GCAACCGATG    1640

GAGGGTCCTG TAAATTCATC GGACTGGCCA ACCCCATTTT    1680

GGGGCTGGCT GGAAAGTTGC GTAAATAGAG CCCTCTAAAG    1720

GATGCAAAAG TCGTAACACG GTTT                    1744
```

FIG. 2B

```
  1  TAGTCATATG CTTGTCTCAA AGATTAAGCC ATGCATGTCT   40
 41  AAGTATAAAC TTTTATACGG TGAAACTGCG AATGGCTCAT   80
 81  TAAAACAGTT ATAGTTTATT TGATGGTCTT TTTTACATGG  120
121  ATAACCATGG TAATTCTATG CTAATACAT  GCGCAAAAGC  160
161  TACCTTCTTT GGAGGAGCTG TGTTTATTAG ATACAAAACC  200
201  AGCCCACAAT TCTTGTGGAG TCTTGGTGAT TCATAGTAAC  240
241  CGAACGGATC GCAGTTGGCT TTCGGGCCCG CGATGGATCA  280
281  TTCAAGTTTC TGACCTATCA GCTTCGACG  GTAGGGTATT  320
321  GGCCTACCGT GGCAGTGACG GGTAACGGGG AATTAGGGTT  360
361  CGATTCCGGA GAGGGAGCCT GAGAAACGGC TACCACATCT  400
401  AAGGAAGGCA GCAGGCGCGC AAATTACCCA ATGAAAACAG  440
441  TTTCGAGGTA GTGACGAGAA ATAACAATAC AGGGCATTTT  480
481  ATGCTTTGTA ATTGGAATGA TGGGAATGTA AAACCCTTCC  520
521  AGAGTAACAA TTGGAGGGCA AGTCTGGTGC CAGCAGCCGC  560
561  GGTAATTCCA GCTCCAATAG TGTATATTAG AGTTGTTGCA  600
601  GTTAAAAAGC TCGTAGTTGG ATTTCTGTCG TGGTCAGCTT  640
641  GCGCTGCCCG TATGGGTGTG CGCGTGGTTT GCCCTCGGCA  680
681  TTCTTCCGGT AGCTTGTGGC GCTTAATTGC GTCTGCAAGT  720
721  GCCCTGGAAC TTTTACTTTG AGAAAATAG  AGTGTTTCAA  760
761  GCAGGCTTGT CGCCCTGAAT ACTGCAGCAT GGAATAATAG  800
801  GATAGGACCT CGGTTCTATT TTGTTGGTTT CTAGGACCAA  840
841  GGTAATGATT AATAGGGACA GTTGGGGGCA TTCGTATTTA  880
881  ACTGTCAGAG GTGAAATTCT TAGATTTGTT AAAGACGAAC  920
921  TACTGCGAAA GCATTTGCCA AGGATGTTTT CATTAATCAA  960
```

FIG.3A

```
 961  GAACGACAGT AGGGGGTTTG AAGACGATTA GATACCGTCG  1000
1001  TAATCTCTAC CATAAACTAT GCCGACTAGA GATAGGAAAA  1040
1041  CGCCTCCCTT GGCTTCTCCT GGACCTCATG AGAAATCAAA  1080
1081  GTCTCTGGGT TCTGGGGGGA GTATGGTCGC AAGGCTGAAA  1120
1121  CTTAAAGGAA TTGACGGAGG GGCACCACCA GGCGTGGAGC  1160
1161  CTGCGGCTTA ATTTGACTCA ACACGGGGAA ACTCACCAGG  1200
1201  TCCAGACATG GGAAGGATTG ACAGATTGAT AGCTCTTTCC  1240
1241  TGATTCTATG GGTGGTGGTG CATGGCCGTT CTTAGTTGGT  1280
1281  GGAGTGATTT GTCTGGTTAA TTTCGATAAC GAACGAGACC  1320
1321  TTGGCCTGCT AAATAGGGTC GGTGACCTCG GTTACCGTAT  1360
1361  CACTTCTTAG AGGGACATTG CGTGTCTAAC GCAAGGAAGT  1400
1401  TTGAGGCAAT AACAGGTCTG TGATGCCCTT AGATGTTCTG  1440
1441  GGCTGCACGC GCGCTACACT GATGCATGCA ACGAGTTTTC  1480
1481  ACCTTGTCCG ATGGGCTGGG TAATCTTGT GAGGGTGCAT  1520
1521  CGTGATGGGG ATAGATTATT GCAATTATTA GTCTTCAACG  1560
1561  AGGAATGCCT AGTAGGCGCA AGTCAGCAGC TTGTGCCGAT  1600
1601  TACGTCCCTG CCTCTTGTAC ACACCGCCCG TCGCTGCAAC  1640
1641  CGATCGGAGG GTCCTGTAAA TTCATCGGAC TGACCAGCCC  1680
1681  CAACTTGGGG CTGGTCGGAA AGTTGCGTAA ATAGAGCCCT  1720
1721  CTAAAGGATG CAAAAGTCGT AACACGGTTT        1750
```

FIG.3B

```
  1  TAGTCATATG  CTTGTCTCAA  AGATTAAGCC  ATGCATGTCT   40
 41  AAGTATAAGC  TTTTATACGG  TGAAACTGCG  AATGGCTCAT   80
 81  TAAAACAGTT  ATAGTTTATT  TGATGGTCTT  TTTTACATGG  120
121  ATAACCATGG  TAATTCTATG  GCTAATACAT  GCGCATAGGC  160
161  CTCCTCCTCT  GGAGGGGCTG  TGTTTATTAG  CTACAAAACC  200
201  AACCCACTTT  TGTGGAGCCT  TGGTGATTCA  TAGTAACCGA  240
241  ACGGATCGCA  GTTGGCTTTC  GGGCCCGCGA  TGGATCATTC  280
281  AAGTTTCTGA  CCTATCAGCT  TTCGACGGTA  GGGTATTGGC  320
321  CTACCGTGGC  AGTGACGGGT  AACGGGGAAT  TAGGGTTCGA  360
361  TTCCGGAGAG  GGAGCCTGAG  AAACGGCTAC  CACATCTAAG  400
401  GAAGGCAGCA  GGCGCGCAAA  TTACCCAATG  AAAACAGTTT  440
441  CGAGGTAGTG  ACGAGAAATA  ACAATACAGG  GCATTTATG   480
481  CTTTGTAATT  GGAATGATGG  GAATGTAAAA  CCCTTCCAGA  520
521  GTAACAATTG  GAGGGCAAGT  CTGGTGCCAG  CAGCCGCGGT  560
561  AATTCCAGCT  CCAATAGTGT  ATATTAGAGT  TGTTGCAGTT  600
601  AAAAAGCTCG  TAGTTGGATT  TCTGTCGTGG  TCTTCCTGTG  640
641  CTGCCCGTAT  CGGTGCACGT  GGCTTGCCCT  CGACTTTCTT  680
681  CCGGTAGCCT  CCTGCGCTTC  ACTGCGTGGG  CTGGTGTTCT  720
721  GGAACTTTTA  CTTTGAGAAA  AATAGAGTGT  TCAAGCAGC   760
761  TTGTCGCCCT  GAATACTGCA  GCATGGAATA  ATAAGATAGG  800
801  ACCTCGGTTC  TATTTTGTTG  GTTTCTAGGA  CCAAGGTAAT  840
841  GATTAATAGG  GACAGTTGGG  GGCATTCGTA  TTTAACTGTC  880
881  AGAGGTGAAA  TTCTTAGATT  TGTTAAAGAC  GAACTACTGC  920
921  GAAAGTTTGC  CAAGGATGTT  TTCATTAATC  AAGAACGACA  960
```

FIG. 4A

```
 961  GTAGGGGGTT  TGAAGACGAT  TAGATACCGT  CGTAATCTCT  1000
1001  ACCATAAACT  ATGCCGACTA  GAGATAGGGA  AACGCCTACC  1040
1041  TTGGCTTCTC  CTGCACCTCA  TGAGAAATCA  AAGTCTCTGG  1080
1081  GTTCTGGGGG  GAGTATGGTC  GCAAGGCTGA  AACTTAAAGG  1120
1121  AATTGACGGA  GGGGCACCAC  CAGGCGTGGA  GCCGGGCCTT  1160
1161  AATTTGACTC  AACACGGGGA  AACTCACCAG  GTCCAGACAT  1200
1201  GGGAAGGATT  GACAGATTGA  TAGCTCTTTC  TTGATTCTAT  1240
1241  GGGTGGTGGT  GCATGGCCGT  TCTTAGTTGG  TGGAGTGATC  1280
1281  TGTCTGGTTA  ATTTCGATAA  CGAACGAGAC  CTTGGCCTGC  1320
1321  TAAATAGGGT  CGGTGACCCT  GGGTCACCAG  GTCACCGCAT  1360
1361  CGCTTCTTAG  AGGAACTTTG  CGTGTCTAAC  GCAAGGAAGT  1400
1401  TTGAGGCAAT  AACAGGTCTG  TGATGCCCTT  AGATGTTCTG  1440
1441  GGCTGCACGC  GCGCTACACT  GATGCATGCA  ACGAGTTTTT  1480
1481  ACCTTGCCCG  ATGGGCGTGG  GTAATCTTGT  GAGGGTGCAT  1520
1521  CGTGATGGGG  ATAGATTATT  GCAATTATTA  GTCTTCAACG  1560
1561  AGGAATGCCT  AGTAGGCGCA  AGTCAGCAGC  TTGCGCCGAC  1600
1601  TAAGTCCCTG  CCTCTTGTAC  ACACCGCCCG  TCGCTGCAAC  1640
1641  CGATCGGAGG  GTCCTGTGAA  TTCATCGGAT  GGCCATCCCC  1680
1681  TTCTTGGGGC  TGGCCGGGAA  GTTGCGTAAA  TAGAGCCCTC  1720
1721  TAAAGGATGC  AAAAGTCGTA  ACACGGTTT  1749
```

FIG.4B

```
  1  TAGTCATATG CTTGTCTCAA AGATTAAGCC ATGCATGTCT   40
 41  AAGTATAAGC TTTTATACGG TGAAACTGCG AATGGCTCAT   80
 81  TAAAACAGTT ATAGTTTATT TGATGGTCTC ATTTTACATG  120
121  GATAACCATG GTAATTCTAT GGCTAATACA TGCGCAAAGG  160
161  TCACCTCCTT TGGAGGGGCT GTGTTTATTA GATACAAAAC  200
201  CAACCCACTT AACGGTGGAG CCTTGGTGAT TCATAGTAAC  240
241  CGAACGGATC GCAGTTGGTT CTTTTGGACC CGCGATGGAT  280
281  CATTCAAGTT TCTGACCTAT CAGCTTTCGA CGGTAGGGTA  320
321  TTGGCCTACC GTGGCAGTGA CGGGTAACGG GGAATTAGGG  360
361  TTCGATTCCG GAGAGGGAGC CTGAGAAACG GCTACCACAT  400
401  CTAAGGAAGG CAGCAGGCGC GCAAATTACC CAATGAAAAC  440
441  AGCTTCGAGG TAGTGACGAG AAATAACAAT ACAGGGCATT  480
481  TTATGCTTTG TAATTGGAAT GATGGAAATG TAAAACCCTT  520
521  CCAGAGTAAC AATTGGAGGG CAAGTCTGGT GCCAGCAGCC  560
561  GCGGTAATTC CGGCTCCAAT AGTGTATATT AGAGTTGTTG  600
601  CAGTTAAAAA GCTCGTAGTT GGATTTCTGT CGTGGTCATC  640
641  CGGCGCCGCC CGTATGGGTG TGGGCCTGGC ATGCCCTCGG  680
681  CTTATTTCCG GTAGCCTTCC GCGCTTAATT GCGTGTGTTG  720
721  GTGTTCTGGA ACTTTTACTT TGAGAAAAAT AGAGTGTTTC  760
761  AAGCAGGCTT GTCGCCCTGA ATACTGCAGC ATGGAATAAT  800
801  AAGATAGGAC CTCGGTTCTA TTTTGTTGGT TTCTAGGACC  840
841  AAGGTAATGA TTAATAGGGA CAGTTGGGGG CATTTGTATT  880
881  TAACTGTCAG AGGTGAAATT CTTAGATTTG TTAAAGACGA  920
921  ACTACTGCGA AAGCATTTGC CAAGGATGTT TCATTAATC   960
```

FIG. 5A

```
 961  AAGAACGACA GTAGGGGGTT TGAAGACGAT TAGATACCGT 1000
1001  CGTAATCTCT ACCATAAACT ATGCCGACTA GAGATAGGGA 1040
1041  AACGCCTACC TTGGCTTCTC CTGCACCTCA TGAGAAATCA 1080
1081  AAGTCTCTGG GTTCTGGGGG GAGTATGGTC GCAAGGCTGA 1120
1121  AACTTAAAGG AATTGACGGA GGGGCACCAC CAGGCGTGGA 1160
1161  GCCTGCGGCT TAATTTGACT CAACACGGGG AAACTCACCA 1200
1201  GGTCCAGACA TGGGAAGGAT TGACAGATTG ATAGCTCTTT 1240
1241  CTTGATTCTA TGGGTGGTGG TGCATGGCCG TTCTTAGTTG 1280
1281  GTGGAGTGAT CTGTCTGGTT AATTTCGATA ACGAACGAGA 1320
1321  CCTTAGCCTG CTAAATAGGG TCAGTAACTT CACGATTACT 1360
1361  GTATCACTTC TTAGAGGGAC TTTGCGTGTC TAACGCAAGG 1400
1401  AAGTTTGAGG CAATAACAGG TCTGTGATGC CCTTAGATGT 1440
1441  TCTGGGCTGC ACGCGCGCTA CACTGATGCA TGCAACGAGT 1480
1481  TTTTACCTTG GCCGGCAGGT CTGGGTAATC TTTTGAGTGT 1520
1521  GCGTCGTGAT GGGGATAAAT TATTGCAATT ATTAATCTTC 1560
1561  AACGAGGAAT GCCTAGTAGG CGCAAGTCAG CAGCTTGCGC 1600
1601  CGATTAAGTC CCTGCCTCTT GTACACACCG CCCGTCGCTG 1640
1641  CAACCGATCG GAGGGTCCTG TGAATTCATC GGACGGACAA 1680
1681  GCCTTACTTT GTGGGCTGG TCGGGAAGTT GCGTAAATAG 1720
1721  AGCCCTCTAA AGGATGCAAA AGTCGTAACA CGGTTT 1756
```

FIG. 5B

| | | | | |
|---|---|---|---|---|
| 1 | TAGTCATATG | CTTGTCTCAA | AGATTAAGCC | ATGCATGTCT | 40 |
| 41 | AAGTATAAGC | TTTTATACGG | TGAAACTGCG | AATGGCTCAT | 80 |
| 81 | TAAAACAGTT | ATAGTTTATT | TGATGGTCTT | TTTTACATGG | 120 |
| 121 | ATAACCATGG | TAATTCTATG | CTAATACAT | ACGCAAAGGC | 160 |
| 161 | TACCTTCTCT | GGAGGGGCTG | TGTTTATTAG | ATACAAAACC | 200 |
| 201 | AACCCACTTT | TGTGGAGTCA | TGGTGATTCA | TAGTAACCGA | 240 |
| 241 | ACGGATCGCA | GTTGGCTTTC | GGGCCCGCGA | TGGATCATTC | 280 |
| 281 | AAGTTTCTGA | CCTATCAGCT | TTCGACGGTA | GGGTATTGGC | 320 |
| 321 | CTACCGTGGC | AGTGACGGGT | AACGGGGAAT | TAGGGTTCGA | 360 |
| 361 | TTCCGGAGAG | GGAGCCTGAG | AAACGGCTAC | CACATCTAAG | 400 |
| 401 | GAAGGCAGCA | GGCGCGCAAA | TTACCCAATG | AAAACAGTTT | 440 |
| 441 | CGAGGTAGTG | ACGAGAAATA | ACAATACAGG | GCATTTATG | 480 |
| 481 | CTTTGTAATT | GGAATGATGG | GAATGTAAAA | CCCTTCCAGA | 520 |
| 521 | GTAACAATTG | GAGGGCAAGT | CTGGTGCCAG | CAGCCGCGGT | 560 |
| 561 | AATTCCAGCT | CCAATAGTGT | ATATTAGAGT | TGTTGCAGTT | 600 |
| 601 | AAAAAGCTCG | TAGTTGGATT | TCTGTCGTGG | TCAGCCTGCG | 640 |
| 641 | CTGCCCGTAT | GGGTGTGCGC | GTGGTTTGCC | CTCGGCATAT | 680 |
| 681 | TTCTGGTAGC | CTCTGGCGCT | TTATTGCGTT | GGTAGGTGTT | 720 |
| 721 | CTGGAACTTT | TACTTTGAGA | AAAATAGAGT | GTTTCAAGCA | 760 |
| 761 | GGCTTGTCGC | CCTGAATACT | GCAGCATGGA | ATAATAAGAT | 800 |
| 801 | AGGACCTCGG | TTCTATTTTG | TTGGTTTCTA | GGACCAAGGT | 840 |
| 841 | AATGATTAAT | AGGGACAGTT | GGGGGCATTC | GTATTTAACT | 880 |
| 881 | GTCAGAGGTG | AAATTCTTAG | ATTTGTTAAA | GACGAACTAC | 920 |
| 921 | TGCGAAAGCA | TTTGCCAAGG | ATGTTTTCAT | TAATCAAGAA | 960 |
| 961 | CGACAGTAGG | GGGTTTGAAG | ACGATTAGAT | ACCGTCGTAA | 1000 |

FIG. 6A

| | | | | |
|---|---|---|---|---|
| 1001 | TCTCTACCAT | AAACTATGCC | GACTAGAGAT | AGGGAAATGC | 1040 |
| 1041 | CTACCTTGGC | TTCTCCTGCA | CCTCATGAGA | AATCAAAGTC | 1080 |
| 1081 | TCTGGGTTCT | GGGGGGAGTA | TGGTCGCAAG | GCTGAAACTT | 1120 |
| 1121 | AAAGGAATTG | ACGGAGGGGC | ACCACCAGGC | GTGGAGCCTG | 1160 |
| 1161 | CGGCTTAATT | TGACTCAACA | CGGGGAAACT | CACCAGGTCC | 1200 |
| 1201 | AGACATGGGA | AGGATTGACA | GATTGATAGC | TCTTTCTTGA | 1240 |
| 1241 | TTCTATGGGT | GGTGGTGCAT | GGCCGTTCTT | AGTTGGTGGA | 1280 |
| 1281 | GTGATCTGTC | TGGTTAATTT | CGATAACGAA | CGAGACCTTG | 1320 |
| 1321 | GCCTGCTAAA | TAGGGTCAGT | AACTTCGGTT | ACTGTATCAC | 1360 |
| 1361 | TTCTTAGAGG | GACTTTACGT | GTCTAACGCA | AGGAAGTTTG | 1400 |
| 1401 | AGGCAATAAC | AGGTCTGTGA | TGCCCTTAGA | TGTTCTGGGC | 1440 |
| 1441 | CGCACGCGCG | CTACACTGAT | GCATGCAACG | AGTTTTTACC | 1480 |
| 1481 | TTGCCCGATG | GGCTGGGTA | ATCTTGTGAG | GGTGCATCGT | 1520 |
| 1521 | GATGGGGATA | GATTATTGCA | ATTATTAGTC | TTCAACGAGG | 1560 |
| 1561 | AATGCCTAGT | AGGCGCAAGT | CAGCAGCTTG | CGCCGACTAC | 1600 |
| 1601 | GTCCCTGCCC | CTTGTACACA | CCGCCCGTCG | CTGCAACCGA | 1640 |
| 1641 | TCGGAGGGTC | CTGTGAATTC | ATCGGACTGG | CCAACCCCAC | 1680 |
| 1681 | TTTGGGGCTG | GCCGGGAAGT | TGCGTAAATA | GAGCCCTCTA | 1720 |
| 1721 | AAGGATGCAA | AAGTCGTAAC | ACGGTTT | 1747 |

FIG. 6B

|     |            |            |            |            |     |
|-----|------------|------------|------------|------------|-----|
| 1   | TAGTCATATG | CTTGTCTCAA | AGATTAAGCC | ATGCATGTCT | 40  |
| 41  | AAGTATAAGC | TTTTATACGG | TGAAACTGCG | AATGGCTCAT | 80  |
| 81  | TAAAACAGTT | ATAGTTTATT | TGATGGTCTC | ATTTTACATG | 120 |
| 121 | GATAACCATG | GTAATTCTAT | GGCTAATACA | TGCGCAAAGG | 160 |
| 161 | TCACCTCCTT | TGGAGGGGCT | GTGTTTATTA | GATACAAAAC | 200 |
| 201 | CAACCCACTT | TGTAGTGGAG | TCTTGGTGAT | TCATAGTAAC | 240 |
| 241 | CGAACGGATC | GCAGTTGGTT | CTTTTGGGCC | CGCGATGGAT | 280 |
| 281 | CATTCAAGTT | TCTGACCTAT | CAGCTTTCGA | CGGTAGGGTA | 320 |
| 321 | TTGGCCTACC | GTGGCAGTGA | CGGGTAACGG | GGAATTAGGG | 360 |
| 361 | TTCGATTCCG | GAGAGGGAGC | CTGAGAAACG | GCTACCACAT | 400 |
| 401 | CTAAGGAAGG | CAGCAGGCGC | GCAAATTACC | CAATGAAAAC | 440 |
| 441 | AGCTTCGAGG | TAGTGACGAG | AAATAACAAT | ACAGGCATT  | 480 |
| 481 | TTATGCTTTG | TAATTGGAAT | GATGGGAATG | TAAAACCCTT | 520 |
| 521 | CCAGAGTAAC | AATTGGAGGG | CAAGTCTGGT | GCCAGCAGCC | 560 |
| 561 | GCGGTAATTC | CAGCTCCAAT | AGTGTATATT | AGAGTTGTTG | 600 |
| 601 | CAGTTAAAAA | GCTCGTAGTT | GGATTCTGT  | CGTGGTCATC | 640 |
| 641 | CGGCGTCGCC | CGTATGGGTG | TGTGCCTGGC | ATGCCCTCGG | 680 |
| 681 | CTTATTTCCG | GTAGCCTTCC | GCGCTTAATT | GCGTGTGTTG | 720 |
| 721 | GTGTTCTGGA | ACTTTTACTT | TGAGAAAAAT | AGAGTGTTTC | 760 |
| 761 | AAGCAGGCTT | GTCGCCTGA  | ATACTGCAGC | ATGGAATAAT | 800 |
| 801 | AAGATAGGAC | CTCGGTTCTA | TTTTGTTGGT | TTCTAGGACC | 840 |
| 841 | AAGGTAATGA | TTAATAGGGA | CAGTTGGGGG | CATTCGTATT | 880 |
| 881 | TAACTGTCAG | AGGTGAAATT | CTTAGATTTG | TTAAAGACGA | 920 |
| 921 | ACTACTGCGA | AAGCATTTGC | CAAGGATGTT | TTCATTAATC | 960 |

FIG. 7A

```
 961  AAGAACGACA GTAGGGGGTT TGAAGACGAT TAGATACCGT  1000
1001  CGTAATCTCT ACCATAAACT ATGCCGACTA GAGATAGGGA  1040
1041  AACGCCTACC TTGGCTTCTC CTGCACCTCA TGAGAAATCA  1080
1081  AAGTCTCTGG GTTCTGGGGG GAGTATGGTC GCAAGGCTGA  1120
1121  AACTTAAAGG AATTGACGGA GGGGCACCAC CAGGCGTGGA  1160
1161  GCCTGCGGCT TAATTTGACT CAACACGGGG AAACTCACCA  1200
1201  GGTCCAGACA TGGGAAGGAT TGACAGATTG ATAGCTCTTT  1240
1241  CTTGATTCTA TGGGTGGTGG TGCATGGCCG TTCTTAGTTG  1280
1281  GTGGAGTGAT CTGTCTGGTT AATTTCGATA ACGAACGAGA  1320
1321  CCTTAGCCTG CTAAATAGGG TCAGTAACTT GCGGTTACT  1360
1361  GTATCACTTC TTAGAGGGAC TTTGCGTGTC TAACGCAAGG  1400
1401  AAGTTTGAGG CAATAACAGG TCTGTGATGC CCTTAGATGT  1440
1441  TCTGGGCTGC ACGCGCGCTA CACTGATGCA TGCAACGAGT  1480
1481  TTTTACCTTG GCCGACAGGT CTGGGTAATC TTTTGAGTGT  1520
1521  GCATCGTGAT GGGGATAGAT TATTGCAATT ATTAATCTTC  1560
1561  AACGAGGAAT GCCTAGTAGG CGCAAGTCAG CAGCTTGCGC  1600
1601  CGATTAAGTC CCTGCCTCTT GTACACACCG CCCGTCGCTG  1640
1641  CAACCGATCG GAGGGTCCTG TGAATTCATC GGACGGACAA  1680
1681  GCCTTACTTT GTGGGCTGG TCGGGAAGTT GCGTAAATAG  1720
1721  AGCCCTCTAA AGGATGCAAA AGTCGTAACA CAGTTT  1756
```

FIG. 7B

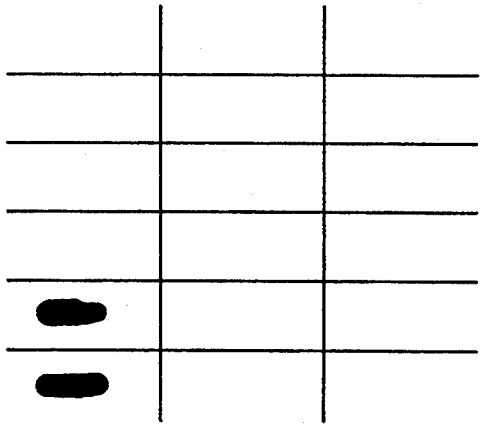
WEp1RC (57°C)
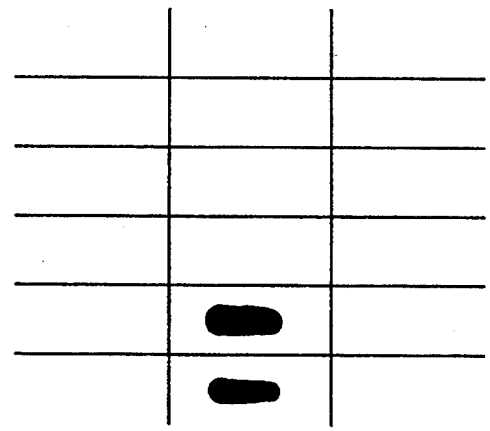
WEmx1RC (55°C)
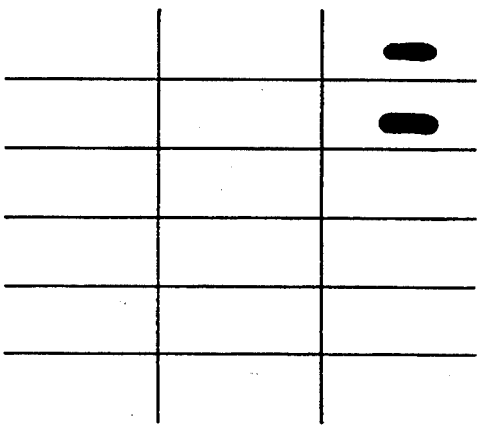
WEn1M (53°C)
| E. TENELLA | E. ACERVULINA | E. NECATRIX |
|---|---|---|
| E. TENELLA | E. ACERVULINA | E. NECATRIX |
| E. TENELLA | E. ACERVULINA | E. BRUNETTI |
| E. TENELLA | E. MITIS | E. BRUNETTI |
| E. PRAECOX | E. MAXIMA | CHICKEN |
| E. PRAECOX | E. MAXIMA | |
FIG.9

```
           201
Necatrix   CAACCCAC.T TAACGGTGGA GCCTTGGTGA TTCATAGTAA CCGAACGGAT
Tenella    CAACCCAC.T TTGTAGTGGA GTCTTGGTGA TTCATAGTAA CCGAACGGAT
Acervulina CAACCCAC.. CTTGTGTGGA GTCTTGGTGA TTCATAGTAA CCGAACGGAT
Praecox    CAACCCA... CTTTTGTGGA GTCATGGTGA TTCATAGTAA CCGAACGGAT
Brunetti   CAACCCAC.. CT..TGTGGA GCCTTGGTGA TTCATAGTAA CCGAACGGAT
Maxima     CAGCCCACAA TTCTTGTGGA GTCTTGGTGA TTCATAGTAA CCGAACGGAT
Mitis      CAACCCAC.. .TTTTGTGGA GCCTTGGTGA TTCATAGTAA CCGAACGGAT
Consensus  CAACCCAC-- -T-TTGTGGA GTCTTGGTGA TTCATAGTAA CCGAACGGAT 300
           CGCAGTTGGT TCTTTTGGAC CCGCGATGGA TCATTCAAGT TTCTGACCTA
           CGCAGTTGGT TCTTTTGGGC CCGCGATGGA TCATTCAAGT TTCTGACCTA
           CGCAGTTGG. .CTTTCGGGC CCGCGATGGA TCATTCAAGT TTCTGACCTA
           CGCAGTTGG. .CTTTCGGGC CCGCGATGGA TCATTCAAGT TTCTGACCTA
           CGCAGTTGG. .CTTTCGGGC CCGCGATGGA TCATTCAAGT TTCTGACCTA
           CGCAGTTGG. .CTTTCGGGC CCGCGATGGA TCATTCAAGT TTCTGACCTA
           CGCAGTTGG. .CTTTCGGGC CCGCGATGGA TCATTCAAGT TTCTGACCTA
           CGCAGTTGG- -CTTTCGGGC CCGCGATGGA TCATTCAAGT TTCTGACCTA
```

FIG. 12C

```
            301
Necatrix    TCAGCTTTCG ACGGTAGGGT ATTGGCCTAC CGTGGCAGTG ACGGGTAACG
Tenella     TCAGCTTTCG ACGGTAGGGT ATTGGCCTAC CGTGGCAGTG ACGGGTAACG
Acervulina  TCAGCTTTCG ACGGTAGGGT ATTGGCCTAC CGTGGCAGTG ACGGGTAACG
Praecox     TCAGCTTTCG ACGGTAGGGT ATTGGCCTAC CGTGGCAGTG ACGGGTAACG
Brunetti    TCAGCTTTCG ACGGTAGGGT ATTGGCCTAC CGTGGCAGTG ACGGGTAACG
Maxima      TCAGCTTTCG ACGGTAGGGT ATTGGCCTAC CGTGGCAGTG ACGGGTAACG
Mitis       TCAGCTTTCG ACGGTAGGGT ATTGGCCTAC CGTGGCAGTG ACGGGTAACG
Consensus   TCAGCTTTCG ACGGTAGGGT ATTGGCCTAC CGTGGCAGTG ACGGGTAACG 400
            GGGAATTAGG GTTCGATTCC GGAGAGGGAG CCTGAGAAAC GGCTACCACA
            GGGAATTAGG GTTCGATTCC GGAGAGGGAG CCTGAGAAAC GGCTACCACA
            GGGAATTAGG GTTCGATTCC GGAGAGGGAG CCTGAGAAAC GGCTACCACA
            GGGAATTAGG GTTCGATTCC GGAGAGGGAG CCTGAGAAAC GGCTACCACA
            GGGAATTAGG GTTCGATTCC GGAGAGGGAG CCTGAGAAAC GGCTACCACA
            GGGAATTAGG GTTCGATTCC GGAGAGGGAG CCTGAGAAAC GGCTACCACA
            GGGAATTAGG GTTCGATTCC GGAGAGGGAG CCTGAGAAAC GGCTACCACA
            GGGAATTAGG GTTCGATTCC GGAGAGGGAG CCTGAGAAAC GGCTACCACA
            GGGAATTAGG GTTCGATTCC GGAGAGGGAG CCTGAGAAAC GGCTACCACA
```

FIG. 12D

```
          401
Necatrix  TCTAAGGAAG GCAGCAGGCG CGCAAATTAC CCAATGAAAA CAGCTTCGAG
Tenella   TCTAAGGAAG GCAGCAGGCG CGCAAATTAC CCAATGAAAA CAGCTTCGAG
Acervulina TCTAAGGAAG GCAGCAGGCG CGCAAATTAC CCAATGAAAA CAGTTTCGAG
Praecox   TCTAAGGAAG GCAGCAGGCG CGCAAATTAC CCAATGAAAA CAGTTTCGAG
Brunetti  TCTAAGGAAG GCAGCAGGCG CGCAAATTAC CCAATGAAAA CAGTTTCGAG
Maxima    TCTAAGGAAG GCAGCAGGCG CGCAAATTAC CCAATGAAAA CAGTTTCGAG
Mitis     TCTAAGGAAG GCAGCAGGCG CGCAAATTAC CCAATGAAAA CAGTTTCGAG
Consensus TCTAAGGAAG GCAGCAGGCG CGCAAATTAC CCAATGAAAA CAGTTTCGAG 500
          GTAGTGACGA GAAATAACAA TACAGGGCAT TTTATGCTTT GTAATTGGAA
          GTAGTGACGA GAAATAACAA TACAGGGCAT TTTATGCTTT GTAATTGGAA
          GTAGTGACGA GAAATAACAA TACAGGGCAT TTTATGCTTT GTAATTGGAA
          GTAGTGACGA GAAATAACAA TAYAGGGCAT TTTATGCTTT GTAATTGGAA
          GTAGTGACGA GAAATAACAA TACAGGGCAT TTTATGCTTT GTAATTGGAA
          GTAGTGACGA GAAATAACAA TACAGGGCAT TTAATGCTTT GTAATTGGAA
          GTAGTGACGA GAAATAACAA TACAGGGCAT TTTATGCTTT GTAATTGGAA
          GTAGTGACGA GAAATAACAA TACAGGGCAT TTTATGCTTT GTAATTGGAA
```

FIG.12E

```
            501
Necatrix    TGATGGRAAT GTAAAACCCT TCCAGAGTAA CAATTGGAGG GCAAGTCTGG
Tenella     TGATGGGAAT GTAAAACCCT TCCAGAGTAA CAATTGGAGG GCAAGTCTGG
Acervulina  TGATGGGAAT GTAAAACCCT TCCAGAGTAA CAATTGGAGG GCAAGTCTGG
Praecox     TGATGGGAAT GTAAAACCCT TCCAGAGTAA CAATTGGAGG GCAAGTCTGG
Brunetti    TGATGGGAAT GTAAAACCCT TCCAGAGTAA CAATTGGAGG GCAAGTCTGG
Maxima      TGATGGGAAT GTAAAACCCT TCCAGAGTAA CAATTGGAGG GCAAGTCTGG
Mitis       TGATGGGAAT GTAAAACCCT TCCAGAGTAA CAATTGGAGG GCAAGTCTGG
Consensus   TGATGGGAAT GTAAAACCCT TCCAGAGTAA CAATTGGAGG GCAAGTCTGG 600
            TGCCAGCAGC CGCGGTAATT CCRGCTCCAA TAGTGTATAT TAGAGTTGTT
            TGCCAGCAGC CGCGGTAATT CCAGCTCCAA TAGTGTATAT TAGAGTTGTT
            TGCCAGCAGC CGCGGTAATT CCAGCTCCAA TAGTGTATAT TAGAGTTGTT
            TGCCAGCAGC CGCGGTAATT CCAGCTCCAA TAGTGTATAT TAGAGTTGTT
            TGCCAGCAGC CGCGGTAATT CCAGCTCCAA TAGTGTATAT TAGAGTTGTT
            TGCCAGCAGC CGCGGTAATT CCAGCTCCAA TAGTGTATAT TAGAGTTGTT
            TGCCAGCAGC CGCGGTAATT CCAGCTCCAA TAGTGTATAT TAGAGTTGTT
            TGCCAGCAGC CGCGGTAATT CCAGCTCCAA TAGTGTATAT TAGAGTTGTT
            TGCCAGCAGC CGCGGTAATT CCAGCTCCAA TAGTGTATAT TAGAGTTGTT
```

FIG. 12F

```
            601
Necatrix    GCAGTTAAAA AGCTCGTAGT TGGATTTCTG TCGTGGTCAT CCGGCGCCGC
Tenella     GCAGTTAAAA AGCTCGTAGT TGGATTTCTG TCGTGGTCAT CCGGCGTCGC
Acervulina  GCAGTTAAAA AGCTCGTAGT YGGATTTCTG TCGTGGTCAG CCTGCGCTGC
Praecox     GCAGTTAAAA AGCTCGTAGT TGGATTTCTG TCGTGGTCAG CCTGCGCTGC
Brunetti    GCAGTTAAAA AGCTCGTAGT TGGATTTCTG TCGTGGTCAG CCTGCGCTGC
Maxima      GCAGTTAAAA AGCTCGTAGT TGGATTTCTG TCGTGGTCAG CTTGCGCTGC
Mitis       GCAGTTAAAA AGCTCGTAGT TGGATTTCTG TCGTGGTCTT CCTGCGCTGC
Consensus   GCAGTTAAAA AGCTCGTAGT TGGATTTCTG TCGTGGTCAG CCTGCGCTGC 700
CCGTATGGGT GTGGGCCTGG CATGCCCCTCG GCTTATTTCC GGTAGCCTTC
CCGTATGGGT GTGTGCCTGG CATGCCCCTCG GCTTATTTCC GGTAGCCTTC
CCGTATGGGT GTGCGCGTGG TTTGCCCCTCG GCTTTTTTCT GGTAGCCTCC
CCGTATGGGT GTGCGCGTGG TTTGCCCCTCG GCATATTTCT GGTAGCCTCT
CCGTATGGGT GTGCGCGTGG TTTGCCCCTCG GCTTTCTTCC GGTAGCCTCC
CCGTATGGGT GTGCGCGTGG TTTGCCCCGCG GCTTCCTTCC GGTAGCCTCC
CCGTATCG.. GTGCACGTGG CTTGCCCCTCG ACTTTCTTCC GGTAGCTTGT
CCGTATGGGT GTGCGCGTGG TTTGCCCCTCG GCTTTTTTCC GGTAGCCTCC
```

FIG.12G

```
            701
Necatrix    CGCGCTTAAT TGCGTGTGTT GGTGTTCTGG AACTTTTACT TTGAGAAAAA
Tenella     CGCGCTTAAT TGCGTGTGTT GGTGTTCTGG AACTTTTACT TTGAGAAAAA
Acervulina  TGCGCTTAAT TGCGTGGGCT GGTGTTCCGG AACTTTTACT TTGAGAAAAA
Praecox     GGCGCTTTAT TGCGTTGGTA GGTGTTCTGG AACTTTTACT TTGAGAAAAA
Brunetti    GGCTCTTAAT TGCGTCGGTG GGTGTTCTGG AACTTTTACT TTGAGAAAAA
Maxima      GGCGCTTAAT TGCGTCTGCA AGTGCCCCTGG AACTTTTACT TTGAGAAAAA
Mitis       TGCGCTTCAC TGCGTGGGCT GGTGTTCTGG AACTTTTACT TTGAGAAAAA
Consensus   -GCGCTTAAT TGCGTGGGTT GGTGTTCTGG AACTTTTACT TTGAGAAAAA 800
TAGAGTGTTT CAAGCAGGCT TGTCGCCCTG AATACTGCAG CATGGAATAA
TAGAGTGTTT CAAGCAGGCT TGTCGCCCTG AATACTGCAG CATGGAATAA
TAGAGTGTTT CAAGCAGGCT TGTCGCCCTG AATACTGCAG CATGGAATAA
TAGAGTGTTT CAAGCAGGCT TGTCGCCCTG AATACTGCAG CATGGAATAA
TAGAGTGTTT CAAGCAGGCT TGTCGCCCTG AATACTGCAG CATGGAATAA
TAGAGTGTTT CAAGCAGGCT TGTCGCCCTG AATACTGCAG CATGGAATAA
TAGAGTGTTT CAAGCA.GCT TGTCGCCCTG AATACTGCAG CATGGAATAA
TAGAGTGTTT CAAGCAGGCT TGTCGCCCTG AATACTGCAG CATGGAATAA
```

FIG.12H

|            | 801         |            |            |            |            |
|------------|-------------|------------|------------|------------|------------|
| Necatrix   | TAAGATAGGA  | CCTCGGTTCT | ATTTTGTTGG | TTTCTAGGAC | CAAGGTAATG |
| Tenella    | TAAGATAGGA  | CCTCGGTTCT | ATTTTGTTGG | TTTCTAGGAC | CAAGGTAATG |
| Acervulina | TAAGATAGGA  | CCTCGGTTCT | ATTTTGTTGG | TTTCTAGGAC | CAAGGTAATG |
| Praecox    | TAAGATAGGA  | CCTCGGTTCT | ATTTTGTTGG | TTTCTAGGAC | CAAGGTAATG |
| Brunetti   | TAAGATAGGA  | CCTCGGTTCT | ATTTTGTTGG | TTTCTAGGAC | CAAGGTAATG |
| Maxima     | TAGGATAGGA  | CCTCGGTTCT | ATTTTGTTGG | TTTCTAGGAC | CAAGGTAATG |
| Mitis      | TAAGATAGGA  | CCTCGGTTCT | ATTTTGTTGG | TTTCTAGGAC | CAAGGTAATG |
| Consensus  | TAAGATAGGA  | CCTCGGTTCT | ATTTTGTTGG | TTTCTAGGAC | CAAGGTAATG |

|            |            |            |            |            | 900        |
|------------|------------|------------|------------|------------|------------|
| ATTAATAGGG | ACAGTTGGGG | GCATTYGTAT | TTAACTGTCA | GAGGTGAAAT |
| ATTAATAGGG | ACAGTTGGGG | GCATTCGTAT | TTAACTGTCA | GAGGTGAAAT |
| ATTARTAGGG | ACAGTTGGGG | GCATTCGTAT | TTAACTGTCA | GAGGTGAAAT |
| ATTAATAGGG | ACAGTTGGGG | GCATTCGTAT | TTAACTGTCA | GAGGTGAAAT |
| ATTAATAGGG | ACAGTTGGGG | GCATTCGTAT | TTAACTGTCA | GAGGTGAAAT |
| ATTAATAGGG | ACAGTTGGGG | GCATTCGTAT | TTAACTGTCA | GAGGTGAAAT |
| ATTAATAGGG | ACAGTTGGGG | GCATTCGTAT | TTAACTGTCA | GAGGTGAAAT |
| ATTAATAGGG | ACAGTTGGGG | GCATTCGTAT | TTAACTGTCA | GAGGTGAAAT |
| ATTAATAGGG | ACAGTTGGGG | GCATTCGTAT | TTAACTGTCA | GAGGTGAAAT |

FIG.12 I

```
              901
Necatrix    TCTTAGATTT GTTAAAGACG AACTACTGCG AAAGCATTTG CCAAGGATGT
Tenella     TCTTAGATTT GTTAAAGACG AACTACTGCG AAAGCATTTG CCAAGGATGT
Acervulina  TCTTAGATTT GTTAAAGACG AACTACTGCG AAAGCATTTG CCAAGGATGT
Praecox     TCTTAGATTT GTTAAAGACG AACTACTGCG AAAGCATTTG CCAAGGATGT
Brunetti    TCTTAGATTT GTTAAAGACG AACTACTGCG AAAGCATTTG CCAAGGATGT
Maxima      TCTTAGATTT GTTAAAGACG AACTACTGCG AAAGCATTTG CCAAGGATGT
Mitis       TCTTAGATTT GTTAAAGACG AACTACTGCG AAAG..TTTG CCAAGGATGT
Consensus   TCTTAGATTT GTTAAAGACG AACTACTGCG AAAGCATTTG CCAAGGATGT 1000
            TTTCATTAAT CAAGAACGAC AGTAGGGGGT TTGAAGACGA TTAGATACCG
            TTTCATTAAT CAAGAACGAC AGTAGGGGGT TTGAAGACGA TTAGATACCG
            TTTCATTAAT CAAGAACGAC AGTAGGGGGT TTGAAGACGA TTAGATACCG
            TTTCATTAAT CAAGAACGAC AGTAGGGGGT TTGAAGACGA TTAGATACCG
            TTTCATTAAT CAAGAACGAC AGTAGGGGGT TTGAAGACGA TTAGATACCG
            TTTCATTAAT CAAGAACGAC AGTAGGGGGT TTGAAGACGA TTAGATACCG
            TTTCATTAAT CAAGAACGAC AGTAGGGGGT TTGAAGACGA TTAGATACCG
            TTTCATTAAT CAAGAACGAC AGTAGGGGGT TTGAAGACGA TTAGATACCG
            TTTCATTAAT CAAGAACGAC AGTAGGGGGT TTGAAGACGA TTAGATACCG
```

FIG.12J

|            | 1001       |            |            |            |            |
|------------|------------|------------|------------|------------|------------|
| Necatrix   | TCGTAATCTC | TACCATAAAC | TATGCCGACT | AGAGATAGGG | AAACGCCTAC |
| Tenella    | TCGTAATCTC | TACCATAAAC | TATGCCGACT | AGAGATAGGG | AAACGCCTAC |
| Acervulina | TCGTAATCTC | TACCATAAAC | TATGCCGACT | AGAGATAGGG | AAATGCCTAC |
| Praecox    | TCGTAATCTC | TACCATAAAC | TATGCCGACT | AGAGATAGGG | AAATGCCTAC |
| Brunetti   | TCGTAATCTC | TACCATAAAC | TATGCCGACT | AGAGATAGGG | AAATGCCTAC |
| Maxima     | TCGTAATCTC | TACCATAAAC | TATGCCGACT | AGAGATAGGA | AAACGCCTCC |
| Mitis      | TCGTAATCTC | TACCATAAAC | TATGCCGACT | AGAGATAGGG | AAACGCCTAC |
| Consensus  | TCGTAATCTC | TACCATAAAC | TATGCCGACT | AGAGATAGGG | AAACGCCTAC |

|            |            |            |            |            | 1100       |
|------------|------------|------------|------------|------------|------------|
| CTTGGCTTCT | CCTGCACCTC | ATGAGAAATC | AAAGTCTCTG | GGTTCTGGGG |
| CTTGGCTTCT | CCTGCACCTC | ATGAGAAATC | AAAGTCTCTG | GGTTCTGGGG |
| CTTGGCTTCT | CCTGCACCTC | ATGAGAAATC | AAAGTCTCTG | GGTTCTGGGG |
| CTTGGCTTCT | CCTGCACCTC | ATGAGAAATC | AAAGTCTCTG | GGTTCTGGGG |
| CTTGGCTTCT | CCTGGACCTC | ATGAGAAATC | AAAGTCTCTG | GGTTCTGGGG |
| CTTGGCTTCT | CCTGCACCTC | ATGAGAAATC | AAAGTCTCTG | GGTTCTGGGG |
| CTTGGCTTCT | CCTGCACCTC | ATGAGAAATC | AAAGTCTCTG | GGTTCTGGGG |
| CTTGGCTTCT | CCTGCACCTC | ATGAGAAATC | AAAGTCTCTG | GGTTCTGGGG |

FIG.12K

```
            1101
Necatrix    GGAGTATGGT CGCAAGGCTG AAACTTAAAG GAATTGACGG AGGGGCACCA
Tenella     GGAGTATGGT CGCAAGGCTG AAACTTAAAG GAATTGACGG AGGGGCACCA
Acervulina  GGAGTATGGT CGCAAGGCTG AAACTTAAAG GAATTGACGG AGGGGCACCA
Praecox     GGAGTATGGT CGCAAGGCTG AAACTTAAAG GAATTGACGG AGGGGCACCA
Brunetti    GGAGTATGGT CGCAAGGCTG AAACTTAAAG GAATTGACGG AGGGGCACCA
Maxima      GGAGTATGGT CGCAAGGCTG AAACTTAAAG GAATTGACGG AGGGGCACCA
Mitis       GGAGTATGGT CGCAAGGCTG AAACTTAAAG GAATTGACGG AGGGGCACCA
Consensus   GGAGTATGGT CGCAAGGCTG AAACTTAAAG GAATTGACGG AGGGGCACCA 1200
            CCAGGCGTGG AGCCTGCGGC TTAATTTGAC TCAACACGGG GAAACTCACC
            CCAGGCGTGG AGCCTGCGGC TTAATTTGAC TCAACACGGG GAAACTCACC
            CCAGGCGTGG AGCCTGCGGC TTAATTTGAC TCAACACGGG GAAACTCACC
            CCAGGCGTGG AGCCTGCGGC TTAATTTGAC TCAACACGGG GAAACTCACC
            CCAGGCGTGG AG.CTGCGGC TTAATTTGAC TCAACACGGG GAAACTCACC
            CCAGGCGTGG AGCCTGCGGC TTAATTTGAC TCAACACGGG GAAACTCACC
            CCAGGCGTGG AGCC..GGGCC TTAATTTGAC TCAACACGGG GAAACTCACC
            CCAGGCGTGG AGCCTGCGGC TTAATTTGAC TCAACACGGG GAAACTCACC
```

FIG.12L

```
            1201
Necatrix    AGGTCCAGAC ATGGGAAGGA TTGACAGATT GATAGCTCTT TCTTGATTCT
Tenella     AGGTCCAGAC ATGGGAAGGA TTGACAGATT GATAGCTCTT TCTTGATTCT
Acervulina  AGGTCCAGAC ATGGGAAGGA TTGACAGATT GATAGCTCTT TCTTGATTCT
Praecox     AGGTCCAGAC ATGGGAAGGA TTGACAGATT GATAGCTCTT TCTTGATTCT
Brunetti    AGGTCCAGAC ATGGGAAGGA TTGACAGATT GATAGCTCTT TCTTGATTCT
Maxima      AGGTCCAGAC ATGGGAAGGA TTGACAGATT GATAGCTCTT TCTTGATTCT
Mitis       AGGTCCAGAC ATGGGAAGGA TTGACAGATT GATAGCTCTT TCCTGATTCT
Consensus   AGGTCCAGAC ATGGGAAGGA TTGACAGATT GATAGCTCTT TCTTGATTCT 1300
            ATGGGTGGTG GTGCATGGCC GTTCTTAGTT GGTGGAGTGA TCTGTCTGGT
            ATGGGTGGTG GTGCATGGCC GTTCTTAGTT GGTGGAGTGA TCTGTCTGGT
            ATGGGTGGTG GTGCATGGCC GTTCTTAGTT GGTGGAGTGA TCTGTCTGGT
            ATGGGTGGTG GTGCATGGCC GTTCTTAGTT GGTGGAGTGA TCTGTCTGGT
            ATGGGTGGTG GTGCATGGCC GTTCTTAGTT GGTGGAGTGA TCTGTCTGGT
            ATGGGTGGTG GTGCATGGCC GTTCTTAGTT GGTGGAGTGA TCTGTCTGGT
            ATGGGTGGTG GTGCATGGCC GTTCTTAGTT GGTGGAGTGA TTTGTCTGGT
            ATGGGTGGTG GTGCATGGCC GTTCTTAGTT GGTGGAGTGA TCTGTCTGGT
            ATGGGTGGTG GTGCATGGCC GTTCTTAGTT GGTGGAGTGA TCTGTCTGGT
```

FIG.12M

|            | 1301       |            |            |            |            |
|------------|------------|------------|------------|------------|------------|
| Necatrix   | TAATTTCGAT | AACGAACGAG | ACCTTAGCCT | GCTAAATAGG | GTCAGTAACT |
| Tenella    | TAATTTCGAT | AACGAACGAG | ACCTTAGCCT | GCTAAATAGG | GTCAGTAACT |
| Acervulina | TAATTTCGAT | AACGAACGAG | ACCTTGGCCT | GCTAAATAGG | GTCGGTAACT |
| Praecox    | TAATTTCGAT | AACGAACGAG | ACCTTGGCCT | GCTAAATAGG | GTCAGTAACT |
| Brunetti   | TAATTTCGAT | AACGAACGAG | ACCTTGGCCT | GCTAAATAGG | GTCGGTGACT |
| Maxima     | TAATTTCGAT | AACGAACGAG | ACCTTGGCCT | GCTAAATAGG | GTCGGTGACC |
| Mitis      | TAATTTCGAT | AACGAACGAG | ACCTTGGCCT | GCTAAATAGG | GTCGGTGACC |
| Consensus  | TAATTTCGAT | AACGAACGAG | ACCTTGGCCT | GCTAAATAGG | GTCGGTAACT |

|          |            |            |            | 1400       |
|----------|------------|------------|------------|------------|
| TCA......| CGATTACTGT | ATCACTTCTT | AGAGGGACTT | TGCGTGTCTA |
| TTG......| CGGTTACTGT | ATCACTTCTT | AGAGGGACTT | TGCGTGTCTA |
| T........| CGGTTATCGT | ATCACTTCTT | AGAGGGACTT | TGCGTGTCTA |
| T........| CGGTTACTGT | ATCACTTCTT | AGAGGGACTT | TGCGTGTCTA |
| T........| TGGTTACCGT | ATCGCTTCTT | AGAGGGACTT | TRCGTGTCTA |
| T........| CGGTTACCGT | ATCACTTCTT | AGAGGGACTT | TGCGTGTCTA |
| CTGGGTCACC | AGGTCACCGT | ATCACCGC | AGAGGGACAT | TGCGTGTCTA |
| T------- | CGGTTACCGT | ATCACTTCTT | AGAGGGACTT | TGCGTGTCTA |

FIG.12N

```
           1401
Necatrix   ACGCAAGGAA GTTTGAGGCA ATAACAGGTC TGTGATGCCC TTAGATGTTC
Tenella    ACGCAAGGAA GTTTGAGGCA ATAACAGGTC TGTGATGCCC TTAGATGTTC
Acervulina ACGCAAGGAA GTTTGAGGCA ATAACAGGTC TGTGATGCCC TTAGATGTTC
Praecox    ACGCAAGGAA GTTYGAGGCA ATAACAGGTC TGTGATGCCC TTAGATGTTC
Brunetti   ACGCAGGGAA GTTCGAGGCA ATAACAGGTC TGTGATGCCC TTAGATGTTC
Maxima     ACGCAAGGAA GTTTGAGGCA ATAACAGGTC TGTGATGCCC TTAGATGTTC
Mitis      ACGCAAGGAA GTTTGAGGCA ATAACAGGTC TGTGATGCCC TTAGATGTTC
Consensus  ACGCAAGGAA GTTTGAGGCA ATAACAGGTC TGTGATGCCC TTAGATGTTC 1500
           TGGGCTGCAC GCGCGCTACA CTGATGCATG CAACGAGTTT TTACCTTGGC
           TGGGCTGCAC GCGCGCTACA CTGATGCATG CAACGAGTTT TTACCTTGGC
           TGGGCTGCAC GCGCGCTACA CTGATGCATG CAACGAGTTT TTACCTTGAC
           TGGGCTGCAC GCGCGCTACA CTGATGCATG CAACGAGTYT TTACCTTGCC
           TGGGCCGCAC GCGCGCTACA CTGATGCATG CAACGAGTTT TTACCTTGCC
           TGGGCTGCAC GCGCGCTACA CTGATGCATG CAACGAGTTT TTACCTTGGC
           TGGGCTGCAC GCGCGCTACA CTGATGCATG CAACGAGTTT TCACCTTGTC
           TGGGCTGCAC GCGCGCTACA CTGATGCATG CAACGAGTTT TTACCTTGCC
           TGGGC-GCAC GCGCGCTACA CTGATGCATG CAACGAGTTT TTACCTTG-C
```

FIG.12 O

```
              1501
Necatrix    CGGCAGGTCT GGGTAATCTT TTGAGTGTGC RTCGTGATGG GGATARATTA
Tenella     CGACAGGTCT GGGTAATCTT TTGAGTGTGC ATCGTGATGG GGATAGATTA
Acervulina  CGACGGGGCT GGGTAATCTT CTGAGGGTGC ATCGTGATGG GGATAGATTA
Praecox     CGATGGGGCT GGGTAATCTT GTGAGGGTGC ATCGTGATGG GGATAGATTA
Brunetti    CGACGGGGCT GGGTAATCTT GTGGGGGTGC ATCGTGATGG GGATAGATTA
Maxima      CGACGGGGCT GGGTAATCTT GTGAGGGTGC ATCGTGATGG GGATAGATTA
Mitis       CGATGGGGCT GGGTAATCTT GTGAGGGTGC ATCGTGATGG GGATAGATTA
Consensus   CGACGGGGCT GGGTAATCTT GTGAGGGTGC ATCGTGATGG GGATAGATTA 1600
            TTGCAATTAT TAATCTTCAA CGAGGAATGC CTAGTAGGCG CAAGTCAGCA
            TTGCAATTAT TAATCTTCAA CGAGGAATGC CTAGTAGGCG CAAGTCAGCA
            TTGCAATTAT TAGTCTTCAA CGAGGAATGC CTAGTAGGCG CAAGTCAGCA
            TTGCAATTAT TAGTCTTCAA CGAGGAATGC CTAGTAGGCG CAAGTCAGCA
            TTGCAATTAT TAGTCTTCAA CGAGGAATGC CTAGTAGGCG CAAGTCAGCA
            TTGCAATTAT TAGTCTTCAA CGAGGAATGC CTAGTAGGCG CAAGTCAGCA
            TTGCAATTAT TAGTCTTCAA CGAGGAATGC CTAGTAGGCG CAAGTCAGCA
            TTGCAATTAT TAGTCTTCAA CGAGGAATGC CTAGTAGGCG CAAGTCAGCA
```

FIG.12P

```
            1601
Necatrix    GCTTGCGCCG ATTAAGTCCC TGCCTCTTGT ACACACCGCC CGTCGCTGCA
Tenella     GCTTGCGCCG ATTAAGTCCC TGCCTCTTGT ACACACCGCC CGTCGCTGCA
Acervulina  GCTTGCGCCG ATTACGTCCC TGCCTCTTGT ACACACCGCC CGTCGCTGCA
Praecox     GCTTGCGCCG ACTACGTCCC YGCCCCTTGT ACACACCGCC CGTCGCTGCA
Brunetti    GCTTGCGCCG ATTACGTCCC TGCCTCTTGT ACACACCGCC CGTCGCTGCA
Maxima      GCTTGCGCCG ATTAAGTCCC TGCCTCTTGT ACACACCGCC CGTCGCTGCA
Mitis       GCTTGTGCCG ATTAAGTCCC TGCCTCTTGT ACACACCGCC CGTCGCTGCA
Consensus   GCTTGCGCCG ATTACGTCCC TGCCTCTTGT ACACACCGCC CGTCGCTGCA 1700
            ACCGATCGGA GGGTCCCTGTG AATTCATCGG ACGGACAAGC CTTACTTTGT
            ACCGATCGGA GGGTCCCTGTG AATTCATCGG ACGGACAAGC CTTACTTTGT
            ACCGATCGGA GGGTCCCTGTG AATTCATCGG ACTGGCCATT CTCACTT..T
            ACCGATCGGA GGGTCCCTGTG AATTCATCGG ACTGGCCARC CCCACTT..T
            ACCGAT.GGA GGGTCCCTGTA AATTCATCGG ACTGGCCAAC CCCATTT..T
            ACCGATCGGA GGGTCCCTGTA AATTCATCGG ACTGACCAGC CCCAACT..T
            ACCGATCGGA GGGTCCCTGTG AATTCATCGG ATGGCCATCC C...CTTCTT
            ACCGATCGGA GGGTCCCTGTG AATTCATCGG ACTG-CCAGC C-CACTT---T
```

FIG. 12Q

|  | 1701 |  |  |  |  |  | 1764 |
|---|---|---|---|---|---|---|---|
| Necatrix | GGGGCTGGTC | GGGAAGTTGC | GTAAATAGAG | CCCTCTAAAG | GATGCAAAAG | TCGTAACACG | GTTT |
| Tenella | GGGGCTGGTC | GGGAAGTTGC | GTAAATAGAG | CCCTCTAAAG | GATGCAAAAG | TCGTAACACA | GTTT |
| Acervulina | GGGGCTGGCC | GGGAAGTTGC | GTAAATAGAG | CCCTCTAAAG | GATGCAAAAG | TCGTAACACG | GTTT |
| Praecox | GGGGCTGGCC | GGGAAGTTGC | GTAAATAGAG | CCCTCTAAAG | GATGCAAAAG | TCGTAACACG | GTTT |
| Brunetti | GGGGCTGGCT | GGAAAGTTGC | GTAAATAGAG | CCCTCTAAAG | GATGCAAAAG | TCGTAACACG | GTTT |
| Maxima | GGGGCTGGTC | GGAAAGTTGC | GTAAATAGAG | CCCTCTAAAG | GATGCAAAAG | TCGTAACACG | GTTT |
| Mitis | GGGGCTGGCC | GGGAAGTTGC | GTAAATAGAG | CCCTCTAAAG | GATGCAAAAG | TCGTAACACG | GTTT |
| Consensus | GGGGCTGGCC | GGGAAGTTGC | GTAAATAGAG | CCCTCTAAAG | GATGCAAAAG | TCGTAACACG | GTTT |

FIG.12R

|       | I |   |   |               | II |   |   |       |
|-------|---|---|---|---------------|----|---|---|-------|
| SLOT #| A | B | C |               | A  | B | C | SLOT #|
| 1     |   |   |   | E. ACERVULINA |    |   |   | 1     |
| 3     |   |   |   | E. BRUNETTI   |    |   |   | 3     |
| 5     |   |   |   | E. MITIS      |    |   |   | 5     |
|       | 1.24x* | 0.62x | 0.3x |         |    |   |   |       |
| 7     | ▬ | ▬ | ▬ | E. MAXIMA     |    |   |   | 7     |
| 9     |   |   |   | E. NECATRIX   |    |   |   | 9     |
|       |   |   |   |               | 1.0x* | 0.5x | 0.25x |   |
| 11    |   |   |   | E. TENELLA    | ▬ | ▬ | ▬ | 11    |
| 13    |   |   |   | E. PRAECOX    |    |   |   | 13    |
| 15    |   |   |   | CHICKEN       |    |   |   | 15    |
| 17    |   |   |   | HEPTAVALENT   |    |   |   | 17    |
| 19    | ▬ |   |   | HEPTAVALENT   | ▬  |   |   | 19    |

\* x10$^6$ SPOROCYSTS EQUIVALENT GENOMIC DNA

FIG.16

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
( A ) LENGTH: 19 bases
( B ) TYPE: nucleic acid
( C ) STRANDEDNESS: single
( D ) TOPOLOGY: linear ( x i ) SEQUENCE DESCRIPTION: SEQ ID NO:1:

ACCTGGTTGA TCCTGCCAG                19

( 2 ) INFORMATION FOR SEQ ID NO:2:

( i ) SEQUENCE CHARACTERISTICS:
( A ) LENGTH: 21 bases
( B ) TYPE: nucleic acid
( C ) STRANDEDNESS: single
( D ) TOPOLOGY: linear ( x i ) SEQUENCE DESCRIPTION: SEQ ID NO:2:

CTTCCGCAGG TTCACCTACG G                21

( 2 ) INFORMATION FOR SEQ ID NO:3:

( i ) SEQUENCE CHARACTERISTICS:
( A ) LENGTH: 19 bases
( B ) TYPE: nucleic acid
( C ) STRANDEDNESS: single
( D ) TOPOLOGY: linear ( x i ) SEQUENCE DESCRIPTION: SEQ ID NO:3:

TCCCTCTCCG GAATCGGAC                19

( 2 ) INFORMATION FOR SEQ ID NO:4:

( i ) SEQUENCE CHARACTERISTICS:
        ( A ) LENGTH: 16 bases
        ( B ) TYPE: nucleic acid
        ( C ) STRANDEDNESS: single
        ( D ) TOPOLOGY: linear ( x i ) SEQUENCE DESCRIPTION: SEQ ID NO:4:

CCAGGTCCAG ACATGG                                            16

( 2 ) INFORMATION FOR SEQ ID NO:5:

( i ) SEQUENCE CHARACTERISTICS:
        ( A ) LENGTH: 16 bases
        ( B ) TYPE: nucleic acid
        ( C ) STRANDEDNESS: single
        ( D ) TOPOLOGY: linear ( x i ) SEQUENCE DESCRIPTION: SEQ ID NO:5:

CTTGCGCCTA CTAGGC                                           16

( 2 ) INFORMATION FOR SEQ ID NO:6:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( x i ) SEQUENCE DESCRIPTION: SEQ ID NO:6:

CAGCCCACGC AATTAAGCGC AGGAG                            25

( 2 ) INFORMATION FOR SEQ ID NO:7:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( x i ) SEQUENCE DESCRIPTION: SEQ ID NO:7:

GAAGTGATAC GATAACCGAA GTT                                23

( 2 ) INFORMATION FOR SEQ ID NO:8:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:8:

CCCCTTCATA GAAAGGAAGC C                                      21

( 2 ) INFORMATION FOR SEQ ID NO:9:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( x i ) SEQUENCE DESCRIPTION: SEQ ID NO:9:

CCCCTTCAAA GAAGGAAGCC                                        20

( 2 ) INFORMATION FOR SEQ ID NO:10:

(i) SEQUENCE CHARACTERISTICS:
 (A) LENGTH: 16 bases
 (B) TYPE: nucleic acid
 (C) STRANDEDNESS: single
 (D) TOPOLOGY: linear (xi) SEQUENCE DESCRIPTION: SEQ ID NO:10:

TGCGTGACCG AGGTCA 16

(2) INFORMATION FOR SEQ ID NO:11:

(i) SEQUENCE CHARACTERISTICS:
 (A) LENGTH: 21 bases
 (B) TYPE: nucleic acid
 (C) STRANDEDNESS: single
 (D) TOPOLOGY: linear (xi) SEQUENCE DESCRIPTION: SEQ ID NO:11:

CAAGACTCCA CAAGAATTGT G 21

(2) INFORMATION FOR SEQ ID NO:12:

(i) SEQUENCE CHARACTERISTICS:
 (A) LENGTH: 20 bases
 (B) TYPE: nucleic acid
 (C) STRANDEDNESS: single
 (D) TOPOLOGY: linear (xi) SEQUENCE DESCRIPTION: SEQ ID NO:12:

GATACGGTAA CCGAGGTCAC 20

(2) INFORMATION FOR SEQ ID NO:13:

(i) SEQUENCE CHARACTERISTICS:
 (A) LENGTH: 19 bases
 (B) TYPE: nucleic acid
 (C) STRANDEDNESS: single
 (D) TOPOLOGY: linear (xi) SEQUENCE DESCRIPTION: SEQ ID NO:13:

CCAGAGGAGG GCCTATGCG 19

(2) INFORMATION FOR SEQ ID NO:14:

(i) SEQUENCE CHARACTERISTICS:
 (A) LENGTH: 21 bases
 (B) TYPE: nucleic acid
 (C) STRANDEDNESS: single
 (D) TOPOLOGY: linear (xi) SEQUENCE DESCRIPTION: SEQ ID NO:14:

CCAGAGGAGG AGGCCTATGC G 21

(2) INFORMATION FOR SEQ ID NO:15:

(i) SEQUENCE CHARACTERISTICS:
 (A) LENGTH: 17 bases
 (B) TYPE: nucleic acid
 (C) STRANDEDNESS: single
 (D) TOPOLOGY: linear (xi) SEQUENCE DESCRIPTION: SEQ ID NO:15:

TGACCTGGTG ACCCAGG 17

(2) INFORMATION FOR SEQ ID NO:16:

(i) SEQUENCE CHARACTERISTICS:
 (A) LENGTH: 20 bases
 (B) TYPE: nucleic acid
 (C) STRANDEDNESS: single (D) TOPOLOGY: linear (xi) SEQUENCE DESCRIPTION: SEQ ID NO:16:

CGTTAAGTGG GTTGGTTTTG 20

(2) INFORMATION FOR SEQ ID NO:17:

(i) SEQUENCE CHARACTERISTICS:
(A) LENGTH: 24 bases
(B) TYPE: nucleic acid
(C) STRANDEDNESS: single
(D) TOPOLOGY: linear (xi) SEQUENCE DESCRIPTION: SEQ ID NO:17:

AAGTGATACA GTAATCGTGA AGTT 24

(2) INFORMATION FOR SEQ ID NO:18:

(i) SEQUENCE CHARACTERISTICS:
(A) LENGTH: 21 bases
(B) TYPE: nucleic acid
(C) STRANDEDNESS: single
(D) TOPOLOGY: linear (xi) SEQUENCE DESCRIPTION: SEQ ID NO:18:

CACCATGACT CCACAAAAGT G 21

(2) INFORMATION FOR SEQ ID NO:19:

(i) SEQUENCE CHARACTERISTICS:
(A) LENGTH: 24 bases
(B) TYPE: nucleic acid
(C) STRANDEDNESS: single
(D) TOPOLOGY: linear (xi) SEQUENCE DESCRIPTION: SEQ ID NO:19:

AGAAGTGATA CAGTAACCGA AGTT 24

(2) INFORMATION FOR SEQ ID NO:20:

(i) SEQUENCE CHARACTERISTICS:
(A) LENGTH: 21 bases
(B) TYPE: nucleic acid
(C) STRANDEDNESS: single
(D) TOPOLOGY: linear (xi) SEQUENCE DESCRIPTION: SEQ ID NO:20:

CCAAGACTCC ACTACAAAGT G 21

(2) INFORMATION FOR SEQ ID NO:21:

(i) SEQUENCE CHARACTERISTICS:
(A) LENGTH: 22 bases
(B) TYPE: nucleic acid
(C) STRANDEDNESS: single
(D) TOPOLOGY: linear (xi) SEQUENCE DESCRIPTION: SEQ ID NO:21:

GTGATACAGT AACCGCAAAG TT 22

(2) INFORMATION FOR SEQ ID NO:22:

(i) SEQUENCE CHARACTERISTICS:
(A) LENGTH: 20 bases
(B) TYPE: nucleic acid
(C) STRANDEDNESS: single
(D) TOPOLOGY: linear (xi) SEQUENCE DESCRIPTION: SEQ ID NO:22:

AGCCATTCGC AGTTTCACCG                                                    20

( 2 ) INFORMATION FOR SEQ ID NO:23:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( x i ) SEQUENCE DESCRIPTION: SEQ ID NO:23:

AAGGTCTCGT TCGTTATCGA                                                    20

( 2 ) INFORMATION FOR SEQ ID NO:24:

( i ) SEQUENCE CHARACTERISTICS:
        ( A ) LENGTH: 1748 bases
        ( B ) TYPE: nucleic acid
        ( C ) STRANDEDNESS: single
        ( D ) TOPOLOGY: linear ( x i ) SEQUENCE DESCRIPTION: SEQ ID NO:24:

| | | | | |
|---|---|---|---|---|
| TAGTCATATG | CTTGTCTCAA | AGATTAAGCC | ATGCATGTCT | 40 |
| AAGTATAAGC | TTTTATACGG | TGAAACTGCG | AATGGCTCAT | 80 |
| TAAAACAGTT | ATAGTTTATT | TGATGGTCTC | TTTTACATGG | 120 |
| ATAACCATGG | TAATTCTATG | CTAATACAT | GCGCAAGGGC | 160 |
| CTCCTCCTCT | GGAGGGGCTG | TGTTTATTAG | ATACAAAACC | 200 |
| AACCCACCTT | GTGTGGAGTC | TTGGTGATTC | ATAGTAACCG | 240 |
| AACGGATCGC | AGTTGGCTTT | CGGGCCCGCG | ATGGATCATT | 280 |
| CAAGTTTCTG | ACCTATCAGC | TTTCGACGGT | AGGGTATTGG | 320 |
| CCTACCGTGG | CAGTGACGGG | TAACGGGGAA | TTAGGGTTCG | 360 |
| ATTCCGGAGA | GGGAGCCTGA | GAAACGGCTA | CCACATCTAA | 400 |
| GGAAGGCAGC | AGGCGCGCAA | ATTACCCAAT | GAAAACAGTT | 440 |
| TCGAGGTAGT | GACGAGAAAT | AACAATACAG | GGCATCTTAT | 480 |
| GCTTTGTAAT | TGGAATGATG | GGAATGTAAA | ACCCTTCCAG | 520 |
| AGTAACAATT | GGAGGGCAAG | TCTGGTGCCA | GCAGCCGCGG | 560 |
| TAATTCCAGC | TCCAATAGTG | TATATTAGAG | TTGTTGCAGT | 600 |
| TAAAAAGCTC | GTAGTTGGAT | TTCTGTCGTG | GTCAGCCTGC | 640 |
| GCTGCCCGTA | TGGGTGTGCG | CGTGGTTTGC | CCTCGGCTTT | 680 |
| TTTCTGGTAG | CCTCCTGCGC | TTAATTGCGT | GGGCTGGTGT | 720 |
| TCCGGAACTT | TTACTTTGAG | AAAAATAGAG | TGTTTCAAGC | 760 |
| AGGCTTGTCG | CCCTGAATAC | TGCAGCATGG | AATAATAAGA | 800 |
| TAGGACCTCG | GTTCTATTTT | GTTGGTTTCT | AGGACCAAGG | 840 |
| TAATGATTAA | TAGGGACAGT | TGGGGGCATT | CGTATTTAAC | 880 |
| TGTCAGAGGT | GAAATTCTTA | GATTTGTTAA | AGACGAACTA | 920 |
| CTGCGAAAGC | ATTTGCCAAG | GATGTTTTCA | TTAATCAAGA | 960 |
| ACGACAGTAG | GGGGTTTGAA | GACGATTAGA | TACCGTCGTA | 1000 |
| ATCTCTACCA | TAAACTATGC | CGACTAGAGA | TAGGGAAATG | 1040 |
| CCTACCTTGG | CTTCTCCTGC | ACCTCATGAG | AAATCAAAGT | 1080 |
| CTCTGGGTTC | TGGGGGAGT | ATGGTCGCAA | GGCTGAAACT | 1120 |

```
TAAAGGAATT GACGGAGGGG CACCACCAGG CGTGGAGCCT                   1160
GCGGCTTAAT TTGACTCAAC ACGGGGAAAC TCACCAGGTC                   1200
CAGACATGGG AAGGATTGAC AGATTGATAG CTCTTTCTTG                   1240
ATTCTATGGG TGGTGGTGCA TGGCCGTTCT TAGTTGGTGG                   1280
AGTGATCTGT CTGGTTAATT TCGATAACGA ACGAGACCTT                   1320
GGCCTGCTAA ATAGGGTCGG TAACTTCGGT TATCGTATCA                   1360
CTTCTTAGAG GGACTTTGCG TGTCTAACGC AAGGAAGTTT                   1400
GAGGCAATAA CAGGTCTGTG ATGCCCTTAG ATGTTCTGGG                   1440
CTGCACGCGC GCTACACTGA TGCATGCAAC GAGTTTTAC                    1480
CTTGACCGAC GGGGCTGGGT AATCTTCTGA GGGTGCATCG                   1520
TGATGGGGAT AGATTATTGC AATTATTAGT CTTCAACGAG                   1560
GAATGCCTAG TAGGCGCAAG TCAGCAGCTT GCGCCGATTA                   1600
CGTCCCTGCC TCTTGTACAC ACCGCCCGTC GCTGCAACCG                   1640
ATCGGAGGGT CCTGTGAATT CATCGGACTG GCCATTCTCA                   1680
CTTTGGGGCT GGCCGGGAAG TTGCGTAAAT AGAGCCCTCT                   1720
AAAGGATGCA AAAGTCGTAA CACGGTTT                                1748
```

( 2 ) INFORMATION FOR SEQ ID NO:25:

( i ) SEQUENCE CHARACTERISTICS:
( A ) LENGTH: 1744 bases
( B ) TYPE: nucleic acid
( C ) STRANDEDNESS: single
( D ) TOPOLOGY: linear ( x i ) SEQUENCE DESCRIPTION: SEQ ID NO:25:

```
TAGTCATATG CTTGTCTCAA AGATTAAGCC ATGCATGTCT                    40
AAGTATAAAC TTTTATACGG TGAAACTGCG AATGGCTCAT                    80
TAAAACAGTT ATAGTTTATT TGATGGTCAT TTTTACATGG                   120
ATAACCATGG TAATTCTATG GCTAATACAT GCGCATAGGC                   160
TTCCTTCTTT GAAGGGGCTG TGTTTATTAG ATACAAAACC                   200
AACCCACCTT GTGGAGCCTT GGTGATTCAT AGTAACCGAA                   240
CGGATCGCAG TTGGCTTTCG GGCCCGCGAT GGATCATTCA                   280
AGTTTCTGAC CTATCAGCTT TCGACGGTAG GGTATTGGCC                   320
TACCGTGGCA GTGACGGGTA ACGGGGAATT AGGGTTCGAT                   360
TCCGGAGAGG GAGCCTGAGA AACGGCTACC ACATCTAAGG                   400
AAGGCAGCAG GCGCGCAAAT TACCCAATGA AACAGTTTC                    440
GAGGTAGTGA CGAGAAATAA CAATACAGGG CATTTAATGC                   480
TTTGTAATTG GAATGATGGG AATGTAAAAC CCTTCCAGAG                   520
TAACAATTGG AGGGCAAGTC TGGTGCCAGC AGCCGCGGTA                   560
ATTCCAGCTC CAATAGTGTA TATTAGAGTT GTTGCAGTTA                   600
AAAAGCTCGT AGTTGGATTT CTGTCGTGGT CAGCCTGCGC                   640
TGCCCGTATG GGTGTGCGCG TGGTTTGCCC GCGGCTTTCT                   680
TCCGGTAGCC TCCGGCTCTT AATTGCGTCG GTGGGTGTTC                   720
TGGAACTTTT ACTTTGAGAA AAATAGAGTG TTTCAAGCAG                   760
GCTTGTCGCC CTGAATACTG CAGCATGGAA TAATAAGATA                   800
```

| | |
|---|---:|
| GGACCTCGGT TCTATTTTGT TGGTTTCTAG GACCAAGGTA | 840 |
| ATGATTAATA GGGACAGTTG GGGGCATTCG TATTTAACTG | 880 |
| TCAGAGGTGA AATTCTTAGA TTTGTTAAAG ACGAACTACT | 920 |
| GCGAAAGCAT TTGCCAAGGA TGTTTTCATT AATCAAGAAC | 960 |
| GACAGTAGGG GGTTTGAAGA CGATTAGATA CCGTCGTAAT | 1000 |
| CTCTACCATA AACTATGCCG ACTAGAGATA GGGAAATGCC | 1040 |
| TACCTTGGCT TCTCCTGCAC CTCATGAGAA ATCAAAGTCT | 1080 |
| CTGGGTTCTG GGGGAGTAT GGTCGCAAGG CTGAAACTTA | 1120 |
| AAGGAATTGA CGGAGGGGCA CCACCAGGCG TGGAGCCTGC | 1160 |
| GGCTTAATTT GACTCAACAC GGGGAAACTC ACCAGGTCCA | 1200 |
| GACATGGGAA GGATTGACAG ATTGATAGCT CTTTCTTGAT | 1240 |
| TCTATGGGTG GTGGTGCATG GCCGTTCTTA GTTGGTGGAG | 1280 |
| TGATCTGTCT GGTTAATTTC GATAACGAAC GAGACCTTGG | 1320 |
| CCTGCTAAAT AGGGTCGGTG ACCTCGGTCA CGCATCGCTT | 1360 |
| CTTAGAGGGA CTTTGCGTGT CTAACGCAGG GAAGTTCGAG | 1400 |
| GCAATAACAG GTCTGTGATG CCCTTAGATG TTCTGGGCTG | 1440 |
| CACGCGCGCT ACACTGATGC ATGCAACGAG TTCTTACCTT | 1480 |
| GGCCGACGGG CTGGGTAAT CTTGTGGGGG TGCATCGTGA | 1520 |
| TGGGGATAGA TTATTGCAAT TATTAGTCTT CAACGAGGAA | 1560 |
| TGCCTAGTAG GCGCAAGTCA GCAGCTTGCG CCGATTACGT | 1600 |
| CCCTGCCTCT TGTACACACC GCCCGTCGCT GCAACCGATG | 1640 |
| GAGGGTCCTG TAAATTCATC GGACTGGCCA ACCCCATTTT | 1680 |
| GGGGCTGGCT GGAAAGTTGC GTAAATAGAG CCCTCTAAAG | 1720 |
| GATGCAAAAG TCGTAACACG GTTT | 1744 |

(2) INFORMATION FOR SEQ ID NO:26:

(i) SEQUENCE CHARACTERISTICS:
    (A) LENGTH: 1750 bases
    (B) TYPE: nucleic acid
    (C) STRANDEDNESS: single
    (D) TOPOLOGY: linear (xi) SEQUENCE DESCRIPTION: SEQ ID NO:26:

| | |
|---|---:|
| TAGTCATATG CTTGTCTCAA AGATTAAGCC ATGCATGTCT | 40 |
| AAGTATAAAC TTTTATACGG TGAAACTGCG AATGGCTCAT | 80 |
| TAAAACAGTT ATAGTTTATT TGATGGTCTT TTTTACATGG | 120 |
| ATAACCATGG TAATTCTATG GCTAATACAT GCGCAAAAGC | 160 |
| TACCTTCTTT GGAGGAGCTG TGTTTATTAG ATACAAAACC | 200 |
| AGCCCACAAT TCTTGTGGAG TCTTGGTGAT TCATAGTAAC | 240 |
| CGAACGGATC GCAGTTGGCT TTCGGGCCCG CGATGGATCA | 280 |
| TTCAAGTTTC TGACCTATCA GCTTTCGACG GTAGGGTATT | 320 |
| GGCCTACCGT GGCAGTGACG GGTAACGGGG AATTAGGGTT | 360 |
| CGATTCCGGA GAGGGAGCCT GAGAAACGGC TACCACATCT | 400 |
| AAGGAAGGCA GCAGGCGCGC AAATTACCCA ATGAAACAG | 440 |

| | |
|---|---:|
| TTTCGAGGTA GTGACGAGAA ATAACAATAC AGGGCATTTT | 480 |
| ATGCTTTGTA ATTGGAATGA TGGGAATGTA AAACCCTTCC | 520 |
| AGAGTAACAA TTGGAGGGCA AGTCTGGTGC CAGCAGCCGC | 560 |
| GGTAATTCCA GCTCCAATAG TGTATATTAG AGTTGTTGCA | 600 |
| GTTAAAAAGC TCGTAGTTGG ATTTCTGTCG TGGTCAGCTT | 640 |
| GCGCTGCCCG TATGGGTGTG CGCGTGGTTT GCCCTCGGCA | 680 |
| TTCTTCCGGT AGCTTGTGGC GCTTAATTGC GTCTGCAAGT | 720 |
| GCCCTGGAAC TTTTACTTTG AGAAAAATAG AGTGTTTCAA | 760 |
| GCAGGCTTGT CGCCCTGAAT ACTGCAGCAT GGAATAATAG | 800 |
| GATAGGACCT CGGTTCTATT TTGTTGGTTT CTAGGACCAA | 840 |
| GGTAATGATT AATAGGGACA GTTGGGGGCA TTCGTATTTA | 880 |
| ACTGTCAGAG GTGAAATTCT TAGATTTGTT AAAGACGAAC | 920 |
| TACTGCGAAA GCATTTGCCA AGGATGTTTT CATTAATCAA | 960 |
| GAACGACAGT AGGGGGTTTG AAGACGATTA GATACCGTCG | 1000 |
| TAATCTCTAC CATAAACTAT GCCGACTAGA GATAGGAAAA | 1040 |
| CGCCTCCCTT GGCTTCTCCT GGACCTCATG AGAAATCAAA | 1080 |
| GTCTCTGGGT TCTGGGGGGA GTATGGTCGC AAGGCTGAAA | 1120 |
| CTTAAAGGAA TTGACGGAGG GGCACCACCA GGCGTGGAGC | 1160 |
| CTGCGGCTTA ATTTGACTCA ACACGGGGAA ACTCACCAGG | 1200 |
| TCCAGACATG GAAGGATTG ACAGATTGAT AGCTCTTTCC | 1240 |
| TGATTCTATG GGTGGTGGTG CATGGCCGTT CTTAGTTGGT | 1280 |
| GGAGTGATTT GTCTGGTTAA TTTCGATAAC GAACGAGACC | 1320 |
| TTGGCCTGCT AAATAGGGTC GGTGACCTCG GTTACCGTAT | 1360 |
| CACTTCTTAG AGGGACATTG CGTGTCTAAC GCAAGGAAGT | 1400 |
| TTGAGGCAAT AACAGGTCTG TGATGCCCTT AGATGTTCTG | 1440 |
| GGCTGCACGC GCGCTACACT GATGCATGCA ACGAGTTTTC | 1480 |
| ACCTTGTCCG ATGGGCTGG GTAATCTTGT GAGGGTGCAT | 1520 |
| CGTGATGGGG ATAGATTATT GCAATTATTA GTCTTCAACG | 1560 |
| AGGAATGCCT AGTAGGCGCA AGTCAGCAGC TTGTGCCGAT | 1600 |
| TACGTCCCTG CCTCTTGTAC ACACCGCCCG TCGCTGCAAC | 1640 |
| CGATCGGAGG GTCCTGTAAA TTCATCGGAC TGACCAGCCC | 1680 |
| CAACTTGGGG CTGGTCGGAA AGTTGCGTAA ATAGAGCCCT | 1720 |
| CTAAAGGATG CAAAAGTCGT AACACGGTTT | 1750 |

( 2 ) INFORMATION FOR SEQ ID NO:27:

( i ) SEQUENCE CHARACTERISTICS:
        ( A ) LENGTH: 1749 bases
        ( B ) TYPE: nucleic acid
        ( C ) STRANDEDNESS: single
        ( D ) TOPOLOGY: linear ( x i ) SEQUENCE DESCRIPTION: SEQ ID NO:27:

| | |
|---|---:|
| TAGTCATATG CTTGTCTCAA AGATTAAGCC ATGCATGTCT | 40 |
| AAGTATAAGC TTTTATACGG TGAAACTGCG AATGGCTCAT | 80 |
| TAAAACAGTT ATAGTTTATT TGATGGTCTT TTTTACATGG | 120 |

| | | |
|---|---|---|
| ATAACCATGG | TAATTCTATG GCTAATACAT GCGCATAGGC | 160 |
| CTCCTCCTCT | GGAGGGGCTG TGTTTATTAG CTACAAAACC | 200 |
| AACCCACTTT | TGTGGAGCCT TGGTGATTCA TAGTAACCGA | 240 |
| ACGGATCGCA | GTTGGCTTTC GGGCCCGCGA TGGATCATTC | 280 |
| AAGTTTCTGA | CCTATCAGCT TTCGACGGTA GGGTATTGGC | 320 |
| CTACCGTGGC | AGTGACGGGT AACGGGAAT TAGGGTTCGA | 360 |
| TTCCGGAGAG | GGAGCCTGAG AAACGGCTAC CACATCTAAG | 400 |
| GAAGGCAGCA | GGCGCGCAAA TTACCCAATG AAAACAGTTT | 440 |
| CGAGGTAGTG | ACGAGAAATA ACAATACAGG GCATTTTATG | 480 |
| CTTTGTAATT | GGAATGATGG GAATGTAAAA CCCTTCCAGA | 520 |
| GTAACAATTG | GAGGGCAAGT CTGGTGCCAG CAGCCGCGGT | 560 |
| AATTCCAGCT | CCAATAGTGT ATATTAGAGT TGTTGCAGTT | 600 |
| AAAAAGCTCG | TAGTTGGATT TCTGTCGTGG TCTTCCTGTG | 640 |
| CTGCCCGTAT | CGGTGCACGT GGCTTGCCCT CGACTTTCTT | 680 |
| CCGGTAGCCT | CCTGCGCTTC ACTGCGTGGG CTGGTGTTCT | 720 |
| GGAACTTTTA | CTTTGAGAAA AATAGAGTGT TTCAAGCAGC | 760 |
| TTGTCGCCCT | GAATACTGCA GCATGGAATA ATAAGATAGG | 800 |
| ACCTCGGTTC | TATTTTGTTG GTTTCTAGGA CCAAGGTAAT | 840 |
| GATTAATAGG | GACAGTTGGG GGCATTCGTA TTTAACTGTC | 880 |
| AGAGGTGAAA | TTCTTAGATT TGTTAAAGAC GAACTACTGC | 920 |
| GAAAGTTTGC | CAAGGATGTT TTCATTAATC AAGAACGACA | 960 |
| GTAGGGGGTT | TGAAGACGAT TAGATACCGT CGTAATCTCT | 1000 |
| ACCATAAACT | ATGCCGACTA GAGATAGGGA AACGCCTACC | 1040 |
| TTGGCTTCTC | CTGCACCTCA TGAGAAATCA AAGTCTCTGG | 1080 |
| GTTCTGGGGG | GAGTATGGTC GCAAGGCTGA AACTTAAAGG | 1120 |
| AATTGACGGA | GGGGCACCAC CAGGCGTGGA GCCGGGCCTT | 1160 |
| AATTTGACTC | AACACGGGGA AACTCACCAG GTCCAGACAT | 1200 |
| GGGAAGGATT | GACAGATTGA TAGCTCTTTC TTGATTCTAT | 1240 |
| GGGTGGTGGT | GCATGGCCGT TCTTAGTTGG TGGAGTGATC | 1280 |
| TGTCTGGTTA | ATTTCGATAA CGAACGAGAC CTTGGCCTGC | 1320 |
| TAAATAGGGT | CGGTGACCCT GGGTCACCAG GTCACCGCAT | 1360 |
| CGCTTCTTAG | AGGAACTTTG CGTGTCTAAC GCAAGGAAGT | 1400 |
| TTGAGGCAAT | AACAGGTCTG TGATGCCCTT AGATGTTCTG | 1440 |
| GGCTGCACGC | GCGCTACACT GATGCATGCA ACGAGTTTTT | 1480 |
| ACCTTGCCCG | ATGGGCGTGG GTAATCTTGT GAGGGTGCAT | 1520 |
| CGTGATGGGG | ATAGATTATT GCAATTATTA GTCTTCAACG | 1560 |
| AGGAATGCCT | AGTAGGCGCA AGTCAGCAGC TTGCGCCGAC | 1600 |
| TAAGTCCCTG | CCTCTTGTAC ACACCGCCCG TCGCTGCAAC | 1640 |
| CGATCGGAGG | GTCCTGTGAA TTCATCGGAT GGCCATCCCC | 1680 |
| TTCTTGGGGC | TGGCCGGGAA GTTGCGTAAA TAGAGCCCTC | 1720 |
| TAAAGGATGC | AAAAGTCGTA ACACGGTTT | 1749 |

( 2 ) INFORMATION FOR SEQ ID NO:28:

( i ) SEQUENCE CHARACTERISTICS:
        ( A ) LENGTH: 1756 bases
        ( B ) TYPE: nucleic acid
        ( C ) STRANDEDNESS: single
        ( D ) TOPOLOGY: linear ( x i ) SEQUENCE DESCRIPTION: SEQ ID NO:28:

| | | | | |
|---|---|---|---|---|
| TAGTCATATG | CTTGTCTCAA | AGATTAAGCC | ATGCATGTCT | 40 |
| AAGTATAAGC | TTTTATACGG | TGAAACTGCG | AATGGCTCAT | 80 |
| TAAAACAGTT | ATAGTTTATT | TGATGGTCTC | ATTTTACATG | 120 |
| GATAACCATG | GTAATTCTAT | GGCTAATACA | TGCGCAAAGG | 160 |
| TCACCTCCTT | TGGAGGGGCT | GTGTTTATTA | GATACAAAAC | 200 |
| CAACCCACTT | AACGGTGGAG | CCTTGGTGAT | TCATAGTAAC | 240 |
| CGAACGGATC | GCAGTTGGTT | CTTTTGGACC | CGCGATGGAT | 280 |
| CATTCAAGTT | TCTGACCTAT | CAGCTTTCGA | CGGTAGGGTA | 320 |
| TTGGCCTACC | GTGGCAGTGA | CGGGTAACGG | GGAATTAGGG | 360 |
| TTCGATTCCG | GAGAGGGAGC | CTGAGAAACG | GCTACCACAT | 400 |
| CTAAGGAAGG | CAGCAGGCGC | GCAAATTACC | CAATGAAAAC | 440 |
| AGCTTCGAGG | TAGTGACGAG | AAATAACAAT | ACAGGGCATT | 480 |
| TTATGCTTTG | TAATTGGAAT | GATGGAAATG | TAAAACCCTT | 520 |
| CCAGAGTAAC | AATTGGAGGG | CAAGTCTGGT | GCCAGCAGCC | 560 |
| GCGGTAATTC | CGGCTCCAAT | AGTGTATATT | AGAGTTGTTG | 600 |
| CAGTTAAAAA | GCTCGTAGTT | GGATTTCTGT | CGTGGTCATC | 640 |
| CGGCGCCGCC | CGTATGGGTG | TGGGCCTGGC | ATGCCCTCGG | 680 |
| CTTATTTCCG | GTAGCCTTCC | GCGCTTAATT | GCGTGTGTTG | 720 |
| GTGTTCTGGA | ACTTTTACTT | TGAGAAAAAT | AGAGTGTTTC | 760 |
| AAGCAGGCTT | GTCGCCCTGA | ATACTGCAGC | ATGGAATAAT | 800 |
| AAGATAGGAC | CTCGGTTCTA | TTTTGTTGGT | TTCTAGGACC | 840 |
| AAGGTAATGA | TTAATAGGGA | CAGTTGGGGG | CATTTGTATT | 880 |
| TAACTGTCAG | AGGTGAAATT | CTTAGATTTG | TTAAAGACGA | 920 |
| ACTACTGCGA | AAGCATTTGC | CAAGGATGTT | TTCATTAATC | 960 |
| AAGAACGACA | GTAGGGGGTT | TGAAGACGAT | TAGATACCGT | 1000 |
| CGTAATCTCT | ACCATAAACT | ATGCCGACTA | GAGATAGGGA | 1040 |
| AACGCCTACC | TTGGCTTCTC | CTGCACCTCA | TGAGAAATCA | 1080 |
| AAGTCTCTGG | GTTCTGGGGG | GAGTATGGTC | GCAAGGCTGA | 1120 |
| AACTTAAAGG | AATTGACGGA | GGGGCACCAC | CAGGCGTGGA | 1160 |
| GCCTGCGGCT | TAATTTGACT | CAACACGGGG | AAACTCACCA | 1200 |
| GGTCCAGACA | TGGGAAGGAT | TGACAGATTG | ATAGCTCTTT | 1240 |
| CTTGATTCTA | TGGGTGGTGG | TGCATGGCCG | TTCTTAGTTG | 1280 |
| GTGGAGTGAT | CTGTCTGGTT | AATTTCGATA | ACGAACGAGA | 1320 |
| CCTTAGCCTG | CTAAATAGGG | TCAGTAACTT | CACGATTACT | 1360 |
| GTATCACTTC | TTAGAGGGAC | TTTGCGTGTC | TAACGCAAGG | 1400 |

| | | | |
|---|---|---|---|
| AAGTTTGAGG | CAATAACAGG | TCTGTGATGC | CCTTAGATGT | 1440 |
| TCTGGGCTGC | ACGCGCGCTA | CACTGATGCA | TGCAACGAGT | 1480 |
| TTTTACCTTG | GCCGGCAGGT | CTGGGTAATC | TTTTGAGTGT | 1520 |
| GCGTCGTGAT | GGGGATAAAT | TATTGCAATT | ATTAATCTTC | 1560 |
| AACGAGGAAT | GCCTAGTAGG | CGCAAGTCAG | CAGCTTGCGC | 1600 |
| CGATTAAGTC | CCTGCCTCTT | GTACACACCG | CCCGTCGCTG | 1640 |
| CAACCGATCG | GAGGGTCCTG | TGAATTCATC | GGACGGACAA | 1680 |
| GCCTTACTTT | GTGGGGCTGG | TCGGGAAGTT | GCGTAAATAG | 1720 |
| AGCCCTCTAA | AGGATGCAAA | AGTCGTAACA | CGGTTT | 1756 |

( 2 ) INFORMATION FOR SEQ ID NO:29:

( i ) SEQUENCE CHARACTERISTICS:
        ( A ) LENGTH: 1747 bases
        ( B ) TYPE: nucleic acid
        ( C ) STRANDEDNESS: single
        ( D ) TOPOLOGY: linear ( x i ) SEQUENCE DESCRIPTION: SEQ ID NO:29:

| | | | |
|---|---|---|---|
| TAGTCATATG | CTTGTCTCAA | AGATTAAGCC | ATGCATGTCT | 40 |
| AAGTATAAGC | TTTTATACGG | TGAAACTGCG | AATGGCTCAT | 80 |
| TAAAACAGTT | ATAGTTTATT | TGATGGTCTT | TTTTACATGG | 120 |
| ATAACCATGG | TAATTCTATG | GCTAATACAT | ACGCAAAGGC | 160 |
| TACCTTCTCT | GGAGGGGCTG | TGTTTATTAG | ATACAAAACC | 200 |
| AACCCACTTT | TGTGGAGTCA | TGGTGATTCA | TAGTAACCGA | 240 |
| ACGGATCGCA | GTTGGCTTTC | GGGCCCGCGA | TGGATCATTC | 280 |
| AAGTTTCTGA | CCTATCAGCT | TTCGACGGTA | GGGTATTGGC | 320 |
| CTACCGTGGC | AGTGACGGGT | AACGGGGAAT | TAGGGTTCGA | 360 |
| TTCCGGAGAG | GGAGCCTGAG | AAACGGCTAC | CACATCTAAG | 400 |
| GAAGGCAGCA | GGCGCGCAAA | TTACCCAATG | AAAACAGTTT | 440 |
| CGAGGTAGTG | ACGAGAAATA | ACAATACAGG | GCATTTTATG | 480 |
| CTTTGTAATT | GGAATGATGG | GAATGTAAAA | CCCTTCCAGA | 520 |
| GTAACAATTG | GAGGGCAAGT | CTGGTGCCAG | CAGCCGCGGT | 560 |
| AATTCCAGCT | CCAATAGTGT | ATATTAGAGT | TGTTGCAGTT | 600 |
| AAAAAGCTCG | TAGTTGGATT | TCTGTCGTGG | TCAGCCTGCG | 640 |
| CTGCCCGTAT | GGGTGTGCGC | GTGGTTTGCC | CTCGGCATAT | 680 |
| TTCTGGTAGC | CTCTGGCGCT | TTATTGCGTT | GGTAGGTGTT | 720 |
| CTGGAACTTT | TACTTTGAGA | AAAATAGAGT | GTTTCAAGCA | 760 |
| GGCTTGTCGC | CCTGAATACT | GCAGCATGGA | ATAATAAGAT | 800 |
| AGGACCTCGG | TTCTATTTTG | TTGGTTTCTA | GGACCAAGGT | 840 |
| AATGATTAAT | AGGGACAGTT | GGGGGCATTC | GTATTTAACT | 880 |
| GTCAGAGGTG | AAATTCTTAG | ATTTGTTAAA | GACGAACTAC | 920 |
| TGCGAAAGCA | TTTGCCAAGG | ATGTTTTCAT | TAATCAAGAA | 960 |
| CGACAGTAGG | GGGTTTGAAG | ACGATTAGAT | ACCGTCGTAA | 1000 |
| TCTCTACCAT | AAACTATGCC | GACTAGAGAT | AGGGAAATGC | 1040 |
| CTACCTTGGC | TTCTCCTGCA | CCTCATGAGA | AATCAAAGTC | 1080 |

| | | | |
|---|---|---|---|
| TCTGGGTTCT | GGGGGGAGTA | TGGTCGCAAG | GCTGAAACTT | 1120 |
| AAAGGAATTG | ACGGAGGGGC | ACCACCAGGC | GTGGAGCCTG | 1160 |
| CGGCTTAATT | TGACTCAACA | CGGGGAAACT | CACCAGGTCC | 1200 |
| AGACATGGGA | AGGATTGACA | GATTGATAGC | TCTTTCTTGA | 1240 |
| TTCTATGGGT | GGTGGTGCAT | GGCCGTTCTT | AGTTGGTGGA | 1280 |
| GTGATCTGTC | TGGTTAATTT | CGATAACGAA | CGAGACCTTG | 1320 |
| GCCTGCTAAA | TAGGGTCAGT | AACTTCGGTT | ACTGTATCAC | 1360 |
| TTCTTAGAGG | GACTTTACGT | GTCTAACGCA | AGGAAGTTTG | 1400 |
| AGGCAATAAC | AGGTCTGTGA | TGCCCTTAGA | TGTTCTGGGC | 1440 |
| CGCACGCGCG | CTACACTGAT | GCATGCAACG | AGTTTTACC | 1480 |
| TTGCCCGATG | GGGCTGGGTA | ATCTTGTGAG | GGTGCATCGT | 1520 |
| GATGGGGATA | GATTATTGCA | ATTATTAGTC | TTCAACGAGG | 1560 |
| AATGCCTAGT | AGGCGCAAGT | CAGCAGCTTG | CGCCGACTAC | 1600 |
| GTCCCTGCCC | CTTGTACACA | CCGCCCGTCG | CTGCAACCGA | 1640 |
| TCGGAGGGTC | CTGTGAATTC | ATCGGACTGG | CCAACCCCAC | 1680 |
| TTTGGGGCTG | GCCGGGAAGT | TGCGTAAATA | GAGCCCTCTA | 1720 |
| AAGGATGCAA | AAGTCGTAAC | ACGGTTT | | 1747 |

( 2 ) INFORMATION FOR SEQ ID NO:30:

( i ) SEQUENCE CHARACTERISTICS:
    ( A ) LENGTH: 1756 bases
    ( B ) TYPE: nucleic acid
    ( C ) STRANDEDNESS: single
    ( D ) TOPOLOGY: linear ( x i ) SEQUENCE DESCRIPTION: SEQ ID NO:30:

| | | | |
|---|---|---|---|
| TAGTCATATG | CTTGTCTCAA | AGATTAAGCC | ATGCATGTCT | 40 |
| AAGTATAAGC | TTTTATACGG | TGAAACTGCG | AATGGCTCAT | 80 |
| TAAAACAGTT | ATAGTTTATT | TGATGGTCTC | ATTTTACATG | 120 |
| GATAACCATG | GTAATTCTAT | GGCTAATACA | TGCGCAAAGG | 160 |
| TCACCTCCTT | TGGAGGGGCT | GTGTTTATTA | GATACAAAAC | 200 |
| CAACCCACTT | TGTAGTGGAG | TCTTGGTGAT | TCATAGTAAC | 240 |
| CGAACGGATC | GCAGTTGGTT | CTTTTGGGCC | CGCGATGGAT | 280 |
| CATTCAAGTT | TCTGACCTAT | CAGCTTTCGA | CGGTAGGGTA | 320 |
| TTGGCCTACC | GTGGCAGTGA | CGGGTAACGG | GGAATTAGGG | 360 |
| TTCGATTCCG | GAGAGGGAGC | CTGAGAAACG | GCTACCACAT | 400 |
| CTAAGGAAGG | CAGCAGGCGC | GCAAATTACC | CAATGAAAAC | 440 |
| AGCTTCGAGG | TAGTGACGAG | AAATAACAAT | ACAGGGCATT | 480 |
| TTATGCTTTG | TAATTGGAAT | GATGGGAATG | TAAAACCCTT | 520 |
| CCAGAGTAAC | AATTGGAGGG | CAAGTCTGGT | GCCAGCAGCC | 560 |
| GCGGTAATTC | CAGCTCCAAT | AGTGTATATT | AGAGTTGTTG | 600 |
| CAGTTAAAAA | GCTCGTAGTT | GGATTTCTGT | CGTGGTCATC | 640 |
| CGGCGTCGCC | CGTATGGGTG | TGTGCCTGGC | ATGCCCTCGG | 680 |
| CTTATTTCCG | GTAGCCTTCC | GCGCTTAATT | GCGTGTGTTG | 720 |

| | |
|---|---|
| GTGTTCTGGA ACTTTTACTT TGAGAAAAAT AGAGTGTTTC | 760 |
| AAGCAGGCTT GTCGCCCTGA ATACTGCAGC ATGGAATAAT | 800 |
| AAGATAGGAC CTCGGTTCTA TTTTGTTGGT TTCTAGGACC | 840 |
| AAGGTAATGA TTAATAGGGA CAGTTGGGGG CATTCGTATT | 880 |
| TAACTGTCAG AGGTGAAATT CTTAGATTTG TTAAAGACGA | 920 |
| ACTACTGCGA AAGCATTTGC CAAGGATGTT TTCATTAATC | 960 |
| AAGAACGACA GTAGGGGGTT TGAAGACGAT TAGATACCGT | 1000 |
| CGTAATCTCT ACCATAAACT ATGCCGACTA GAGATAGGGA | 1040 |
| AACGCCTACC TTGGCTTCTC CTGCACCTCA TGAGAAATCA | 1080 |
| AAGTCTCTGG GTTCTGGGGG GAGTATGGTC GCAAGGCTGA | 1120 |
| AACTTAAAGG AATTGACGGA GGGGCACCAC CAGGCGTGGA | 1160 |
| GCCTGCGGCT TAATTTGACT CAACACGGGG AAACTCACCA | 1200 |
| GGTCCAGACA TGGGAAGGAT TGACAGATTG ATAGCTCTTT | 1240 |
| CTTGATTCTA TGGGTGGTGG TGCATGGCCG TTCTTAGTTG | 1280 |
| GTGGAGTGAT CTGTCTGGTT AATTTCGATA ACGAACGAGA | 1320 |
| CCTTAGCCTG CTAAATAGGG TCAGTAACTT TGCGGTTACT | 1360 |
| GTATCACTTC TTAGAGGGAC TTTGCGTGTC TAACGCAAGG | 1400 |
| AAGTTTGAGG CAATAACAGG TCTGTGATGC CCTTAGATGT | 1440 |
| TCTGGGCTGC ACGCGCGCTA CACTGATGCA TGCAACGAGT | 1480 |
| TTTTACCTTG GCCGACAGGT CTGGGTAATC TTTTGAGTGT | 1520 |
| GCATCGTGAT GGGGATAGAT TATTGCAATT ATTAATCTTC | 1560 |
| AACGAGGAAT GCCTAGTAGG CGCAAGTCAG CAGCTTGCGC | 1600 |
| CGATTAAGTC CCTGCCTCTT GTACACACCG CCCGTCGCTG | 1640 |
| CAACCGATCG GAGGGTCCTG TGAATTCATC GGACGGACAA | 1680 |
| GCCTTACTTT GTGGGGCTGG TCGGGAAGTT GCGTAAATAG | 1720 |
| AGCCCTCTAA AGGATGCAAA AGTCGTAACA CAGTTT | 1756 |

(2) INFORMATION FOR SEQ ID NO:31:

(i) SEQUENCE CHARACTERISTICS:
        (A) LENGTH: 16 bases
        (B) TYPE: nucleic acid
        (C) STRANDEDNESS: single
        (D) TOPOLOGY: linear (xi) SEQUENCE DESCRIPTION: SEQ ID NO:31:

| | |
|---|---|
| GTCGCAAGGC TGAAAC | 16 |

(2) INFORMATION FOR SEQ ID NO:32:

(i) SEQUENCE CHARACTERISTICS:
        (A) LENGTH: 16 bases
        (B) TYPE: nucleic acid
        (C) STRANDEDNESS: single
        (D) TOPOLOGY: linear (xi) SEQUENCE DESCRIPTION: SEQ ID NO:32:

| | |
|---|---|
| CTTGCGCCTA CTAGGC | 16 |

(2) INFORMATION FOR SEQ ID NO:33:

(i) SEQUENCE CHARACTERISTICS:

( A ) LENGTH: 23 bases
        ( B ) TYPE: nucleic acid
        ( C ) STRANDEDNESS: single
        ( D ) TOPOLOGY: linear ( x i ) SEQUENCE DESCRIPTION: SEQ ID NO:33:

GGGGGGAGTA TGGTCTGCAA GGC            23

( 2 ) INFORMATION FOR SEQ ID NO:34:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( x i ) SEQUENCE DESCRIPTION: SEQ ID NO:34:

GCATGCATCA GTGTAGCTGC GCG            23

( 2 ) INFORMATION FOR SEQ ID NO:35:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( x i ) SEQUENCE DESCRIPTION: SEQ ID NO:35:

TACGATAACC GAAGTTACCG            20

( 2 ) INFORMATION FOR SEQ ID NO:36:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:36:

GATACGGTAA CCAAAGTCAC C            21

( 2 ) INFORMATION FOR SEQ ID NO:37:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( x i ) SEQUENCE DESCRIPTION: SEQ ID NO:37:

GATACGGTAA CCGAGGTCA            19

( 2 ) INFORMATION FOR SEQ ID NO:38:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( x i ) SEQUENCE DESCRIPTION: SEQ ID NO:38:

CAAAACCAAC CCACTTAACG            20

( 2 ) INFORMATION FOR SEQ ID NO:39:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( x i ) SEQUENCE DESCRIPTION: SEQ ID NO:39:

TGATACAGTA ACCGAAGTTA CTG                                                                23

( 2 ) INFORMATION FOR SEQ ID NO:40:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( x i ) SEQUENCE DESCRIPTION: SEQ ID NO:40:

TACAGTAACC GCAAAGTTAC TG                                                                 22

( 2 ) INFORMATION FOR SEQ ID NO:41:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( x i ) SEQUENCE DESCRIPTION: SEQ ID NO:41:

GGTCTCGTTC GTTAATCGAA                                                                    20

( 2 ) INFORMATION FOR SEQ ID NO:42:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:42:

CATCACAGAC CTGTTATTGC C                                                                  21

( 2 ) INFORMATION FOR SEQ ID NO:43:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( x i ) SEQUENCE DESCRIPTION: SEQ ID NO:43:

CATAGAACGG CCATGCA                                                                       17

( 2 ) INFORMATION FOR SEQ ID NO:44:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( x i ) SEQUENCE DESCRIPTION: SEQ ID NO:44:

AAACTTAAAG GAATTGACGG                                                                    20

( 2 ) INFORMATION FOR SEQ ID NO:45:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( x i ) SEQUENCE DESCRIPTION: SEQ ID NO:45:

CGGTGTGTAC AAAGGGCAGG                                                                    20

(2) INFORMATION FOR SEQ ID NO:46:

(i) SEQUENCE CHARACTERISTICS:
        (A) LENGTH: 23 bases
        (B) TYPE: nucleic acid
        (C) STRANDEDNESS: single
        (D) TOPOLOGY: linear (xi) SEQUENCE DESCRIPTION: SEQ ID NO:46:

| | |
|---|---:|
| AACTTCGGTT ATCGTATCAC TTC | 23 |

(2) INFORMATION FOR SEQ ID NO:47:

(i) SEQUENCE CHARACTERISTICS:
        (A) LENGTH: 23 bases
        (B) TYPE: nucleic acid
        (C) STRANDEDNESS: single
        (D) TOPOLOGY: linear (xi) SEQUENCE DESCRIPTION: SEQ ID NO:47:

| | |
|---|---:|
| GTAACTTCGG TTATCGTATC ACT | 23 |

(2) INFORMATION FOR SEQ ID NO:48:

(i) SEQUENCE CHARACTERISTICS:
        (A) LENGTH: 21 bases
        (B) TYPE: nucleic acid
        (C) STRANDEDNESS: single
        (D) TOPOLOGY: linear (xi) SEQUENCE DESCRIPTION: SEQ ID NO:48:

| | |
|---|---:|
| CTTCGGTTAT CGTATCACTT C | 21 |

(2) INFORMATION FOR SEQ ID NO:49:

(i) SEQUENCE CHARACTERISTICS:
        (A) LENGTH: 21 bases
        (B) TYPE: nucleic acid
        (C) STRANDEDNESS: single
        (D) TOPOLOGY: linear (xi) SEQUENCE DESCRIPTION: SEQ ID NO:49:

| | |
|---|---:|
| ACTTCGGTTA TCGTATCACT T | 21 |

(2) INFORMATION FOR SEQ ID NO:50:

(i) SEQUENCE CHARACTERISTICS:
        (A) LENGTH: 508 bases
        (B) TYPE: nucleic acid
        (C) STRANDEDNESS: single
        (D) TOPOLOGY: linear (xi) SEQUENCE DESCRIPTION: SEQ ID NO:50:

| | | | | |
|---|---|---|---|---:|
| AAACTTAAAG | GAATTGACGG | AGGGGCACCA | CCAGGCGTGG | 40 |
| AGCCTGCGGC | TTAATTTGAC | TCAACACGGG | GAAACTCACC | 80 |
| AGGTCCAGAC | ATGGAAGGA | TTGACAGATT | GATAGCTCTT | 120 |
| TCTTGATTCT | ATGGGTGGTG | GTGCATGGCC | GTTCTTAGTT | 160 |
| GGTGGAGTGA | TCTGTCTGGT | TAATTTCGAT | AACGAACGAG | 200 |
| ACCTTGGCCT | GCTAAATAGG | GTCGGTGACT | TTGGTTACCG | 240 |
| TATCGCTTCT | TAGAGGGACT | TTGCGTGTCT | AACGCAAGGA | 280 |
| AGTTTGAGGC | AATAACAGGT | CTGTGATGCC | CTTAGATGTT | 320 |
| CTGGGCTGCA | CGCGCGCTAC | ACTGATGCAT | GCAACGAGTT | 360 |

| | | | | |
|---|---|---|---|---|
| TTTACCTTGA | CCGACGGGGC | TGGGTAATCT | TGTGAGGGTG | 400 |
| CATCGTGATG | GGGATAGATT | ATTGCAATTA | TTAGTCTTCA | 440 |
| ACGAGGAATG | CCTAGTAGGC | GCAAGTCAGC | ACTTGCGCCG | 480 |
| ATTACGTCCC | TGCCCTTTGT | ACACACCG | | 508 |

EIMERIA PRAECOX 16S RDNA PROBES

RELATED U.S. APPLICATION DATA

This application is a continuation-in-part of application Ser. No. 07/707,360, filed May 29, 1991, abandoned which is incorporated herein by reference.

BRIEF DESCRIPTION OF THE DRAWINGS

FIG. 1, A & B. Single strand nucleotide sequence for *E. acervulina* small subunit rRNA gene. (SEQ ID NO:24)

FIG. 2, A & B. Single strand nucleotide sequence for *E. brunetti* small subunit rRNA gene. (SEQ ID NO:25)

FIG. 3, A & B. Single strand nucleotide sequence for *E. maxima* small subunit rRNA gene. (SEQ ID NO:26)

FIG. 4, A & B. Single strand nucleotide sequence for *E. mitis* small subunit rRNA gene. (SEQ ID N0:27)

FIG. 5, A & B. Single strand nucleotide sequence for *E. necatrix* small subunit rRNA gene. (SEQ ID NO:28)

FIG. 6, A & B. Single strand nucleotide sequence for *E. praecox* small subunit rRNA gene. (SEQ ID NO:29)

FIG. 7, A & B. Single strand nucleotide sequence for *E. tenella* small subunit rRNA gene. (SEQ ID NO:30)

FIG. 9. Species-specific hybridization to genomic DNA isolated from purified preparations of Eimeria, showing that the Eimeria probes hybridize to both non-precocious laboratory isolates and vaccine strains.

FIG. 16. Direct fecal oocysts DNA target in probe hybridization/parasite quantitation assay.

BACKGROUND OF THE INVENTION

Figure 8:
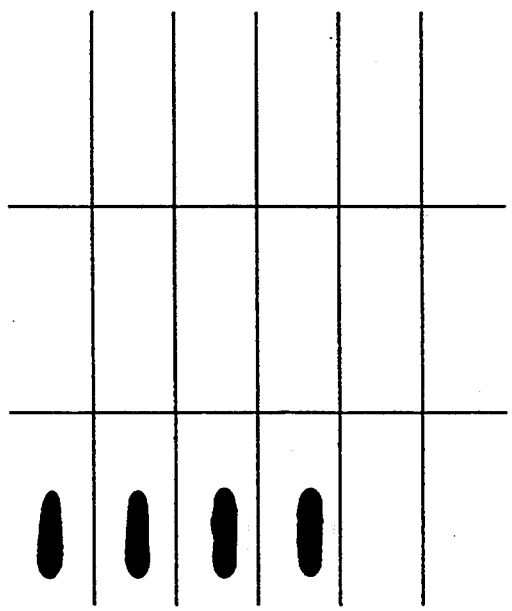
FIG. 8. Species-specific hybridization to genomic DNA isolated from purified preparations of Eimeria, showing the specificity of the *E. tenella* probe.

Live coccidiosis vaccines (LCV) consisting of particles composed of an immunogenic dose of oocysts from precocious isolates of chicken Eimeria species embedded in a firm gel matrix are well known in the art, as exemplified by U.S. Pat. Nos. 4,544,548, issued Oct. 1, 1985; 4,552,759 issued Nov. 12, 1985; 4,752,475 issued on Jun. 21, 1988; 4,863,731 issued Sep. 5, 1989 and Patent Cooperation Treaty, International Publication No. WO 85/00752. Evaluation of live coccidiosis vaccine characteristics such as viability of each of the species included in the vaccine is paramount to the production and use of the vaccine. In addition, any assay used to determine viability must also be semi-quantitative so that the immunogenic efficacy of each species in the particle can be predicted.

Viability of chicken Eimeria oocysts can only be credibly assessed by expansion or reproduction in the natural host, as no efficient in vitro models are available. The ability to detect parasites in the intestinal epithelia and mucosa of vaccinated birds, the target tissue for these protozoa, verifies that the organisms are in fact capable of penetrating the intestinal epithelium and intracellular development. Detection of oocysts shed in feces indicates that the inoculum contains fully competent parasites capable of traversing the entire life cycle.

Historically the Eimeria species (spp.) have been classified according to a range of parameters, including morphology, type of pathology induced, immunological specificity, characteristic life cycles and biochemical markers (Joyner and Long, Avian Path. 3, 145–157 [1974]); Shirley, In: McDougold, Joyher and Long, Eds., Research in Avian Coccidiosis, Athens, Georgia: University of Georgia, pp. 13–35 [1985]). However these methods of speciation are tedious and are not quantitative. Furthermore, no single method can unequivocally differentiate all species. Infectivity assays for multivalent live coccidiosis vaccines require unequivocal speciation, semi-quantitation and a streamlined procedure, owing to the anticipated short half life of the vaccine preparation. Existing methodologies do not satisfy these requirements.

The ribosomal RNA (rRNA) gene loci harbor a wealth of information that has been successfully used to establish phylogenetic relationships among and within eukaryotic kingdoms (Hasegawa et al., J. Mol. Evol. 22:32–80 [1985]). Ribosomal RNA genes from protozoa including *Toxoplasma gondii* (Johnson et al., Exp. Parasitol. 63:272–278 [1987]), members of the genus *Plasmodium* (Dame and McCutchan, J. Biol. Chem. 258:6984–6990 [1983], Langsley et al., Nucleic Acids Res. 11:8703–8717 [1983]) and Eimeria spp. (Ellis and Blumstead, Parasitol. 101:1–6 [1990]; Johnson et al., System. Parasitol. 18:1–8 [1991]) have been cloned and characterized towards this end. An extension of this type of analysis in *Plasmodium* (McCutchan et al., Mol. Biochem. Parasitol. 28: 63–68 [1988]) resulted in the design of species-specific oligonucleotide probes derived from the nucleotide sequence of areas within the small subunit rRNA gene.

OBJECTS OF THE INVENTION

It is accordingly, an object of the present invention to prepare purified Eimeria species DNA encoding small subunit ribosomal RNA (ssrRNA) genes free of other Eimeria nucleic acids and other cellular constituents. A further object is to insert the ssrRNA DNA into suitable vectors, transform an appropriate host with the vector and determine the nucleotide sequence of the DNA. Another object is to provide unique species-specific phylogenetically divergent segments of the ssrRNA genes which are used as probes for individual species. Another object is to prepare oligonucleotides complimentary to the divergent regions. Another object is to use the unique probes and assay to quantitate and/or identify each Eimeria species in a mixture of Eimeria species. A further object is to use the unique probes in a method to quantitate the relative levels of each of multiple Eimeria species in infected host tissue.

SUMMARY OF THE INVENTION

Unique species-specific *Eimeria praecox* DNA probes comprising divergent DNA sequences are disclosed. The probes are complementary to a small subunit ribosomal RNA gene of *Eimeria praecox*.

DETAILED DESCRIPTION OF THE INVENTION

The present invention relates to assays and species-specific identification probes which allows unequivocal speciation of multiple Eimeria species, semi-quantitation of the concentration of each species and a shortened time period for determining these parameters.

The following techniques have been used to identify deoxyribonucleic acid (DNA) probes that are specific for each of multiple species of Eimeria that are used to prepare a multivalent coccidiosis vaccine. DNA probe as used herein refers to a DNA sequence or segment, frequently labeled with radioactive isotopes, that is used to identify a gene. A DNA segment as used herein refers to a sequence of nucleotides between about 2 bases and about 2 kb (kilobases) in length. The Eimeria species include, but are not limited to, *E. acervulina, E. brunetti, E. maxima, E. mitis, E. necatrix, E. praecox* and *E. tenella*. An extended list of Eimeria species can be found in Patent Cooperation Treaty, Publication No. WO 85/00752. The small subunit rRNA gene from any or all of the Eimeria species is cloned and sequenced by the process described herein. Comparative analysis of these nucleotide sequences illustrates multiple segments within the sequence which are highly conserved across broad phylogenetic lines, as well as regions which are divergent even within a genus (i.e. spedes-specific). A conserved sequence refers to a DNA segment in a gene that has not changed in the course of evolution, while a divergent sequence refers to DNA segment that has changed considerably. Divergent sequences vary considerably in the length of the DNA segment which has changed. In the procaryotic genus Francisella, species can be differentiated by a single base difference in their ssrRNA genes, Forsman et al., Appl. Environ. Microbiol. 56:949–955 (1990). Trypanosomes, on the other hand, contain unique DNA segments in their ssrRNA genes which are several hundred bases long, Dams et al., Nucleic Acids Res. 165: r87-r173, (1988). The unique divergent sequences serve as ideal probes for identification of specific species within the genus *Eimeria*. Deoxyribooligonucleotides (single strands of DNA) corresponding to divergent sequences are synthesized, used as hybridization probes and act as effective species-specific reagents.

An assay of this type must be sufficiently sensitive so as to be able to detect the expansion or reproduction of a very small oocyst inoculum. In other models DNA hybridization probes have been successfully used to quantitate parasite load in infected hosts. For example, exoerythrocytic forms (EEF) of *Plasmodium berghei* have been assayed in genomic DNA prepared from rat liver extracts using a repetitive plasmodial DNA probe (Ferreira et al., Mol. Biochem. Parasitol. 19:103–109 [1986]). More recently, oligonucleotide probes derived from rRNA sequences have been employed to quantitate EEF of *Plasmodium yoelii* in RNA prepared from the livers of infected mice (Arreaza et al., Exp. Parasitol. 72:103–105 [1991]). Similarly, any assay for a live coccidiosis vaccine must be capable of detecting Eimeria sequences contained within a total nucleic acid preparation (whether it be RNA or DNA) from chicken intestinal epithelia and mucosa. Because the Eimeria sequences represent such a small percentage of the genetic information in the extract, direct hybridization to DNA is not sufficiently sensitive to detect the vaccine oocyst dose for each species. Because of the biological amplification of rRNA sequences within cellular RNA pools, hybridization of the Eimeria species-specific oligonucleotide probes to RNA preparations from intestinal epithelia and mucosa is one way in which this assay and oligonucleotide probes of this invention can be used. Genomic DNA prepared from oocysts shed in the feces of vaccinated birds can also be characterized as a hybridization target for the oligonucleotide probes. This source of parasite nucleic add is relatively free of host genetic material and so in effect represents an enriched hybridization target.

Enzymatic amplification of ssrRNA gene sequences in genomic DNA prepared from intestinal epithelia and mucosa is a novel alternative approach to enrichment which in the end allows for increased sensitivity in this unique assay. Using the polymerase chain reaction (PCR; Saiki et al., Science 239: 487–491 [1988]) and primers which efficiently hybridize to eukaryotic small subunit rRNA genes, it has been possible to selectively amplify each of the ssrRNA gene units or fragments thereof within the genomic DNA prepared from the intestinal epithelia and mucosa of infected chickens. Primer as used herein refers to a relatively short oligonucleotide that specifically attaches to a region of single-stranded template and is necessary to form the starting point for reverse transcriptase to copy adjacent sequences of RNA (mRNA, rRNA and tRNA), or for DNA polymerase to synthesize complementary-strand DNA. A primer can also be used with specific polymerases to produce complementary-strand synthesis with single-stranded genomic DNA, i.e. polymerase chain reaction. Complementary base pairing as used herein is defined as the linking of bases on double-stranded nucleic acids according to the base-pairing rules which are well known in the art. A complementary base sequence is a base sequence in a nucleic acid strand that is related to the base sequence in another strand by the same base-pairing rules. This includes Eimeria rRNA genes, chicken rRNA genes as well as rRNA genes derived from any other eukaryotic organism that might be represented in the chicken intestine. Amplification is selective in the sense that only small subunit rRNA genes are enriched as a result of the PCR reaction, but nonspecific because each small subunit rRNA gene is enriched to the same extent. The PCR amplification products are quantitated using a fluorescent dye binding assay (Labarca and Paigen, Anal. Biochem. 102:344–352 [1980]) and equivalent amounts of amplified DNA fragments are denatured and immobilized on a support membrane.

The species-specific oligonucleotide probes are then used in hybridization reactions to determine the presence or absence of each of the species of Eimeria in the amplified PCR product and therefore in the intestine of the vaccinated chickens. Hybridization reactions are defined as a reaction which results in the formation of a double-stranded molecule by complementary base-pairing between two single-stranded DNA molecules, or a single-stranded DNA molecule and an RNA molecule. A control hybridization probe, derived from a portion of the sequence contained within the PCR product in a region which is conserved in all eukaryotic small subunit rRNAs, is used to normalize the amount of denatured and immobilized DNA on the filter. Standards using genomic DNA prepared from individual species of Eimeria as PCR templates are included on each hybridization filter. These are used to construct a standard curve and will also serve as hybridization specificity standards. Radioactive emissions from the respective filters are quantitated using the Molecular Dynamics PhosphorImager (Johnston et al., Electrophoresis 11:355–360 [1990]).

The following method is used to clone Eimeria small subunit ribosomal RNA (rRNA) genes. It is intended that the following method is not the only process for cloning the Eimeria small subunit rRNA genes and that others known in the art can be used. Oocysts from laboratory strains of E. acervulina, E. brunetti, E. maxima, E. mitis, E. necatrix, E. praecox and E. tenella are propagated by oral infection of broiler chickens. Eimeria tenella oocysts are isolated from the cecal contents of chickens at about 5–7 days post-infection. The cecal contents are physically disrupted in a Waring Blender, in distilled water and digested with pepsin. Following digestion, debris is removed by centrifugation in distilled water. The remaining Eimeria species are individually isolated from fecal collections about 3–8 days following infection. The feces is diluted about ten fold in distilled water and then the contents are passed through a sieving device. A series of passes through screens of decreasing size functionally removes a considerable amount of fecal debris. Partially pure oocyst fractions for each Eimeria species are then collected by flotation in about 2.2 M sucrose (Jackson, Parasitel. 54:87–93 [1964]), and further treated by incubation in sodium hypochlorite at a concentration of 5.25%, in water at about 40° C. for about 10 minutes. The sodium hypochlorite is removed by several washes in sterile phosphate buffered saline (PBS) at about pH 7.6 to obtain purified, sterile oocysts. Depending upon the species, oocysts are allowed to sporulate in a shaking water bath for about 24 to about 60 hours at about 20° C. (Edgar, Trans. Am. Micr. Soc. 62:237–242 [1954]) in PBS or sterile water. Following sporulation, oocysts are washed several times in PBS.

Sporulated oocysts are disrupted by shaking with 3 mm sterile glass beads. Beads are added to the oocyst suspension and the mixture is mixed vigorously on a Vortex mixer for about 2 minutes. Periodically the extent of breakage is assessed microscopically. When approximately 50% breakage has occurred, the glass beads are allowed to settle and the sample above the beads is removed and mixed with an equal volume of Percoll (Pharmacia). The disrupted oocysts are subjected to centrifugation at about 2,000 to about 5,000 x g for about 10 rain at about 4° C. to pellet the enriched sporocyst fraction. Unbroken oocysts form a layer on top of the 50% Percoll and are removed, washed in PBS, mixed with glass beads and mixed again as described above. This procedure is performed repeatedly (3–4 times) until very few unbroken oocysts remain following Percoll fractionation. Sporocyst pellets are combined and washed several times in PBS.

Sporocysts are then diluted in 0.01 M Tris (pH 8.0), 0.2 M NaCl to a concentration of approximately $10^8$ per ml and the suspension is adjusted to about 1% sodium dodecyl sulfate (SDS) and about 10 mM EDTA which results in membrane lysis. The released genomic DNA is solubilized by digestion with Proteinase K (150 µg/ml) for approximately 30 minutes at about 65° C. Genomic DNA is extracted twice with buffer equilibrated phenol (about pH 7.6), twice with a mixture of phenol/chloroform/isoamyl alcohol at about 25:24:1, and twice with chloroform/isoamyl alcohol at about 24:1. The final aqueous phase is dialyzed overnight in 10 mM Tris (pH 8.0), 10 mM NaCl, 10 mM EDTA (pH 8.0). RNA which has co-purified with the DNA is selectively removed from the dialysate by digestion with heat inactivated RNase A used at a concentration of about 150 µMg/ml. The samples are incubated for about I hour at about 37° C. The RNase and other residual protein is removed by a secondary digestion with Proteinase K (about 150 µg/ml, for about 30 minutes at about 37° C.). The genomic DNA is then successively extracted with organic solvents as described above. The final aqueous phase is precipitated with about 0.1 volumes of about 3 M sodium acetate and about 2.5 volumes of about 100% ethanol. Glycogen is added to 20 µg/ml to act as carrier. The pellets are washed twice with about 70% ethanol. The genomic DNA pellet is air dried by inversion and is then suspended in about 10 mM Tris. HCl (pH 7.6), 1 mM EDTA buffer (TE) or distilled water at a concentration of about $5-8 \times 10^8$ sporocyst equivalents/ml and quantitated by absorbance at 260 nm. An aliquot of DNA is then analyzed by agarose gel electrophoresis to confirm (i) the spectrophotometric generated concentration, (ii) the lack of residual RNA, and (iii) it's high molecular weight integrity.

The ribosomal RNA (rRNA) gene loci harbor a wealth of information that has been successfully used to establish phylogenetic relationships among and within eukaryotic kingdoms (Hasegawa et al., J. Mol. Evol. 22:32–80 [1985]). Sequences of the small subunit rRNA from a number of highly divergent organisms have recently been compiled (Dams et al., Nucleic Acids Res. 16S: r87-r173 [1988], Neefs et al., Nucleic Acids Res. 18S: 2237–2317 [1990]). Comparative analysis of these nucleotide sequences identifies areas with dramatic sequence similarities and other areas that are characterized by considerable sequence drift or divergence. Regions dose to both the 5'- and 3'-ends of the consensus small subunit rRNA (ssrRNA) sequence with near identity in the eukaryotic kingdom were chosen. Consensus sequence is defined as a sequence of nucleotides derived from a large set of observed similar sequences in a specific region of a nucleic acid. Oligonucleotide primers corresponding to these sequences were chosen:

| | |
|---|---|
| 5'-ACCTGGTTGATCCTGCCAG-3' SEQ ID NO:1 | ERIB 1 |
| 5'-CTTCCGCAGGTTCACCTACGG-3' SEQ ID NO:2 | ERIB 10 |

The oligonucleotides were synthesized using an Applied Biosystems 380B instrument and purified as per the manufacturer's recommendations. The ERIB 1 (SEQ ID NO:1) primer represents a consensus sequence less than 10 nucleotides from the 5'-end of eukaryotic ssrRNA genes. The ERIB 10 (SEQ ID NO:2) primer is the inverse complement to a consensus sequence located approximately 20 nucleotides from the 3'-end of eukaryotic ssrRNA genes. Taken together, these two oligonucleotides span the vast majority of the ssrRNA gene sequence. It is intended that the ERIB 1 and ERIB 10 primers are not the only primers that can be used to amplify the ssrRNA genes or selected fragments thereof. With the knowledge of the present invention one could probably devise other primers which could accomplish the intended goal.

ERIB 1 (SEQ ID NO:1) and ERIB 10 (SEQ ID NO:2) are used as a primer pair in the polymerase chain reaction (PCR, Saiki et al., Science 239:487–491 [1988]) with the intention of selectively amplifying the ssrRNA genes contained within the genomic DNA preparation of each Eimeria species as described above. Genomic DNA is quantitated using a fluorescent dye binding assay (Lebarca and Paigen, Anal. Biochem. 102: 344–352 [1980]) and diluted in distilled water to a final concentration of about 2.5 ng/μl for use as the PCR template. A 10 X reaction buffer consisting of about 100 mM Tris-HCl (about pH 8.3), about 500 mM KCl, about 15 mM MgCl$_2$, about 0.01% gelatin is prepared as well as about 100 mM stocks of Tris-HCl ( about pH 7.6) buffered dATP, dCTP, dGTP and dTTP. Initially, the reaction mix cocktail is prepared by mixing the following components at these final concentrations in this specific order: water, dATP, dCTP, dGTP and dTTP (each at about 200 about 1 X reaction buffer, about 1 μM of each of the two oligonucleotide primers (ERIB I and ERIB 10) (SEQ ID NO:1, SEQ ID NO:2), and about 1.25 U Taq DNA polymerase. The reaction mixture is assembled in dedicated PCR reaction tubes by combining about 90 μl of the reaction cocktail with about 10 μl (25 ng) of genomic DNA. The reaction is overlayed with approximately 50 μl of light mineral oil and then placed into a Perkin Elmer Cetus DNA thermal cycler programmed as follows:

about 35 cycles each composed of (i) about 94° C. for about 60 seconds to denature, (ii) about 50° C. for about 90 seconds to anneal, and (iii) about 72° C. for about 120 seconds for polymerization about one cycle at about 72° C. for about 10 minutes for extension A 5 μl aliquot of the amplification reaction product is subjected to agarose gel DNA electrophoresis in TAE buffer (40 mM Tris-acetate, 2 mM ethylenediaminetetraacetic acid [EDTA]) along with DNA size standards. A characteristic band approximately 1.8 kb in length, whose size is roughly predicted by analogy to other eukaryotic ssrRNA genes, suggests that ERIB 1 (SEQ ID NO:1) and ERIB 10 (SEQ ID NO:2)faithfully hybridized to the Eimeria ssrRNA genes and that Taq DNA polymerase synthesized a reaction product by extension from the 3'-ends of these primers.

By definition, the ends of the 1.8 kb PCR products correspond to the input oligonucleotides and should be blunt. However, Taq DNA polymerase is prone to adding single non-template-directed nucleotides, in particular dATP, to the 3'-end of duplex PCR products (Clarke, Nucleic Adds Res. 16: 9677–9686 [1988]). In order to increase cloning efficiency, the ends of the PCR products are "polished" to blunt-ends by the action of either T4 DNA polymerase or the Klenow fragment of bacterial DNA polymerase. Reaction products are extracted once with phenol, once with a phenol/chloroform/isoamyl alcohol mix and once with chloroform/isoamyl alcohol as described earlier. DNA is precipitated with sodium acetate/ethanol and the pellet is washed twice with 70% ethanol. For the Klenow fragment reaction, the DNA (about 1–10 ]μg) is suspended in about 15 μl of water and mixed with about 2 μl of 10X nick translation buffer (about 0.5 M Tris.Cl [pH 7.2], 0.1 M MgSO$_4$, 1 mM dithiothreitol, 500 μg/ml bovine serum albumin [BSA Pentax Fraction V]), and about 2 μl of a 1.25 mM solution of all four dNTPs and about 1 μl (=5 Units) Klenow. The reaction is conducted at about 14° C. for about 1 hour and is terminated by heating at about 65° C. for about 10 minutes. The polished 1.8 kb DNA products are passed over a G 25 column, extracted once with phenol, and twice with chloroform/isoamyl alcohol as described earlier. The DNA is precipitated with sodium acetate/ethanol and the pellet is washed twice with about 70% ethanol. The DNA is resuspended in about 36 μl of water and mixed with about 4 μl of 0.2 M Tris.HCl (pH 9.5), 10 mM spermidine, 1 mM EDTA. This reaction mixture is incubated at about 70° C. for about 5 minutes and subsequently rapidly chilled on ice. To the above 40 μl are added 5 μl of 10X blunt end kinase buffer (0.5 M Tris. Cl [pH 9.5], 0.1 M MgCl$_2$, 50 mM dithiothreitol, 50% glycerol), and about 5 μl of a 10 mM solution of ATP and 2 μl (=20U) of T4 polynucleotide kinase. The reaction is conducted at about 37° C. for about 30 minutes and is terminated by the addition of about 2 μl of 0.5 M EDTA. The reaction mixture is brought to about 100 μl with TE buffer and the reaction products are extracted once with phenol, once with phenol/chloroform/isoamyl alcohol mix and once with chloroform/isoamyl alcohol as described previously. DNA is precipitated with sodium acetate/ethanol and the pellet is washed twice with about 70% ethanol, as above. The DNA is resuspended in about 20 μl of water and quantitated by absorbance at 260 nm.

The polished 1.8 kb DNA products are then agarose gel purified to remove residual oligonucleotide primers and nonspecific PCR products. Gel slices containing the bands of interest are excised, melted and the DNA eluted using Geneclean II (BIO 101 Inc., Vogelstein and Gillespie, Proc. Natl. Acad. Sci. USA 76:615–619 [1979]) as per the manufacturer's instructions. Eluted DNA products are then quantitated by absorbance at 260 nm.

A phagemid cloning vector pUC120 (Vieria, *Birepli-con Filamentous Phages and the Production of Single Stranded Plasmid* DNA. Ph.D. thesis, University of Minnesota [1989]) is cut at it's unique Sma I site in the polylinker. Other suitable cloning vectors include but are not limited to the pGEM-Zf series (Promega Corporation) and the pBluescript II series (Stratagene Cloning Systems). Cutting is monitored by analytical agarose gel electrophoresis. The linearized DNA is then extracted with organic solvents, precipitated and washed with 70% ethanol as described earlier. The 5'-end of each strand of the plasmid is phosphatased with calf intestinal phosphatase (CIP) to decrease the frequency of an autoligation event. This is accomplished by mixing the linearized plasmid about 10 μg with 5 μl of 10 X CIP buffer (about 0.5 M Tris-HCl, pH 9.0, about 10 mM MgCl$_2$, about 1 mM ZnCl$_2$, about 10 mM spermidine) and about 1 μl (1 Unit) of CIP in a final 50 μl reaction volume. The reaction is conducted for about 15 minutes at about 37° C. and then about 15 minutes at about 56° C. A second aliquot of CIP is then added and the reaction is repeated as above. The reaction is terminated by the addition of about 40 μl of H$_2$O, about 10 μl of about 10 X STE buffer (about 100 mM Tris-HCl, pH 8.0, about 1 M NaCl, about 10 mM EDTA), about 2.5 μl of about 20% SDS and heated at about 68° C. for about 15 minutes. The linearized, phosphatased vector is then extracted, precipitated and washed as above.

Ligation of the gel purified ssrRNA gene PCR products into the blunt Sma I site within the pUC120 polylinker is then conducted. Approximately 100 ng of linearized vector is mixed with an equimolar amount of the respective PCR products in a 20 μl reaction mixture which, in addition is composed of about 66 mM Tris-HCl pH 7.6, about 5 mM MgCl$_2$, about 5 mM dithiothreitol, about 1 mM ATP. The reaction is initiated by the addition of T4 DNA ligase (about 400 units) and proceeds for about 12-16 hours at about 14° C.

Bacterial cells are rendered competent and capable of uptake of foreign DNA by the following method. A predetermined volume (about 2 ml per transformation reaction) of sterile 2X YT bacterial media (about 16 g bactotryptone, about 10 g yeast extract, about 5 g NaCl per liter) is inoculated with a single colony of Escherichia coli MV1184 and grown with vigorous mixing at about 37° C. until it reached an optical density of about 0.6 at about 600 nm. Other suitable bacterial hosts include but are not limited to MN522, JM101, TB1 and XL1-Blue. The bacterial cells are collected by centrifugation at about 1000 x g, at about 4° C., for about 5 minutes. The resulting cell pellet is gently suspended in one-half of the original culture volume with sterile CaCl$_2$, about 50 mM. The suspension is then placed on ice for about 20 minutes and the cells are again collected by centrifugation. The cells are then gently suspended in one-tenth volume of sterile 50 mM CaCl$_2$. The bacterial suspension is then kept at 4° C. for 16-24 hours.

From the 20 μl ligation reaction mixture about 2 μl and about 18 μl aliquots are dispensed to sterile polypropylene tubes. Approximately 100 μl of competent bacteria are added to each of the tubes containing the ligation reactions (as well as the appropriate ligation and transformation controls) and these are placed on ice for 40 minutes. After this, the bacteria are "heat-shocked" by incubation at about 42° C. for 90 seconds and then allowed to recover for approximately 5 minutes at room temperature. Each transformation tube is then plated onto a 2X YT agar plate which contains ampicillin at a concentration of about 50 mg/l for the selection of bacteria harboring plasmids and for plasmid maintenance. Plates are incubated in an inverted position overnight at 37° C.

Bacterial clones harboring plasmids are selected by their ability to grow on plates in the presence of ampicillin. Single colonies are used to inoculate about 5 ml of 2X YT/AMP (i.e., 2X YT media containing ampicillin at 50 mg/l) and these cultures are grown overnight at about 37° C. with vigorous shaking. Approximately 1.5 ml of the culture is poured off into an Eppendorf tube and collected by centrifugation in an Eppendorf centrifuge for at least 1 min; the remainder of the culture is stored at about 4° C. to serve as a genetic stock. The media above the bacterial pellet is aspirated off and the pellet is suspended by mixing in about 100 μl of a cold, freshly prepared solution of about 50 mM glucose, about 10 mM EDTA, about 25 mM Tris-HCl (pH 8.0), about 4 mg/ml lysozyme. This mixture is incubated at room temperature for about 5 minutes. Then about 200 μl of a cold, freshly prepared solution, composed of about 0.2 N NaOH and about 1% SDS is added to each tube, mixed gently by inversion, and put on ice for about 5 minutes. About 150 μl of a cold, freshly prepared solution containing about 6 ml of about 5 M potassium acetate, about 1.15 ml of glacial acetic acid and about 2.85 ml distilled water is added to each tube. The contents are gently vortexed and this mixture is stored on ice for about 5 minutes. The cellular debris is collected by centrifugation in an Eppendorf centrifuge for 10 minutes at about 4° C. and the supernatant fluid is extracted one time with phenol/chloroform/isoamyl alcohol (about 25:24:1). Plasmid DNA and cellular RNA are precipitated from the final aqueous phase with the addition of two volumes of room temperature 100% ethanol. A pellet is collected by centrifugation for about 5 minutes at room temperature; the pellet is washed one time with 70% ethanol and then dried briefly. The nucleic acid pellet is then suspended in about 50 μl of TE containing about 20 μg of DNase-free RNase per ml and incubated for about 15-30 minutes at about 37° C. to quantitatively eliminate cellular RNA. Aliquots of about 10 μl are then cut to completion with Hind III and Eco R1 (each at approximately 20 units) in a buffer composed of about 50 mM NaCl, about 100 mM Tris-HCl (pH 7.5) and about 5 mM MgCl$_2$ at about 37° C. for about 60 min. The restriction enzyme reaction products are fractionated by agarose gel electrophoresis along with known DNA size markers to identify those plasmids which contained the appropriate inserts. Those recombinant plasmids which contain the predicted 1.8 kb insert are then cut with a second restriction enzyme (usually Pst I) to verify; (i) that only a single copy of the insert is contained within the plasmid, and (ii) to score for orientation of the insert DNA with respect to the bacterial promoter. This is accomplished by removing a second 10 μl aliquot from the remaining 40 μl of RNase-digested bacterial nucleic acid and cutting it in a buffer composed of about 100 mM NaCl, about 10 mM Tris-HCl (pH 7.5), about 10 mM MgCl$_2$ with approximately 20 units of Pst I for about 60 minutes at about 37° C. Again, the restriction enzyme digests are resolved by agarose gel electrophoresis.

Clones containing inserts of the appropriate size were then sequenced using the dideoxy sequencing protocol (Sanger et al J. Mol. Biol. 143:161-178 [1980]). Single stranded phagemid sequencing templates using KO7 helper phage were generated exactly as described by Vieria (Bireplicon Filamentous Phages and the Production of Single Stranded Plasmid DNA. Ph.D. thesis, University of Minnesota [1989]). Other commercially available helper phage for the generation of single-stranded templates from phagemid clones include R408 (Promega Corporation for use with the phagemid pGEM-Zf series and bacterial hosts MN522 or JM101) or VCSM13 and R408 (Stratagene Cloning Systems for use with the pBluescript II phagemid series and bacterial hosts XL1-Blue or NM522). Alternatively, double stranded sequencing templates were also used for dideoxy sequencing. These were prepared according to the method of Chen and Seeburg (DNA 4:165-170 [1985]). Sequencing reactions were conducted using a specifically engineered form of T7 DNA Polymerase (Tabor and Richardson, Proc. Natl. Acad. Sci. USA 84:4767-4771 [1987]). This enzyme is available commercially from Pharmacia LKB Biotechnology or as Sequenase DNA Polymerase (United States Biochemical Corporation). Reactions were conducted as per the respective manufacturer's specifications and the reaction products were resolved by denaturing polyacrylamide gel electrophoresis (Sanger et al J. Mol. Biol. 143:161-178 [1980]).

Examples of isolated and purified genes encoding the small subunit ribosomal RNA of Eimeria species are shown in FIGS. 1-7. The ssrRNA gene nucleotide sequences are compared to determine the conserved and divergent regions of the sequences. Divergent regions are identified following comparison and exemplified by the probes illustrated in Table 1. It is intended that the present invention include all of the divergent DNA regions of the ssrRNA genes of Eimeria species. The divergent regions are further defined as DNA sequences of about 1 to about 50 or about 1 to about 100 nucleotides in length that are not conserved within the organisms that make up the genus Eimeria. It is preferred that the divergent species-specific sequences are found within the ssrRNA of the following Eimeria species: Eimeria species such as: *E. acervulina, E. tenella, E. maxima, E. necatrix, E. praecox, E. mitis, E. brunetti*. The divergent sequences are identified by comparing the nucleotide sequences shown in FIGS. 1-7.

Figure 12A:
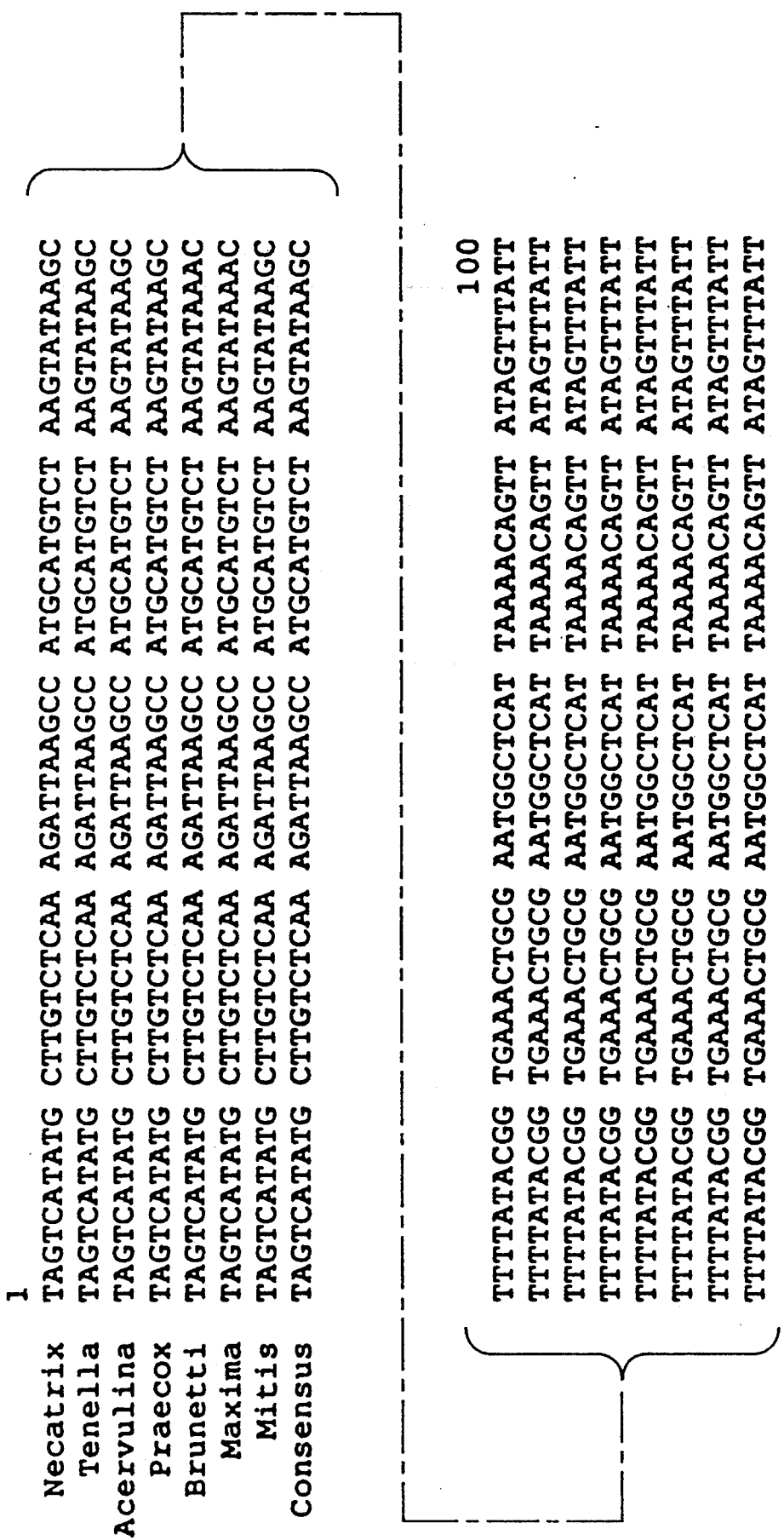
FIG. 12. Multiple nucleotide sequence alignment for chicken Eimeria using the sequences in FIGS. 1-7. (SEQ ID NO:24-30)
Figure 12B:
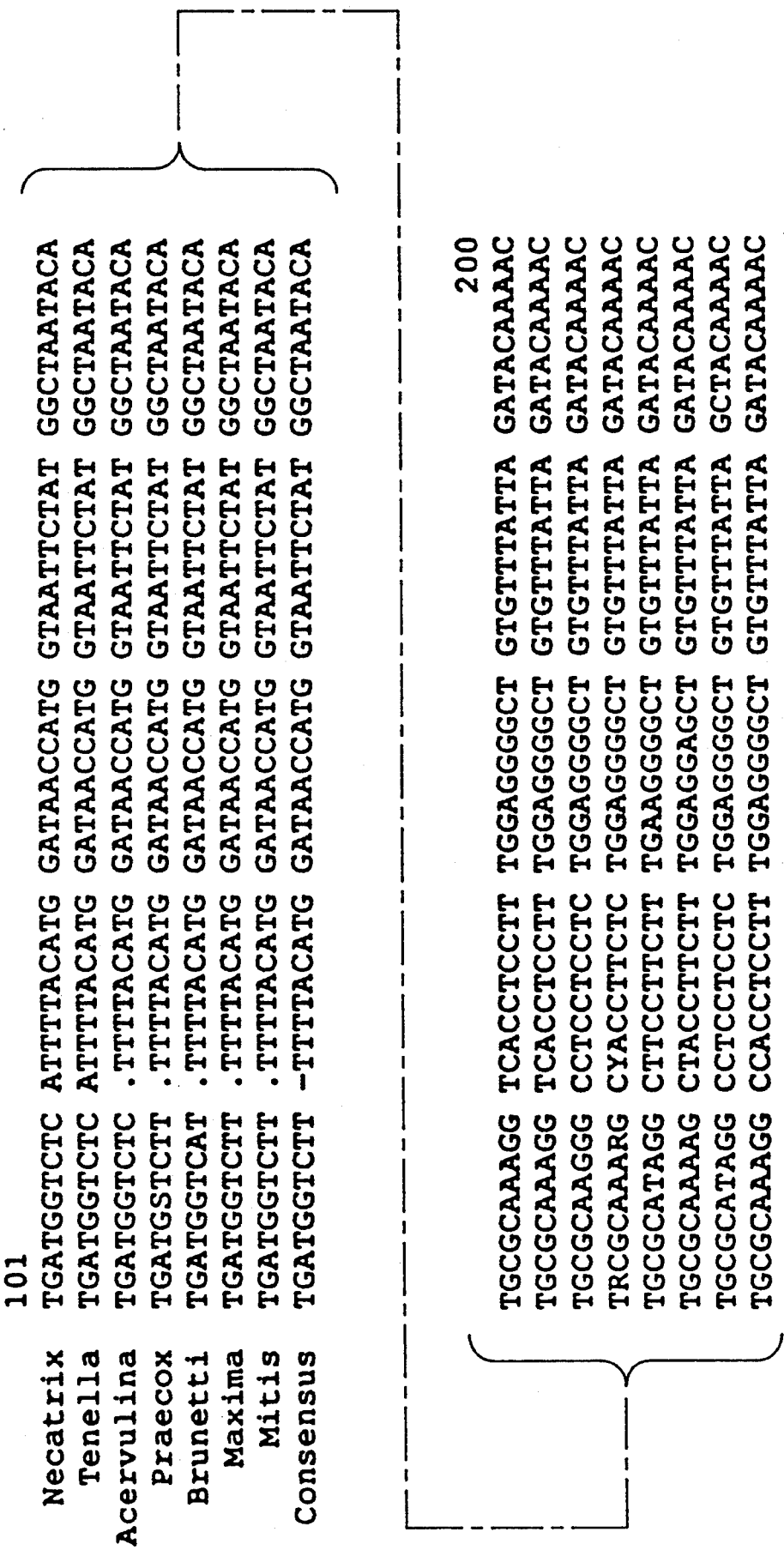

Table 1 represents the similarity matrix for the seven Eimeria species represented in FIGS. 1-7. This data was calculated using a computer program entitled PILEUP (GCG Software Package, Devereux, Haeberli and Smithies (1984 and A Comprehensive Set of Sequence Analysis Programs for the VAX. Nucleic Acids Research 12(1); 387–395) using the entire sequence as formatted in FIG. 12. Fundamentally the program does a base by base comparison of all possible pairs of sequences. The diagonal represents a self comparison which is 100% identity. The analysis reveals that the chicken Eimeria are a closely related group. The most similar pair is represented by *E. tenella* and *E. necatrix* whose ssrRNA sequences are 99.3% similar. From another view, this pair has 0.7% dissimilar nucleotide sequences, which over the entire length of approximately 1750 bases implies about 12 nucleotide differences. The most dissimilar pair is represented by *E. tenella* and *E. mitis* which are 96.4% similar, which implies about 63 nucleotide differences. Thus on a global basis the ssrRNA genes in the chicken Eimeria are very similar. Fortunately the differences which do exist seem to be clustered forming divergent regions, as seen in FIG. 12. If all or a majority of the nucleotide differences were found in one region then oligonucleotides which were very dissimilar could be made which would be species-specific. Since the positions of the nucleotide differences are not highly concentrated, the unique oligonucleotides disclosed herein would superficially look very similar in some cases having about 2 nucleotide differences out of a total of about 20 nucleotides. It is this similarity in sequence which has necessitated the use of highly stringent hybridization conditions. By highly stringent hybridization conditions we mean, that conditions (salt concentrations and hybridization and wash temperatures) are such that only perfect hybrids are formed (i.e. all bases in the oligonucleotide hybridization probe perfectly base pair or bond with the PCR amplified fragment). Since we have consistently used the prehybridization, hybridization and wash protocols described on page 33-34 we have used the temperature of the hybridization and subsequent washes as the main criteria for stringency. Hybridization and wash temperatures are typically about 3 to about 5° C. below the duplex melting temperature ($T_m$), where $T_m$ is the temperature at which 50% of the total number of possible duplexes are annealed under standardized conditions: It is understood that the $T_m$ is dependent upon the salt concentrations used and that changes in the hybridization and wash buffers could dramatically change the hybridization and wash temperatures needed to ensure species specificity.

TABLE 1

Similarity Matrix for Avian Eimeria (full length sequences)

| Species | Ea | Eb | Emx | Emt | En | Ep | Et |
|---|---|---|---|---|---|---|---|
| Acervulina | — | | | | | | |
| Brunetti | 97.8 | — | | | | | |
| Maxima | 96.9 | 97.1 | — | | | | |
| Mitis | 97.7 | 97.2 | 96.3 | — | | | |
| Necatrix | 97.4 | 96.5 | 95.5 | 96.5 | — | | |
| Praecox | 98.5 | 97.9 | 97.5 | 97.5 | 97.5 | — | |
| Tenella | 97.5 | 96.5 | 96.1 | 96.4 | 99.3 | 97.4 | — |

Table 2 illustrates examples of divergent segment probes useful for the specific identification of Eimeria. The probes listed in Table 3 derive from areas of nucleotide sequence within the small subunit ribosomal RNA genes which diverge among species and so, using appropriate hybridization and wash conditions (i.e., high stringency), are species-specific. Minor changes in the sequence of these probes (e.g.: deletion or addition of nucleotides from the ends), will not necessarily eliminate the species-specific feature especially if subtle changes in the hybridization temperature ($T_H$) are similarly incorporated as per the following equations:
$T_h = T_m - 5°$ C. $= 2°$ C.(A-T bp)$+4°$ C.(G-C bp)$-5°$ C. (Suggs et al., In D. D. Brown (ed.), ICN-UCLA Symp. Dev. Biol. Using Purified Genes. Academic Press, Inc. N.Y. Vol. 23, pp. 683–693 [1981]) and $Tm = \Delta H/(\Delta S + R \times \ln(C/4)) - 273.15°$ C. (Freier et al., Proc. Natl. Acad. Sci. USA 83: 9373-9377[1986]). It is understood that the invention will also include oligonucleotides which are inverse complements of the sequences in Table 1. The inverse sequences represent perfectly satisfactory species-specific hybridization probes against DNA targets.

The following general PCR amplification oligonucleotide priomers were chosen for *E. brunetti*:

5'-AAACTTAAAGGAATTGACGG-3'    ERIB 7
SEQ ID NO:44

5'-CGGTGTGTACAAAGGGCAGG-3'    ERIB 8
SEQ ID NO:45

Each of these oligonucleotides is derived from conserved domains of ssrRNA genes and accordingly, are general PCR amplification primers. The primers span a length of approximately 508 nucleotides corresponding to nucleotide position 1240 to 1748 in the full length *E. brunetti* sequence (see FIG. 2B). These two oligonucleotides were used as primers in a PCR reaction which targeted *E. brunetti* genomic DNA as the amplification substrate using conditions described earlier for the full length products. The resulting PCR reaction product was cloned into the bacterial plasmid vector pUC120 as described above. Bacterial clones harboring recombinant plasmids with the appropriate size insert were identified and two of these were sequenced using the Sanger chain termination method as described above. The nucleotide sequence of these clones was identical and is entered as Table 2 entitled *E. brunetti* fragment 4. The nucleotide sequence for the *E. brunetti* specific hybridization probe pEb4e-rc (SEQ ID NO:36) is complementary to nucleotide positions 224 to 244 in *E. brunetti* fragment 4, Table 2.

TABLE 2

*Eimeria brunetti* fragment 4

| | | | | |
|---|---|---|---|---|
| AAACTTAAAG | GAATTGACGG | AGGGGCACCA | CCAGGCGTGG | 40 |
| AGCCTGCGGC | TTAATTTGAC | TCAACACGGG | GAAACTCACC | 80 |
| AGGTCCAGAC | ATGGGAAGGA | TTGACAGATT | GATAGCTCTT | 120 |
| TCTTGATTCT | ATGGGTGGTG | GTGCATGGCC | GTTCTTAGTT | 160 |
| GGTGGAGTGA | TCTGTCTGGT | TAATTTCGAT | AACGAACGAG | 200 |
| ACCTTGGCCT | GCTAAATAGG | GTCGGTGACT | TTGGTTACCG | 240 |
| TATCGCTTCT | TAGAGGGACT | TTGCGTGTCT | AACGCAAGGA | 280 |
| AGTTTGAGGC | AATAACAGGT | CTGTGATGCC | CTTAGATGTT | 320 |
| CTGGGCTGCA | CGCGCGCTAC | ACTGATGCAT | GCAACGAGTT | 360 |
| TTTACCTTGA | CCGACGGGGC | TGGGTAATCT | TGTGAGGGTG | 400 |
| CATCGTGATG | GGGATAGATT | ATTGCAATTA | TTAGTCTTCA | 440 |
| ACGAGGAATG | CCTAGTAGGC | GCAAGTCAGC | ACTTGCGCCG | 480 |
| ATTACGTCCC | TGCCCTTTGT | ACACACCG | | 508 |
| (SEQ ID NO:50) | | | | |

Live coccidiosis vaccines are produced using oocysts from attenuated strains of Eimeria. An example can include, but is not limited to, seven or more avian Eimeria species such as: *E. acervulina, E. tenella, E. maxima, E. necatrix, E. praecox, E. mitis, E. brunetti.* An immunogenic dose of oocysts from each species is combined, beaded in wax and covered with gypsum. An immunogenic dose refers to a dosage of each species which in combination prevents coccidiosis induced by one or more species. One day old female SPF Leghorn chicks are housed in isolator cages and given non-vaccine containing feed and water *ad libitum* until two weeks of age. Feed is removed on the day prior to administration of the vaccine. Vaccine beads are weighed and aliquots equivalent to 0.25 times, 0.5 times, 1 times, 2 times, 3 times, 5 times and 10 times the vaccine dose are mixed with feed (15 g/chick) and presented to the chicks in groups of from between about eight to about fifteen animals. All vaccine should be consumed within four hours. After the vaccine is fully consumed, vaccine-free feed is administered. A group of about 8 to 10 untreated birds are fed regular feed and water *ad libitum* for the duration of the experimental regimen. One to 3 additional groups of about 8 to about 15 birds is dosed by gavage with the the same number of unencapsulated oocysts (1X, 3X and 10X) and fed vaccine free feed *ad libitum.* These birds will represent a positive control for infection as well as serving to check the viability of organisms following encapsulation since the unencapsulated oocysts will be from the same production batch as those in the vaccine. Three to five days following administration of the vaccine or unencapsulated oocysts, intestinal epithelial and mucosal scrapings are prepared from the intestinal walls of the birds. Total nucleic acids extracted from these scrapings serve as the target or template in this protocol. The relative infectivity of each species of Eimeria subsequent to the encapsulation process is estimated based upon the ability to detect an amplification of the number of input oocysts. This is accomplished using species-specific $^{32}$P-labeled oligonucleotide hybridization probes. Some of the birds in each treatment group are sacrificed and used for fecal oocyst counts from days four to seven post-infection. Quantitation is based on a standard curve using genomic DNA prepared from cloned vaccine strain oocysts.

Preparation of total nucleic acids is carried out with the following method. It is important to take precautions not to introduce nucleases into the process, e.g. when possible use baked glassware or use plastic and autoclaved solutions where appropriate. Chickens are sacrificed 3–5 days after receiving a vaccine dose. The intestine and the ceca are removed, cut along their length and rinsed with tap water. The interior wall of the intestine and ceca are scraped/stripped with a microscope slide. Scrapings are transferred to a 50 ml centrifuge tube containing about 5 to 10 ml of 2X Proteinase K digestion buffer (about 400 mM Tris-HCl, pH 7.6, about 100 mM EDTA, about 1.0% SDS). The suspension is mixed vigorously on a vortex mixer. About 200 µl of about 5 mg/ml Proteinase K is added to the suspension and it is allowed to digest at about 55° C. for about 3 hours. If viscosity is a problem at this point, add about another 5 ml of digestion buffer. Add about 100 µl of 5 mg/ml Proteinase K and continue digestion overnight. Following the overnight digestion, about 100 µl of 5 mg/ml Proteinase K is added and digestion is continued for up to 24 hours. Remove about 600 µl of the digest to a 1.5 ml microfuge tube and extract about twice with about a 1:1 mix of buffer equilibrated phenol and chloroform. Then extract with about a 24:1 mix of chloroform and isoamyl alcohol. The final aqueous phase may be stored at −20° C. An aliquot of the final aqueous phase is ethanol precipitated. In most cases about 200 µl of the final aqueous phase is added to about 20 µl of 3 M sodium acetate (pH 4.6) and then combined with about 500 µl of ethanol. The samples are mixed by inversion and placed in a dry ice ethanol bath for about 20 minutes. The genomic DNA is then collected by centrifugation in an Eppendorf microcentrifuge for about 15 minutes. The precipitate is washed once with about 70% ethanol and dried in a Speed-Vac. The precipitate is suspended in about 200 µl of deionized water. The amount of DNA in this total nucleic acid preparation is estimated using bisbenzimide which is a fluorochrome whose properties change when bound to DNA as discussed before. Salmon testes DNA standards from 0 to 20 µg/100 µl TE are made from a stock solution. Prepare the dilutions in 12×75 mm borosilicate tubes using sterile tips; change tips between dilutions. Similarly, make 1:10 dilutions to a final volume of about 100 µl for each experimental sample in duplicate. A bisbenzimide dye stock at a concentration of about 200 µg per ml in sterile water and stored at 4° C. in a dark bottle is stable for up to 6 months. Prior to use, dilute the dye stock 1:200 with a buffer whose composition is about 50 mM sodium phosphate, pH 7.6, 2 M NaCl. Add about 2 ml of this to each borosilicate tube with an Eppendorf repeater pipette, mix and measure directly in a fluorocolorimeter at an excitation wavelength of 356 nm and an emission wavelength of 458 nm. Determine the amount of DNA in the experimental samples after calibrating the machine with standards.

PCR amplification of ssrRNA sequences from genomic DNA prepared from chicken intestinal mucosal scrapings is carried out in the following manner. Due to the exquisite sensitivity of this technique, extreme caution must be exercised to avoid contamination. Dedicated pipettes, pipette tips, vessels and stock solutions for DNA preparation, reaction assembly and sample analysis are recommended. Ideally, this should be done in areas separate from other DNA handling.. About 200 ng of experimental genomic DNA based upon the bisbenzimide assay above is used as the starting target material. It is critical that this material first be ethanol precipitated to remove solvents remaining from the extractions which inhibit the Taq DNA polymerase. Genomic DNA prepared from known numbers of purified organisms from each of the species of Eimeria are used to "spike" about 200 ng of chicken hepatic genomic DNA. These will serve as amplification standards and hybridization specificity standards. Prepare a daily working solution of Tris-HCl buffered (pH 7.6) deoxynucleoside triphosphates dATP, dCTP, dGTP and dGTP each at about 1.25 mM from about 100 mM stocks stored at $-20°$ C. Prepare a 10X reaction buffer composed of about 100 mM Tris- HCl, pH 8.3, about 500 mM KCl, about 15 mM $MgCl_2$, about 0.01% gelatin and autoclave. This is aliquoted and stored at about $-20°$ C. The reaction mixture is assembled in dedicated PCR reaction tubes in a final volume of about 100 $\mu$l. First, a reaction mixture cocktail is prepared by mixing the following components at these final concentrations in this specific order: water, dATP, dCTP, dGTP and dTTP (dNTPs each at about 200 $\mu$M), 1X reaction buffer, and about 1 $\mu$M of each of the two amplification primers (ERIB I and ERIB 2) (SEQ ID NO:I and SEQ ID NO:3) or any other suitable primers which flank a non-consensus region, mix, and add about 1.25 U Taq DNA polymerase per reaction tube and invert to mix. Other primers include, but are not limited to:

ERIB 2 TCCCTCTCCGGAATCGGAC
(SEQ ID NO:3)

5 ERIB CCAGGTCCAGACATGG
(SEQ ID NO:4)

3 ERIB CTTGCGCCTACTAGGC
(SEQ ID NO:5)

5AERIB GTCGCAAGGCTGAAAC
(SEQ ID NO:31)

3AERIB CTTGCGCCTACTAGGC
(SEQ ID NO:32)

5BERIB GGGGGGAGTATGGTCTGCAAGGC
(SEQ ID NO:33)

3BERIB GCATGCATCAGTGTAGCTGCGCG
(SEQ ID NO:34)

Primer ERIB 1 (SEQ ID NO:1) is used with primer ERIB 2 (SEQ ID NO:2) and primer 5 ERIB (SEQ ID NO:4) is used with primer 3 ERIB (SEQ ID NO:5). Primer 5AERIB (SEQ ID NO:31) is preferably used with primer 3AERIB (SEQ ID NO:32) and primer 5BERIB (SEQ ID N0:33) is preferably used with primer 3BERIB (SEQ ID N0:34), however, any primer begining with 5' could also be used with any primer begining with 3'. An aliquot of about 80 $\mu$l of the cocktail is then distributed to each reaction tube. Based on the bisbenzimide DNA assay described above, about 200 ng of experimental genomic DNA is adjusted to a final volume of about 20 $\mu$l with distilled water and added to the reaction mixture. When amplifying using primers ERIB1 (SEQ ID NO: 1) and ERIB2 (SEQ ID NO:3), the reactions are run in the BIOS thermal cycler. Generally the BIOS thermal cycler will be programmed as follows:

a) about 3 cycles consisting of about 94° C. for about 1 minute to denature, about 50° C. for about 30 seconds to anneal and about 72° C. for about 45 seconds for polymerization;

b) about 27 cycles consisting of about 94° C. for about 20 seconds to denature, about 50° C. for about 30 seconds to anneal and about 72° C. for about 45 seconds for polymerization;

c) about one cycle at about 72° C. for about 10 minutes. When amplifying using primer pairs 5AERIB/3AERIB (SEQ ID NO:31)/(SEQ ID NO:32) and 5BERIB/3BERIB (SEQ ID NO:33 )/(SEQ ID NO:34), the reactions are run in the Perkin Elmer Cetus DNA thermal cycler. The reactions are set up as described above for the primer pair ERIB1/ERIB2 (SEQ ID NO:I)/(SEQ ID NO:3), except that after addition of the experimental genomic DNA, the reaction is overlayed with approximately 50 $\mu$l of light mineral oil and then placed into the Perkin Elmer Cetus DNA thermal cycler programmed as follows:

a) about 3 cycles consisting of about 94° C. for about 1 minute to denature, about 48° C. for about 1 minute to anneal and about 72° C. for about 1 minute for polymerization;

b) about 32 cycles consisting of about 94° C. for about 1 minute to denature, about 50° C. for about 1 minute 30 seconds to anneal and bout 72° C. for about 2 minutes for polymerization;

c) about one cycle at about 72° C. for about 10 minutes. About 5 $\mu$l of the reaction product is then assayed for DNA content using a small scale bisbenzimide assay analogous to that described above. Exceptions are that dilutions are done in microcentrifuge tubes in duplicate, the final assay volume is about 500 $\mu$l, the sample is read in a microcell and the standard curve is linear from about 5 to 200 ng/ml.

Generally, about 100 ng of the PCR product quantitated as described above and adjusted to a final volume of about 100 $\mu$l with water, is applied to Nytran sheets (prewetted in water) in a slot-blot or dot-blot manifold as described in the manufacturer's specifications (Schleicher and Schuell, Inc.). To each sample is added 1 volume of 1 M NaOH. The samples are then incubated at about room temperature for about 5 minutes to denature the DNA and neutralized by adding about 1 volume of 1 M Tris-HCl (pH 7.3). A vacuum is then applied to the apparatus to filter the samples. Each sample is then rinsed with about 500 $\mu$l of 4 M ammonium acetate (pH 6.8). Genomic DNA prepared from purified organisms of each of the avian Eimeria species is PCR amplified as described previously and is used to "spike" chicken hepatic genomic DNA also PCR amplified as described previously. The spiked DNA is also applied to the filters to serve as a species-specific quantitation standard. Appropriate buffer controls and blank controls are routinely included. Air dry the filters and bake under vacuum at about 80° C. for about 2 hours.

Oligonucleotide hybridization probes are labeled for quantitative determination of parasite viability. The preferred method is to end label the oligonucleotides with gamma $^{32}$P-ATP. Other methods known in the art can also be used. Quantitate and standardize oligonucleotides (1 mg/ml=25 $A_{260}$). Add about 5-10 pmoles of oligonucleotide to at least a two fold molar excess of gamma $^{32}$P-ATP (specific activity >5000 Ci/mmol), about 5 μl of 10X kinase buffer(about 0.5 Tris-HCl, about pH 7.6, about 0.1 M MgCl$_2$, about 50 mM DTT, about 1 mM spermidine, about 1 mM EDTA) and a quantity of water sufficient to achieve a 50 μl reaction volume following the addition of 20 U of polynucleotide kinase. Incubate the mixture for about 30 minutes at about 37° C. Stop the reaction by the addition of about 4 μl of 0.5 M EDTA, about 46 μl of TE. Extract once with a 1:1 mixture of buffer equilibrated phenol and chloroform. Pass the aqueous phase through a Stratagene push column (Stratagene) as per the manufacturer's specifications to remove the unincorporated isotope from the labeled oligonucleotide.

Prehybridization, hybridization and washes are carried out in the following manner. Prehybridization is done in a buffer whose composition is about 6X SSPE, 1% SDS, 10X Denhardt's, about 20 to 100 μg per ml tRNA, and either with or without 50 μg per ml denatured salmon sperm DNA. SSPE consists of about 180 mM NaCl, 10 mM NaH$_2$PO$_4$, 1 mM EDTA. The buffer is made and kept at 42° C. until ready for use to keep the SDS in solution. The dry sheet(s) of Nytran are prewetted in 6X SSPE, placed in a polyethylene freezer bag which is heat sealed on three sides. The heterologous DNA is denatured in a boiling water bath for 10 minutes, quick chilled on ice and mixed with the prehybridization solution (20–40 ml depending on the number of sheets of Nytran in the bag). The prehybridization solution is added to the bag, air bubbles removed, and the bag is sealed on the fourth edge. The bag is then secured to a glass plate with elastic bands and submerged in a water bath at 42° C. for at least 3 hours or for as long as overnight. Following prehybridization the bag is cut open and the buffer is removed completely. The hybridization buffer is about 6X SSPE plus about 1% SDS. Hybridization is done at or about the $T_h$ of the desired hybrid. For probes less than 25 nucleotides in length, hybridization conditions are determined using either of the following formulae:

$T_h = T_m - 5°$ C. $= 2°$ C.(A-T bp)$+4°$ C.(G-C bp) $-5°$ C. (Suggs et al., In D. D. Brown (ed.), ICN-UCLA Syrup. Dev. Biol. Using Purified Genes. Academic Press, Inc. N.Y. Vol. 23, pp. 683–693 [1981])

$Tm = \Delta H/(\Delta S + R \times \ln(C/4)) - 273.15°$ C. (Freier et al., Proc. Natl. Acad. Sci. USA 83: 9373–9377[1986]). The end labeled oligonucleotide probe is warmed at 68° C. for 5 min prior to mixing with 10–20 ml (depending on the number of filters per bag; approx. 1–5×10$^6$ dpm/ml) of hybridization buffer which is prewarmed at the $T_h$. This is poured into the bag, air bubbles are removed and the bag is resealed. The bag is secured to a glass plate and submerged in a water bath at the $T_h$ for at least 12 hours to overnight. Following hybridization, cut open the bag and discard the buffer. Cut the remaining three sides of the bag and with forceps remove the filter(s) to a pyrex dish containing the first wash solution. The washes are as follows:
   a) about 3 times for 5–10 minutes each in 6X SSPE, 1% SDS at 37° C. with shaking;
   b) about one time for 3 min in 1X SSPE, 1% SDS at the Th of the hybrid;
   c) about 3–4 times for approx. 5 min each in 6X SSPE at room temperature with shaking to remove the SDS.

Wash volumes should be at least 100 ml to cover the filters; use more with multiple filters. All wash solutions should be prewarmed at the respective temperatures prior to use. Air dry the filters, place in a cassette which contains two intensifying screens and expose to X-ray film at −70° C. Develop the film after 1–3 days.

Quantitation of hybridization signal is carried out using the Molecular Dynamics PhosphorImager (Molecular Dynamics). Dried blots are placed beneath plastic wrap in the PhosphorImager cassette as per the manufacturer's instructions and exposed to the phosphor screen for approximately 2 hours for the common hybridization probe and 3–12 hours for the specific Eimeria probes. The screen is then scanned with a laser which releases the energy captured by the phosphor in the screen. The released energy is quantitated by the machine.

Eimeria RNA can also be isolated and used to determine the presence and concentration of multiple species of Eimeria in a sample. Isolation of Eimeria RNA from chicken intestines must be carried out with care to avoid degradation of the RNA. One successful protocol is essentially the same as published in Chirgwin et al., Biochemistry 18 (1979) 5294–5299. Mucosal scrapings from chickens vaccinated 3–5 days previously are taken and transferred to a 50 ml centrifuge tube as is described earlier. These scrapings are immediately placed into about 24 ml of about 4 M guanidine thiocyanate, pH 7.0, about 0.5% sodium N-lauroylsarcosine, about 25 mM sodium citrate, about 0.1 M 2-mercaptoethanol, and about 0.1% Sigma 30% Antifoam A. The samples are quickly homogenized with a Polytron (Brinkmann) at full speed three times for 20 seconds; between samples the Polytron is rinsed 2 times with sterile distilled water. The samples are then centrifuged at approximately 8,000 RPM for 10 minutes at about 10° C. in a swinging bucket rotor e.g. JS-13 (Beckman). The supernatants are decanted and the pellets are precipitated with about 0.6 ml of about 1 M acetic acid and about 18 ml of 100% ethanol at −20° C., overnight. The samples are centrifuged again at 8,000 RPM, for 10 minutes at 10° C. The pellets are resuspended in about 12 ml of approximately 7.5 M guanidine hydrochloride, pH 7.0, 25 mM sodium citrate, and 5 mM dithiothreitol, shaken vigorously, and heated to 68° C. until dissolved. The samples are precipitated with approximately 0.3 ml of 1 M acetic acid and about 6 ml of 100% ethanol at −20° C., overnight. Again the samples are centrifuged, resuspended, and precipitated as before, except with one-half the previous volumes, i.e. 6 ml, 0.15 ml, and 3 ml respectively. The samples are pelleted once again, triturated with about 10 ml of room-temperature 95% ethanol, transferred to baked Corex centrifuge tubes, and repelleted at about 10,000 RPM for about 30 minutes at about 10° C. The RNA pellets are dried under vacuum in a Speed-Vac (Savant Instruments), dissolved at about 68° C. in about 2 ml diethyl pyrocarbonate-treated sterile distilled water, repelleted, reextracted with about 1 ml diethyl pyrocarbonate-treated sterile distilled water, and repelleted again. The extractions are reprecipitated with about 300 μl of 2 M potassium acetate, about pH 5.0, and about 8 ml of 100% ethanol at −20° C. overnight. The final RNA preparations are pelleted and resuspended in about 1 ml of diethyl pyrocarbonate-treated sterile water. Absorbance readings at 260 nm and 280 nm (Beckman spectrophotometer) are taken to determine RNA concentrations; about 3 μg of RNA are then subjected to electrophoresis on about a 1.2% agarose gel to check the RNA quality, size, and relative concentration. RNA samples can be stored at −70° C. The RNA is treated with DNase which is free of RNase (i.e. RQ1 DNase, Promega) as per manufacturers directions, except digestion is carried out for about 30–40 minutes at about 37° C. The sample is extracted with about equal volumes of phenol/chloroform and precipitated with about 1/10 volume of about 3 M sodium acetate and about 2 ½ volumes of ethanol at about −70° C. overnight. The RNA pellet is recovered by centrifugation, washed with about 75% ethanol, dried under vacuum and resuspended in diethyl pyrocarbonate-treated sterile water. Twenty to thirty micrograms of RNA are slotted in duplicate onto Nytran filters after denaturing the RNA in 1X denaturing solution (4X denaturing solution contains about 1 ml of formaldehyde, 56 μl of 1 M sodium phosphate, pH 6.5, and 344 μl of sterile distilled water) at 68° C. for about 20 minutes. The denatured samples are immediately placed on ice to cool and then immobilized onto Nytran filters with a slot/dot-blot manifold as per manufacturers directions (BioRad Laboratories, Inc.). The nylon filters are baked at about 80° C. for about 30 to 60 minutes. These filters are then prehybridized, hybridized and washed as per manufacturers specifications (Schliecher and Schuell, Inc.) for oligonucleotide probes for Northern (RNA) transfers. The oligonucleotide probes are 32p end labelled as previously described.

Genomic DNA from fecal oocysts can also be isolated and used to determine the presence and concentration of multiple species of Eimeria in a sample. The feces is diluted about ten fold in distilled water and then the contents are passed through a sieving device. A series of passes through screens of decreasing size functionally removes a considerable amount of fecal debris. Partially pure oocyst fractions of the Eimeria species are then collected by flotation in about 2.2 M sucrose (Jackson, Parasitel. 54:87–93 [1964]), and further treated by incubation in sodium hypochlorite at a concentration of 5.25%, in water at about 40° C. for about 10 minutes. The sodium hypochlorite is removed by several washes in sterile phosphate buffered saline (PBS) at about pH 7.6 to obtain purified, sterile oocysts. Depending upon the species, oocysts are allowed to sporulate in a shaking water bath for about 24 to about 60 hours at about 20° C. (Edgar,Trans. Am. Micr. Soc. 62:237–242 [1954]) in PBS or sterile water. Following sporulation, oocysts are washed several times in sterile PBS.

Sporulated oocysts are disrupted by shaking with 3 mm sterile glass beads. Beads are added to the oocyst suspension and the mixture is mixed vigorously on a Vortex mixer for about 2 minutes. Periodically the extent of breakage is assessed microscopically. When approximately 50% breakage has occurred, the glass beads are allowed to settle and the sample above the beads is removed and mixed with an equal volume of Percoil (Pharmacia). The disrupted oocysts are subjected to centrifugation at about 2,000 x g for about 10 rain at about 4° C. to pellet the enriched sporocyst fraction. Unbroken oocysts form a layer on top of the 50% Percoll and are removed, washed in PBS, mixed with glass beads and mixed again as described above. This procedure is performed repeatedly (3–4 times) until very few unbroken oocysts remain following Percoil fractionation. Sporocyst pellets are combined and washed several times in PBS.

Sporocysts are then diluted in 0.01 M Tris (pH 8.0), 0.2 M NaCl to a concentration of approximately $10^8$ per ml and the suspension is adjusted to about 1% sodium dodecyl sulfate (SDS) and about 10 mM EDTA which results in membrane lysis. The released genomic DNA is solubilized by digestion with Proteinase K (150 μg/ml) for approximately 30 minutes at about 55 to 65° C. Genomic DNA is extracted twice with buffer equilibrated phenol (about pH 7.6), twice with a mixture of phenol/chloroform/isoamyl alcohol at about 25:24:1, and twice with chloroform/isoamyl alcohol at about 24:1. The final aqueous phase is dialyzed overnight in 10 mM Tris (pH 8.0), 10 mM NaCl, 10 mM EDTA (pH 8.0). RNA which has co-purified with the DNA is selectively removed from the dialysate by digestion with heat inactivated RNase A used at a concentration of about 150 μg/ml. The samples are incubated for about 1 hour at about 370 C. The RNase and other residual proteins are removed by a secondary digestion with Proteinase K (about 150 μg/ml, for about 30 minutes at about 37° C.). The genomic DNA is then successively extracted with organic solvents as described above. The final aqueous phase is precipitated with about 0.1 volumes of about 3 M sodium acetate and about 2.5 volumes of about 100% ethanol. Glycogen is added to 20 μg/ml to act as carrier. The pellets are washed twice with about 70% ethanol. The genomic DNA pellet is air dried by inversion and is then suspended in about 10 mM Tris. HCl (pH 7.6), 1 mM EDTA buffer (TE) or distilled water at a concentration of about $5-8 \times 10^8$ sporocyst equivalents/ml and quantitated by absorbance at 260 nm and/or using the afformentioned bisbenzimide assay. An aliquot of DNA is then analyzed by agarose gel electrophoresis to confirm; (i) the spectrophotometric generated concentration, (ii) the lack of residual RNA, and (iii) it's high molecular weight integrity.

Equivalent amounts of genomic DNA based on the bisbenzimide assay are denatured and immobilized on eight identical sheets of Nytran paper for hybridization. Generally, about 100 ng of the genomic DNA quantitated as described above is adjusted to about 100 μl with water, to which is added about 0.1 volume of about 3 M NaOH. This is incubated at about 70° C. for about 30–60 minutes to denature the DNA, cooled at room temperature, neutralized by adding about 1 volume of about 2 M ammonium acetate (pH 7.0) and applied to Nytran sheets in a slot-blot or dot-blot manifold as per the manufacture's specifications (Schliecher and Schuell, Inc.). A vacuum is applied to filter the samples. Genomic DNA prepared from known numbers of purified organisms from each of the species of Eimeria is also applied to the filters to serve as a species-specific quantitation standard. Appropriate buffer controls and blank controls are routinely included. The filters are air dried and baked under vacuum at about 80° C. for about 2 hours. The prehybridization, oligonucleotide hybridization, washes and the quantitation of hybridization is carried out as described above.

The following examples illustrate the invention without, however, limiting the same thereto.

EXAMPLE 1

Method For Cloning Eimeria Species Small Subunit Ribosomal RNA Genes

Oocysts from laboratory strains of E. acervulina, E. brunetti, E. maxims, E. mitis, E. necatrix, E. praecox and E. tenella were propagated by oral infection of broiler chickens. Eimeria tenella oocysts were isolated from the cecal contents of chickens at 5–7 days post-infection. The remaining Eimeria species were individually isolated from fecal collections 3-8 days following infection. The cecal contents were physically disrupted in a Waring Blender, in distilled water and digested with pepsin. Following digestion, debris was removed by centrifugation in distilled water. The feces was diluted ten fold in distilled water and then the contents were passed through a sieving device. A series of passes through screens of decreasing size functionally removed a considerable amount of fecal debris. Partially pure oocyst fractions for each of the seven Eimeria species were then collected by flotation in 2.2 M sucrose (Jackson, Parasitol. 54:87–93 [1964]), and further treated by incubation in sodium hypochlorite at a concentration of 5.25% in water at 40° C. for 10 minutes. The sodium hypochlorite was removed by several washes in sterile phosphate buffered saline (PBS) at pH 7.6 to obtain purified, sterile oocysts. Depending upon the species, oocysts were allowed to sporulate in a shaking water bath for 24 to 60 hours at 20° C. (Edgar,-Trans. Am. Micr. Soc. 62:237–242 [1954]) in PBS or sterile water. Following sporulation, the oocysts were washed several times in sterile PBS.

Sporulated oocysts were disrupted using 3 mm sterile glass beads. Beads were added to the oocyst suspension and the mixture was mixed vigorously on a Vortex mixer for approximately 2 minutes. Periodically the extent of breakage was assessed microscopically. When approximately 50% of the sporulated oocysts were disrupted, the glass beads were allowed to settle and the sample above the beads was removed and mixed with an equal volume of Percoil (Pharmacia). The disrupted oocysts were subjected to centrifugation at 2,000 x g for 10 min at 4° C. to pellet the enriched sporocyst fraction. Unbroken oocysts forming a layer on top of the 50% Percoil were removed, washed in PBS, mixed with glass beads and mixed again as described above. This procedure was performed repeatedly (3-4 times) until very few unbroken oocysts remained following Percoil fractionation. Sporocyst pellets were combined and washed several times in PBS.

Sporocysts were then diluted in 0.01 M Tris (pH 8.0), 0.2 M NaCl to a concentration of approximately $10^8$ per ml and the suspension was adjusted to 1% sodium dodecyl sulfate (SDS) and 10 mM EDTA which resulted in membrane lysis. The released genomic DNA was solubilized by digestion with Proteinase K (150 µg/ml) for approximately 30 minutes at 65° C. Genomic DNA was extracted twice with buffer equilibrated phenol (pH 7.6), twice with a mixture of phenol/chloroform/isoamyl alcohol at 25:24:1, and twice with chloroform/isoamyl alcohol at 24:1. The final aqueous phase was dialyzed overnight in 10 mM Tris (pH 8.0), 10 mM NaCl, 10 mM EDTA (pH 8.0). RNA which had co-purified with the DNA was selectively removed from the dialysate by digestion with heat inactivated RNase A used at a concentration of 150 µg/ml. The samples were incubated for 1 hour at 37° C. The RNase and other residual proteins were removed by a secondary digestion with Proteinase K (150 µg/ml, for 30 minutes at 55° C.). The genomic DNA was then successively extracted with organic solvents as described above. The final aqueous phase was precipitated with 0.1 volume of 3 M sodium acetate and 2.5 volumes of 100% ethanol. Glycogen was added to 20 µg/ml to act as carrier. The pellets were washed twice with 70% ethanol. The genomic DNA pellet was air dried by inversion and was then suspended in 10 mM Tris. HCl (pH 7.6), I mM EDTA buffer (TE) or distilled water at a concentration of $5-8 \times 10^8$ sporocyst equivalents/ml and quantitated by absorbance at 260 nm. An aliquot of DNA was then analyzed by agarose gel electrophoresis to confirm (i) the spectrophotometric generated concentration, (ii) the lack of residual RNA, and (iii) its high molecular weight integrity.

The ribosomal RNA (rRNA) gene loci harbor a wealth of information that has been successfully used to establish phylogenetic relationships among and within eukaryotic kingdoms (Hasegawa et al., J. Mol. Evol. 22:32–80 [1985]). Sequences of the ssrRNA from a number of highly divergent organisms have recently been compiled (Dams et al., Nucleic Acids Res. 16S: r87–r173 [1988], Neefs et al., Nucleic Acids Res. 18S: 2237–2317 [1990]). Comparative analysis of these nucleotide sequences revealed areas with dramatic sequence similarities and other areas that are characterized by considerable sequence drift. Regions dose to both the 5'- and 3'-ends of the consensus small subunit rRNA (ssrRNA) sequence with near identity in the eukaryotic kingdom were chosen. Oligonucleotides corresponding to these sequences were chosen:

| | |
|---|---|
| 5'-ACCTGGTTGATCCTGCCAG-3' SEQ ID NO:1 | ERIB 1 |
| 5'-CTTCCGCAGGTTCACCTACGG-3' SEQ ID NO:2 | ERIB 10 |

The oligonucleotides were synthesized using an Applied Biosystems 380B instrument and purified as per the manufacturer's recommendations. ERIB 1 (SEQ ID NO:1) represents a consensus sequence less than 10 nucleotides from the 5'-end of eukaryotic ssrRNA genes. ERIB 10 (SEQ ID NO:2) is the inverse complement to a consensus sequence located approximately 20 nucleotides from the 3'-end of eukaryotic ssrRNA genes. Taken together, these two oligonucleotides span the vast majority of the ssrRNA gene sequence.

ERIB 1 (SEQ ID NO:1) and ERIB 10 (SEQ ID NO:2) were used as a primer pair in the polymerase chain reaction (PCR, Saiki et al., Science 239:487–491 [1988]) with the intention of selectively amplifying the ssrRNA genes contained within the genomic DNA preparation of each of the seven Eimeria species as described above. Genomic DNA was quantitated using a fluorescent dye binding assay (Lebarca and Paigen, Anal. Biochem. 102:344–352 [1980]) and diluted to a final concentration of 2.5 ng/µl for use as the PCR template. A 10X reaction buffer consisting of 100 mM Tris-HCl (pH 8.3), 500 mM KCl, 15 mM $MgCl_2$, 0.01% gelatin was prepared as well as 100 mM stocks of Tris-HCl (pH 7.6) buffered dATP, dCTP, dGTP and dTTP. The reaction mixture was prepared by mixing the following components at these final concentrations in this specific order: water, dATP, dCTP, dGTP and dTTP (each at 200 µM), 1X reaction buffer, 1 µM of each of the two oligonucleotide primers (ERIB 1 and ERIB 10) (SEQ ID NO:1 AND SEQ ID NO:2), and 1.25 U Taq DNA polymerase. The reaction mixture was assembled in dedicated PCR reaction tubes by combining 90 µl of the reaction cocktail with 10 µl (25 ng) of genomic DNA. The reaction was overlayed with approximately 50 µl of light mineral oil and then placed into a Perkin Elmer Cetus DNA thermal cycler programmed as follows:

35 cycles each composed of (i) 94° C. for about 60 seconds to denature, (ii) 50° C. for about 90 seconds to anneal, and (iii) 72° C. for 120 seconds for polymerization;

1 cycle at 72° C. for 10 minutes for extension.

A 5 μl aliquot of the reaction product was subjected to agarose gel DNA electrophoresis in TAE buffer along with DNA size standards. A characteristic band approximately 1.8 kb in length, whose size is roughly predicted by analogy to other eukaryotic ssrRNA genes, suggested that ERIB 1 (SEQ ID NO:1) and ERIB 10 (SEQ ID NO:2) actually hybridized to the Eimeria ssrRNA genes and that Taq DNA polymerase synthesized a reaction product by extension from the 3'-ends of these primers.

By definition, the ends of the 1.8 kb PCR products correspond to the input oligonucleotides and should be blunt. However, Taq DNA polymerase is prone to adding single non-template-directed nucleotides, in particular dATP, to the 3'-end of duplex PCR products (J. M. Clarke, Nucleic Acids Res. 16: 677–9686 [1988]). In order to increase cloning efficiency, the ends of the PCR products were "polished" to blunt-ends by the action of the Klenow fragment of bacterial DNA polymerase. Reaction products were extracted once with phenol, once with a phenol/chloroform/isoamyl alcohol mix and once with chloroform/isoamyl alcohol as described earlier. DNA was precipitated with sodium acetate/ethanol and the pellet was washed twice with 70% ethanol. For the Klenow fragment reaction, the DNA (1–10 μg) was suspended in 15 μl of water and mixed with 2 μl of 10X nick translation buffer ( 0.5 M Tris.Cl [pH 7.2], 0.1 M MgSO$_4$, 1 mM dithiothreitol, 500 μg/ml bovine serum albumin [BSA Pentax Fraction V]), and 2 μl of a 1.25 mM solution of all four dNTPs and 1 μl (=5 Units) Klenow. The reaction was conducted at 14° C. for 1 hour and was terminated by heating at 65° C. for 10 minutes. The polished 1.8 kb DNA products were passed over a G 25 column, extracted once with phenol, and twice with chloroform/isoamyl alcohol as described earlier. The DNA was precipitated with sodium acetate/ethanol and the pellet was washed twice with 70% ethanol. The DNA was resuspended in 36 μl of water and mixed with 4 μl of 0.2 M Tris.HCl (pH 9.5), 10 mM spermidine, 1 mM EDTA. This reaction mixture was incubated at 70° C. for 5 minutes and subsequently rapidly chilled on ice. To the above 40 μl are added 5 μl of 10X blunt end kinase buffer (0.5 M Tris.Cl [pH 9.5), 0.1 M MgCl$_2$, 50 mM dithiothreitol, 50% glycerol), and 5 μl of a 10 mM solution of ATP and 2 μl (=20U) of T4 polynucleotide kinase. The reaction was conducted at 37° C. for 30 minutes and was terminated by the addition of 2 μl of 0.5 M EDTA. The reaction mixture was brought to about 100 μl with TE buffer and the reaction products were extracted once with phenol, once with phenol/chloroform/isoamyl alcohol mix and once with chloroform/isoamyl alcohol as described previously. DNA was precipitated with sodium acetate/ethanol and the pellet was washed twice with 70% ethanol, as above. The DNA is resuspended in 20 μl of water and quantitated by absorbance at 260 nm.

The polished 1.8 kb DNA products were then subjected to agarose gel electrophoresis to separate the residual oligonucleotide primers and nonspecific PCR products from the polished 1.8 kb products. Gel slices containing the bands of interest were excised, melted and the DNA eluted using Geneclean II (BIO 101 Inc., Vogelstein and Gillespie, Proc. Natl. Acad. Sci. USA 76:615–619 1979) as per the manufacturer's instructions. Eluted DNA products were then quantitated by absorbance at 260 nm.

A phagemid cloning vector pUC120 (Vieria, *Bireplicon Filamentous Phages and the Production of Single Stranded Plasmid DNA*. Ph.D. thesis, University of Minnesota [1989]) is cut at it's unique Sma I site in the polylinker. Other suitable cloning vectors include but are not limited to the pGEM-Zf series (Promega Corporation) and the pBluescript II series (Stratagene Cloning Systems). Cutting was monitored by analytical agarose gel electrophoresis. The linearized DNA was then extracted with organic solvents, precipitated and washed with 70% ethanol as described earlier. The 5'-end of each strand of the plasmid was phosphatased with calf intestinal phosphatase (CIP) to decrease the frequency of an autoligation event. This was accomplished by mixing the linearized plasmid (about 10 μg) with 5 μl of 10X CIP buffer (0.5 M Tris-HCl pH 9.0, 10 mM MgCl$_2$, 1 mM ZnCl$_2$, 10 mM spermidine) and 1 μl (1 Unit) of CIP in a final 50 μl reaction volume. The reaction was conducted for 15 minutes at 37° C. and then 15 minutes at 56° C. A second aliquot of CIP was then added and the reaction was repeated as above. The reaction was terminated by the addition of 40 μl of H20, 10 μl of 10X STE buffer (100 mM Tris-HCl, pH 8.0, 1 M NaCl, 10 mM EDTA), 2.5 μl of 20% SDS and heated at 68° C. for 15 minutes. The linearized, phosphatased vector was then extracted, precipitated and washed as above.

Ligation of the gel purified ssrRNA gene PCR products into the blunt Stoa I site within the pUC120 polylinker was then conducted. Approximately 100 ng of linearized vector was mixed with an equimolar amount of the respective PCR products in a 20 μl reaction mixture which, in addition is composed of 66 mM Tris-HCl, pH 7.6, 5 mM MgCl$_2$, 5 mM dithiothreitol, 1 mM ATP. The reaction was initiated by the addition of T4 DNA ligase and incubated for 12–16 hours at 14° C.

Competent bacterial cells capable of uptake of foreign DNA were prepared by the following method. A predetermined volume (about 2 ml per transformation reaction) of sterile 2X YT bacterial media (16 g bacto-tryptone, 10 g yeast extract, 5 g NaCl per liter) was inoculated with a single colony of Escherichia coli MV1184 and grown with vigorous mixing at 37° C. until it reached an optical density of 0.6 at 600 nm. Other suitable bacterial hosts include but are not limited to MN522, JM101, TB1 and XL1-Blue. Bacteria were collected by centrifugation at 1000 x g, at 4° C., for 5 minutes. The resulting cell pellet was gently suspended in one-half of the original culture volume with sterile 50 mM CaCl$_2$ and the suspension was then placed on ice for 20 min. The cells were again collected by centrifugation and then gently suspended in one-tenth volume of sterile 50 mM CaCl$_2$. The bacterial suspension was then kept at 4° C. for 16–24 hours.

From the 20 μl ligation reaction mixture 2 μl and 18 μl aliquots were dispensed into sterile polypropylene tubes. Approximately 100 μl of competent bacteria were added to each of the tubes containing the ligation reactions (as well as the appropriate ligation and transformation controls) and these were placed on ice for 40 minutes. After this, the bacteria were "heat-shocked" by incubation at 42° C. for 90 seconds and then allowed to recover for approximately 5 minutes at room temperature. Each transformation tube was then plated onto a 2X YT agar plate which contains ampicillin at a concentration of 50 mg/l for the selection of bacteria harboring plasmids and for plasmid maintenance. Plates were incubated in an inverted position overnight at 37° C.

Bacterial clones harboring plasmids were identified by their ability to grow on plates in the presence of ampicillin. Single colonies were used to inoculate 5 ml of 2X YT/AMP (i.e., 2X YT media containing ampicillin at 50 mg/l) and these cultures were grown overnight at 37° C. with vigorous shaking. Approximately 1.5 ml of the culture was poured off into an Eppendorf tube and collected by centrifugation in an Eppendorf centrifuge for at least 1 minute; the remainder of the culture was stored at 4° C. and served as a genetic stock. The media above the bacterial pellet was aspirated off and the pellet was suspended by vortexing in 100 µl of a cold, freshly prepared solution of 50 mM glucose, 10 mM EDTA, 25 mM Tris-HCl (pH 8.0), 4 mg/ml lysozyme. This mixture was incubated at room temperature for 5 minutes. Then 200 µl of a cold, freshly prepared solution composed of 0.2 N NaOH, 1% SDS was added to each tube, mixed gently by inversion, and put on ice for 5 minutes. To this mixture was added 150 µl of a cold, freshly prepared solution containing 6 ml of 5 M potassium acetate, 1.15 ml of glacial acetic acid, 2.85 ml distilled water. The contents were gently vortexed and this mixture was stored on ice for 5 minutes. The cellular debris was collected by centrifugation in an Eppendorf centrifuge for 10 minutes at 4° C. and the supernatant fluid was extracted one time with phenol/chloroform/isoamyl alcohol (25:24:1). Plasmid DNA and cellular RNA were precipitated from the final aqueous phase with the addition of two volumes of 100% ethanol at room temperature. A pellet was collected by centrifugation for 5 minutes at room temperature, the pellet was washed one time with 70% ethanol and then dried briefly. The nucleic acid pellet was then suspended in 50 µl of TE containing 20 µg of DNase-free RNase per ml and incubated for 15–30 minutes at 37° C. to quantitatively eliminate cellular RNA. Aliquots of 10 µl were then cut to completion with Hind III and Eco R1 (each at approximately 20 units) in a buffer composed of 50 mM NaCl, 100 mM Tris-HCl (pH 7.5), 5 mM $MgCl_2$ at 37° C. for 60 min. The restriction enzyme reaction products were separated by agarose gel electrophoresis to identify those plasmids which contained the appropriate inserts. Those recombinant plasmids which contained the predicted 1.8 kb insert were then cut with a second restriction enzyme (usually Pst I) to verify; (i) that only a single copy of the insert was contained within the plasmid, and (ii) to score for orientation of the insert DNA with respect to the bacterial promoter. This was accomplished by removing a second 10 µl aliquot from the remaining 40 µl of RNase-digested bacterial nucleic acid and cleaving it in a buffer composed of 100 mM NaCl, 10 mM Tris-HCl (pH 7.5), 10 mM $MgCl_2$ with approximately 20 units of Pst I for 60 min at 37° C. Again, the restriction enzyme digests were resolved by agarose gel electrophoresis.

The isolated and purified genes encoding the E. acervulina, E. brunetti, E. maxima, E. mitis, E. necatrix, E. braecox and E. tenella small subunit ribosomal RNA are shown in FIGS. 1–7 respectively. The seven gene sequences were compared and regions of nucleotide divergence were identified. Oligonucleotides complimentary to these divergent regions were synthesized as described above and were used as hybridization probes as described below. Table 4 illustrates the primary divergent sequences for the various species of Eimeria, The sequences listed in Table 3 (except for those in the 'common' group) are examples of the most convenient species-specific hybridization probes, i.e. probes which were constructed to regions of the ssrRNA genes containing the maximal diversity of nucleotide sequence, resulting in maximal specificity.

TABLE 3

| Eimeria species | Probe Name | Sequence |
| --- | --- | --- |
| acervulina | WEaRC | CAGCCCACGCAATTAAGCGCAGGAG (SEQ ID NO:6) |
| | PEa4-RC | GAAGTGATACGATAACCGAAGTT (SEQ ID NO:7) |
| | PEa4e-RC | TACGATAACCGAAGTTACCG (SEQ ID NO:35) |
| brunetti | AEb1RC | CCCCTTCATAGAAAGGAAGCC (SEQ ID NO:8) |
| | AEb1aRC | CCCCTTCAAAGAAGGAAGCC (SEQ ID NO:9) |
| | PEb4-RC | TGCGTGACCGAGGTCA (SEQ ID NO:10) |
| | PEb4e-RC | GATACGGTAACCAAAGTCACC (SEQ ID NO:36) |
| maxima | WEmx1RC | CAAGACTCCACAAGAATTGTG (SEQ ID NO:11) |
| | PEmx4-RC | GATACGGTAACCGAGGTCAC (SEQ ID NO:12) |
| | PEmx4a-RC | GATACGGTAACCGAGGTCA (SEQ ID NO:37) |
| mitis | PEmt1RC | CCAGAGGAGGGCCTATGCG (SEQ ID NO:13) |
| | PEmt1aRC | CCAGAGGAGGAGGCCTATGCG (SEQ ID NO:14) |
| | PEmt4-RC | TGACCTGGTGACCCAGG (SEQ ID NO:15) |
| necatrix | WEn-1RC | CGTTAAGTGGGTTGGTTTTG (SEQ ID NO:16) |
| | WEn-1M | CAAAACCAACCCACTTAACG (SEQ ID NO:38) |
| | PEn4-RC | AAGTGATACAGTAATCGTGAAGTT (SEQ ID NO:17) |
| praecox | WEp1RC | CACCATGACTCCACAAAAGTG (SEQ ID NO:18) |

TABLE 3-continued

| Eimeria species | Probe Name | Sequence |
|---|---|---|
| | PEp4-RC | AGAAGTGATACAGTAACCGAAGTT (SEQ ID NO:19) |
| | Pep4d-RC | TGATACAGTAACCGAAGTTACTG (SEQ ID NO:39) |
| tenella | WEt1RC | CCAAGACTCCACTACAAAGTG (SEQ ID NO:20) |
| | PEt4-RC | GTGATACAGTAACCGCAAAGTT (SEQ ID NO:21) |
| | PEt4a-RC | TACAGTAACCGCAAAGTTACTG (SEQ ID NO:40) |
| common | CommonRC | AGCCATTCGCAGTTTCACCG (SEQ ID NO:22) |
| | Common4RC | AAGGTCTCGTTCGTTATCGA (SEQ ID NO:23) |
| | Com4A-RC | GGTCTCGTTCGTTAATCGAA (SEQ ID NO:41) |
| | COM4B-RC | CATCACAGACCTGTTATTGCC (SEQ ID NO:42) |
| | COM4C-RC | CATAGAACGGCCATGCA (SEQ ID NO:43) |

Other regions of the ssrRNA genes which can serve the same purpose are listed in Table 4. An indicator of ssrRNA sequence diversity was obtained by computer analysis of the sequences illustrated in FIGS. 1–7. The program PRETTY within the GCG (Univ. of Wisconsin) program package was used as an example of a multiple sequence alignment program. The objective of the algorithm of this program is to maximize the areas of homology between the sequences compared by making base by base comparisons and inserting gaps which correspond to additions or deletions as necessary to optimize the number of matches. FIG. 12 is an example of the output generated by 'PRETTY' using the sequences illustrated in FIGS. 1–7. Note that there is an additional line of sequence termed 'consensus.' This is a position by position report on the homology of the sequences compared. If all seven nucleotides match, a capital letter is used to identify that event. If a single difference is observed it is denoted by a (—) in the consensus sequence. It should also be noted that in this 'aligned' format, all seven species end up with a sequence length of 1766 bases, do to the insertion of various sized gaps. Thus the nucleotide numbering system in FIG. 12 is relative to the alignment program and program parameters used. Nucleotide segments of interest in the 'aligned' format must be cross referenced to the absolute sequence numbering system for each individual species.

TABLE 4

Regions Of The ssrRNA Gene From Chicken Eimeria Species Useful As Species-Specific Hybridization Probe Targets. Nucleotide Positions Relative To The 'Alignment' In FIG. 12.

| Region | Nucleotide Span |
|---|---|
| 1 | 106–114 |
| 2 | 154–180 |
| 3 | 189–227 |
| 4 | 257–272 |
| 5 | 636–733 |
| 6 | 932–939 |
| 7 | 1037–1052 |
| 8 | 1062–1068 |
| 9 | 1160–1173 |
| 10 | 1341–1392 |
| 11 | 1487–1529 |
| 12 | 1679–1716 |

Areas of the ssrRNA gene from the seven chicken Eimeria species, which have diverged during the course of evolution can be identified by comparing the 'consensus' sequence and in particular locating areas where dashes (—) cluster (see FIG. 12). Using this type of analysis approximately 12 regions within the ssrRNA gene from the chicken Eimeria have been identified which contain sufficient species-to-species nucleotide sequence diversity to be useful hybridization probe targets, i.e. regions which will serve as templates for oligonucleotide hybridization probes. Table 5 lists these regions using the 'aligned' nucleotide numbering system. Table 5 lists the same regions using the absolute sequence numbering system for each species as illustrated in FIGS. 1–7. The following table contains the nucleotide position for each region of Table 4, for each of the Eimeria species.

TABLE 5

| Species: Region, (Nucleotide Span) | |
|---|---|
| E. acervulina: | 1, (106–113); 2 (153–179); 3, (188–215); 4, (254–267); 5, (631–728); 6, (927–934); 7, (1031–1047); 8, (1057–1063); 9, (1155–1168) 10 (1336–1378); 11, (1473–1515); 12, (1665–1700). |
| E. brunetti: | 1, (106–113); 2, (153–179); 3, (188–222); 4, (252–264); 5. (629–726); 6, 925–932); 7, (1030–1045); 8, (1054–1061); 9, (1153–1167); 10, (1334–1375); 11, (1470–1512); 12, (1661–1669). |
| E. maxima: | 1, (106–113); 2, (153–179); 3, (188–226); 4, (256–269); 5, (633–730); 6, (929–936); 7, (1034–1049); 8, (1059–1065); 9, (1157–1170); 10, (1338–1380); 11, (1475–1517); 12, (1667–1702). |
| E. mitis: | 1, (106–113); 2, (153–179); 3, (188–223); 4, (253–266); 5, (630–725); 6, (923–928); 7, (1026–1041); 8, (1051–1057); 9, (1149–1161); 10, (1329–1380); 11, (1474–1517); 12, (1667–1701). |
| E. necatrix: | 1, (106–114); 2, (154–180); 3, (188–226); 4, (255–271); 5, (635–732); 6, (931–938); 7, (1036–1051); 8, (1060–1067); 9, (1159–1172); 10, (1340–1384); 11, (1479–1521); 12, (1671–1708). |
| E. preacox: | 1, (106–113); 2, (153–179); 3, (188–223); 4, (253–266); 5, (630–727); 6, (927–933); 7, (1031–1046); 8, (1056–1062); 9, (1154–1168); 10, (1335–1375); 11, (1471–1514); 12, (1664–1699). |
| E. tenella: | 1, (106–114); 2, (154–180); 3, (189–226); 4, (255–271); 5, (635–732); 6, (931–938); 7, (1036–1047); 8, (1061–1067); 9, (1159–1172); 10, 1340–1384); 11, (1479–1521); 12, (1671–1708). |

EXAMPLE 2

Infectivity Assay

Live coccidiosis vaccine lots were produced using oocysts from attenuated strains of Eimeria. A vaccine was prepared with the following Eimeria species: *E. acervulina, E. tenella, E. maxima, E. necatrix, E. praecox, E. mitis, E. brunetti.* An immunogenic dose of oocysts from each species was combined, beaded in wax and covered with gypsum. One day old female SPF Leghorn chicks were housed in isolator cages and given non-vaccine containing feed and water *ad libitum* until two weeks of age. Feed was removed on the day prior to administration of the vaccine. Vaccine beads were weighed and aliquots equivalent to 0.25X, 0.5X, 1X, 2X, 3X, 5X and 10X vaccine dose were mixed with feed (15 g/chick) and presented to the chicks in groups of 8 to 10 animals. All vaccine was consumed within four hours. After the vaccine was fully consumed, vaccine-free feed was administered for the duration of the test. A group of 8 to 10 untreated birds were fed regular feed and water *ad libitum* for the duration of the experimental regimen. One additional group of 8 to 10 birds was dosed by gavage with the the same number of unencapsulated oocysts (1X) and fed *ad libitum.* These birds represented a positive control for infection and served to check the viability of organisms following encapsulation since the unencapsulated oocysts were from the same production batch as those in the vaccine. Three to five days following administration of the vaccine or unencapsulated oocysts, mucosal and epithelial scrapings were prepared from the intestinal walls of the birds. Total nucleic acids extracted from these scrapings served as the hybridization target or PCR amplification template in this protocol. The relative infectivity of each species of Eimeria subsequent to the encapsulation process was estimated based upon the ability to detect an amplification of the number of input oocysts. This was accomplished using the species-specific $^{32}$P-labeled oligonucleotide hybridization probes described in Example 1. Some of the birds in each treatment group were saved to monitor fecal oocyst counts from days four to seven post-infection. Quantitation was based on a standard curve using genomic DNA prepared from cloned vaccine strain oocysts.

Preparation Of Total Nucleic Acids

Chickens were sacrificed 3–5 days after receiving a vaccine dose. The intestine and the ceca were removed, cut along their length and rinsed with tap water. The interior wall of the intestine and ceca were scraped using a microscope slide. The scrapings were transferred to a 50 ml centrifuge tube and processed immediately. Five to 10 ml of 2X Proteinase K digestion buffer (400 mM Tris-HCl, pH 7.6, 100 mM EDTA, 1.0% SDS) were added to the scrapings and the suspension was mixed vigorously on a vortex mixer. To the suspension was added 200 μl of 5 mg/ml proteinase K and the suspension was allowed to digest at 55° C. for 3 hours. If viscosity was a problem at this point another 5 ml of digestion buffer and another 100 μl of 5 mg/ml proteinase K were added and digestion was continued overnight. Following the overnight digestion, 100 μl of 5 mg/ml proteinase K was added and digestion was continued for up to 3 to 24 hours. Six hundred microliters of the digest was removed and placed into a 1.5 ml microfuge tube and extracted twice with a 1:1 mixture of digestion buffer equilibrated phenol and chloroform. The samples were then extracted with a 24:1 mix of chloroform and isoamyl alcohol. The final aqueous phase was stored at −20° C. An aliquot of the final aqueous phase was ethanol precipitated. In most cases 200 μl of the final aqueous phase was added to 20 μl of 3 M sodium acetate (pH 4.6) and then combined with 500 μl of ethanol. The samples were mixed by inversion and placed in a dry ice ethanol bath for 20 minutes. The genomic DNA was then collected by centrifugation in an Eppendorf microcentrifuge for 15 minutes. The precipitate was washed once with 70% ethanol and dried in a Speed-Vac (Savant). The precipitate was suspended in 200 μl of deionized water. The amount of DNA in the total nucleic acid preparation was estimated using bisbenzimide which is a fluorochrome whose properties change when bound to DNA as mentioned previously. Salmon testes DNA standards ranging from 0 to 20 μg/100 μl in TE were made from a stock solution. Dilutions were prepared in 12×75 mm borosilicate tubes using sterile tips which were changed between dilutions. Similarly, 1:10 dilutions were prepared to a final volume of 100 μl for each experimental sample in duplicate. A bisbenzimide dye stock at a concentration of 200 μg per ml sterile water was prepared and stored at 4° C. in a dark bottle. Prior to use, the dye stock was diluted 1:200 with a buffer whose composition was 50mM sodium phosphate, pH 7.6, 2 M NaCl. Two milliliters of this were added to each borosilicate tube with an Eppendorf repeater pipette, mixed and measured directly in a fluoro-colorimeter at an excitation wavelength of 356 nm and an emission wavelength of 458 nm. The amount of DNA in the experimental samples was determined after calibrating the machine with the appropriate standards as described by the manufacturer.

PCR Amplification Of Protozoan ssrRNA Sequences From Genomic DNA Prepared From Chicken Intestinal Epithelial and Mucosal Scrapings Due to the exquisite sensitivity of this technique, extreme caution was exercised to avoid contamination. Dedicated pipettes, pipette tips, vessels and stock solutions for DNA preparation, reaction assembly and sample analysis were used. Two hundred ng of experimental genomic DNA based upon the bisbenzimide assay above were used as the starting target material. This material was first ethanol precipitated to remove solvents remaining from the extractions which inhibit the Taq DNA polymerase. Genomic DNAs prepared from known numbers of purified organisms from each of the species of Eimeria were used to "spike" 200 ng of chicken hepatic genomic DNA. These served as amplification standards and hybridization specificity standards. A daily working solution of Tris-HCl buffered (pH 7.6) deoxynucleoside triphosphates dATP, dCTP, dGTP and dGTP each at 1.25 mM was prepared from 100 mM stocks stored frozen at −20° C. A 10X reaction buffer composed of 100 mM Tris-HCl, pH8.3, 500 mM KCl, 15 mM MgCl$_2$, 0.01% gelatin was prepared and autoclaved. This was then aliquoted and stored at −20° C. The reaction mix was assembled in dedicated PCR reaction tubes in a final volume of 100 μl. A reaction mix cocktail was prepared by mixing the following components at these final concentrations in this specific order: water, dATP, dCTP, dGTP and dTTP (dNTPs each at 200 μM), 1X reaction buffer, and 1 μM of each of the two amplification primers (ERIB 1 and ERIB 2) (SEQ ID NO:1 and SEQ ID NO:3), then mixed, and 1.25 U Taq DNA polymerase per reaction tube was added and mixed by inversion. An aliquot of 80 µl of the cocktail was then distributed to each reaction tube. Based on the bisbenzimide DNA assay described above, 200 ng of experimental genomic DNA was adjusted to a final volume of 20 µl with distilled water and added to the reaction mixture. The BIOS thermal cycler was programmed as follows:

a) 3 cycles consisting of 94° C. for 1 minute to denature, 50° C. for 30 seconds to anneal and 72° C. for 45 seconds for polymerization;

b) 27 cycles consisting of 94° C. for 20 seconds to denature, 50° C. for 30 seconds to anneal and 72° C. for 45 seconds for polymerization;

c) one cycle at 72° C. for 10 minutes.

When using primer pairs 5AERIB/3AERIB (SEQ ID NO:31/SEQ ID NO:32) or 5BERIB/3BERIB (SEQ ID NO:33/SEQ ID NO:34), a reaction mixture was prepared by mixing the following components at these final concentrations in this specific order: water, dATP, dCTP, dGTP and dTTP (dNTPs each at 200 µM), 1X reaction buffer, and 1 µM of each of the two amplification primers (5AERIB [SEQ ID NO:31]and 3AERIB [SEQ ID NO:32]or 5BERIB [SEQ ID NO:33]and 3BERIB [SEQ ID NO:34), then mixed and 1.25 U Taq DNA polymerase per reaction tube was added and mixed by inversion. An aliquot of 80 µl of the mixture was then distributed to each reaction tube. Based on the bisbenzimide DNA assay described above, 200 ng of experimental genomic DNA was adjusted to a final volume of 20 µl with distilled water and added to the reaction mixture. The reaction was overlayed with approximately 50 µl of light mineral oil and then placed into a Perkin Elmer Cetus DNA thermal cycler programmed as follows:

a) 3 cycles consisting of 94° C. for 1 minute to denature, 48° C. for 1 minute to anneal and 72° C. for 1 minute for polymerization;

b) 32 cycles consisting of 94° C. for 1 minute to denature, 50° C. for 1 minute 30 seconds to anneal and 72° C. for 2 minutes for polymerization;

c) one cycle at 72° C. for 10 minutes. Five µl of the reaction product were then assayed for DNA content using a small scale bisbenzimide assay analogous to that described above. The small scale assay used dilutions in microcentrifuge tubes in duplicate, with a final assay volume of 500 µl. The samples were read in a microcell and the standard curve was linear from 5 to 200 ng/ml.

Immobilization Of Nucleic Acids On A Nylon Support In A Slot-blot Or Dot-blot Manifold Generally, 100 ng of PCR product as quantitated above was adjusted to 100 µl with water and applied to Nytran sheets (prewetted in water) in a slot-blot or dot-blot manifold as per the manufacturer's specifications (Schleicher and Schuell, Inc.). To each sample was added 1 volume of 1 M NaOH. The samples were then incubated at room temperature for 5 minutes to denature the DNA and subsequently neutralized by adding 1 volume of 1 M Tris-HCl (pH 7.3). A vacuum was then applied to the apparatus to filter the samples. Each sample was then rinsed with 500 µl of 4 M ammonium acetate (pH 6.8). Genomic DNA prepared from purified organisms representing each of the species of chicked Eimeria and subjected to PCR as described previously was used to "spike" chicken hepatic genomic DNA also subjected to PCR as described previously. The spiked DNA was applied to the filters and served as a species-specific quantitation standard. Appropriate buffer controls and blank slot controls were routinely included. The filters were air dried and baked under vacuum at 80° C. for 2 hours (optional).

Oligonucleotide hybridization probes (from Example 1) were end labeled with gamma $^{32}$P-ATP. The oligonucleotides were quantitated and standardized using the the following formula (1 mg/ml=25 $A_{260}$). Five to ten picomoles of oligonucleotide were added to a 50 µl reaction volume containing water, 5 µl of 10X kinase buffer (0.5 Tris-HCl, pH 7.6, 0.1 M MgCl$_2$, 50 mM DTT, 1 mM spermidine, 1 mM EDTA), 20U of polynucleotide kinase, and at least two fold molar excess of gamma $^{32}$P-ATP (specific activity>5000 Ci/mmol). The mixture was incubated for 30 minutes at 37° C. and then stopped by the addition of 4 µl of 0.5 M EDTA, 46 µl of TE. The reaction mixture was extracted once with a 1:1 mixture of buffer equilibrated phenol and chloroform and the aqueous phase was passed through a Stratagene push column (Stratagene) as per the manufacturer's specifications to remove the unincorporated isotope from the labeled oligonucleotide.

Prehybridization, Hydridization And Washes

Prehybridization was carried out in a buffer whose composition was 6X SSPE, 1% SDS, 10X Denhardt's, 100 µg per ml tRNA. The buffer was made and kept at 42° C. until ready for use to keep the SDS in solution. The dry sheet(s) of Nytran were prewetted in 6X SSPE, placed in a polyethylene freezer bag which was heat sealed on three sides. The prehybridization solution (20–40 ml depending on the number of sheets of Nytran in the bag) was added and the bag was sealed on the fourth edge after removing the bulk of the air bubbles, secured to a glass plate with elastic bands and submerged in a water bath at 42° C. for at least 3 hours or for as long as overnight. Following prehybridization the bag was cut open and the buffer was removed completely. The hybridization buffer was 6X SSPE plus 1% SDS. Hybridization was done at the $T_h$ of the desired hybrid. For probes less than 25 nucleotides in length, hybridization conditions were determined using the following formula:

$$T_h = T_m - 5° C. = 2° C.(A\text{-}T\ bp) + 4° C.(G\text{-}C\ bp) - 5° C.$$

The end labeled oligonucleotide probe was warmed at 68° C. for 5 min prior to mixing with 10–20 ml (depending on the number of filters per bag; approx. 1–5×10$^6$ dpm/ml) of hybridization buffer which was prewarmed at the $T_h$. This was poured into the bag, air bubbles were removed and the bag was resealed. The bag was secured to a glass plate and submerged in a water bath at the $T_h$ for at least 12 hours to overnight for hybridization. Following hybridization, the bag was cut open and the buffer was discarded. The remaining three sides of the bag were cut and the filters were removed with forceps to a pyrex dish containing the first wash solution. The washes were as follows:

a) 3 times for 5–10 minutes each in 6X SSPE, 1% SDS at 37° C. with shaking;

b) 1 time for 3 rain in 1X SSPE, 1% SDS at the $T_h$ of the hybrid;

c) 3–4 times for approx. 5 rain each in 6X SSPE at room temperature with shaking to remove the SDS. Wash volumes were at least 100 ml; more with multiple filters. All wash solutions were prewarmed at the respective temperatures prior to use. The filters were air dried, placed in a cassette, which contained two intensifying screens, and exposed to X-ray film at −70° C. The film was developed after 1-3 days. Quantitation of hybridization signal was carried out using the Molecular Dynamics PhosphorImager (Molecular Dynamics). Dried blots were placed beneath plastic wrap in the PhosphorImager cassette as per the manufacturer's instructions and exposed to the phosphor for approximately 2 hours for the common hybridization probe and 3-12 hours for the specific Eimeria probes. The screen was then scanned with a laser which releases the energy captured by the phosphor in the screen. The released energy was quantitated by the machine.

EXAMPLE

Use Of Specific Eimeria Species Small Subunit Ribosomal RNA Probes And Assay

Purified oocysts from multiple strains of each of the seven species of chicken Eimeria were prepared as described in Example 1. Sporocysts were purified after disruption of the oocyst shell. Genomic DNA was prepared from each population of sporocysts and quantitated using the bisbenzimide assay. Four micrograms of each preparation of genomic DNA were denatured and immobilized on a Nytran membrane in eight equivalent 0.5 ug aliquots. Gloves were worn and forceps used whenever handling Nytran. Generally about 0.5 µg of genomic DNA was adjusted to about 100 µl (4 µg/800 µl) and added to 0.1 volume of 3 M NaOH. This was incubated at about 70° C. for about 30 to 60 minutes to denature the DNA, cooled to room temperature, neutralized by adding about one volume of 2 M ammonium acetate (pH 7.0)) and applied to Nytran sheets in a slot-blot or dot-blot manifold as described by the manufacturer (Schleicher and Schuell, Inc). Vacuum was applied to the apparatus to filter the samples. Appropriate buffer controls and blank slot controls were routinely included. The filters were air dried and baked under vacuum at about 80° C. for about 2 hours. Chicken genomic DNA (Clonetech Laboratories, Inc.) was similarly denatured and immobilized. The eight filters were prehybridized in individual bags and then hybridized with the respective species-specific probes (X7) and a probe common to all eukaryotic ssrRNA gene sequences. The common probe used was 'common RC' with the following sequence: AGCCATTCGCAGTTT-CACCG (SEQ ID NO:22). The common probe was derived from highly conserved sequence segments. This is only an example of one of many such probes which could be made for conserved sequences within the ssrRNA gene. It is understood that only those sequences which are spanned by the particular PCR primer pair are useful as probes for that target. These probes could be used to normalize the signal across broad phylogenetic groups (i.e. Eimeria and Gallus). FIG. 8 shows the results generated using the E.tenella specific probe (WEtlRC) (SEQ ID NO:20). Only those slots in the grid containing E.tenella genomic DNA gave positive hybridization signals or response with WEtlRC. The DNA in these slots was derived from a field isolate, a laboratory strain, a precocious isolate (the vaccine strain) and a clonal derivative of the vaccine strain. Each of the four gave roughly equivalent hybridization signals. This indicates that the hybridization probe is species-specific, but not specific for the vaccine strain.

Similar types of experiments designed to verify the species-specific hybridization characteristics for the remaining six Eimeria probes were conducted and the results from three of these are depicted in FIG. 9. Probes derived from the ssrRNA genes of E. pracecox (WEplRC) (SEQ ID NO:18), E. maxima (WEmxlRC) (SEQ ID NO:11) and E. necatrix (WEn-1M) (SEQ ID NO;38) (from Example 2) are indeed species-specific. As is the case with each of the Eimeria probes, hybridization to both nonprecocious laboratory isolates and vaccine strains is roughly equivalent.

Hybridization of the eighth replicate filter with the probe derived from ssrRNA gene nucleotide sequence common to eukaryotes (common RC, SEQ ID NO:22) indicated that an equivalent amount of "hybridizable" genomic DNA was immobilized in each of the labeled grids.

Figure 10:
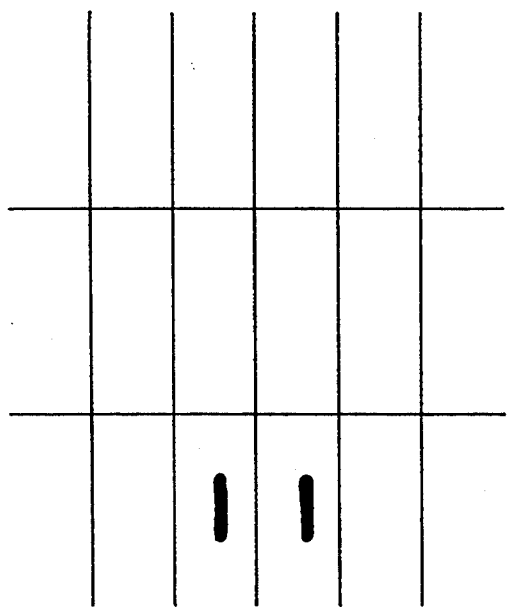
FIG. 10. Species-specific detection of Eimeria in the intestinal mucosa of infected chickens.

Groups of two chickens were each dosed by gavage with 2,500 purified oocysts of a single species of chicken Eimeria. An additional pair of birds did not receive any oocysts. Five days later the birds were sacrificed, the intestinal epithelia and mucosa was scraped and genomic DNA was prepared from this tissue. The resulting DNA was quantitated and 200 ng were allquoted for use as a reaction substrate in the polymerase chain reaction (PCR) along with the PCR amplification primers ERIB 1 (SEQ ID NO:1) and ERIB 2 (SEQ ID NO:3). Ten percent of the reaction product was then denatured and immobilized on eight identical slot blot grids. FIG. 10 shows the results from hybridization of one of these panels with the E.brunetti specific probe (AEblRC) (SEQ ID NO:8). Only those birds dosed with E.brunetti oocysts gave a positive hybridization signal with this probe. These and similar results with the other hybridization probes not only reconfirmed the species-specific nature of the respective hybridization probes but, also and more importantly, indicated a high sensitivity for the detection of an infection stemming from 2500 oocysts.

Figure 11:
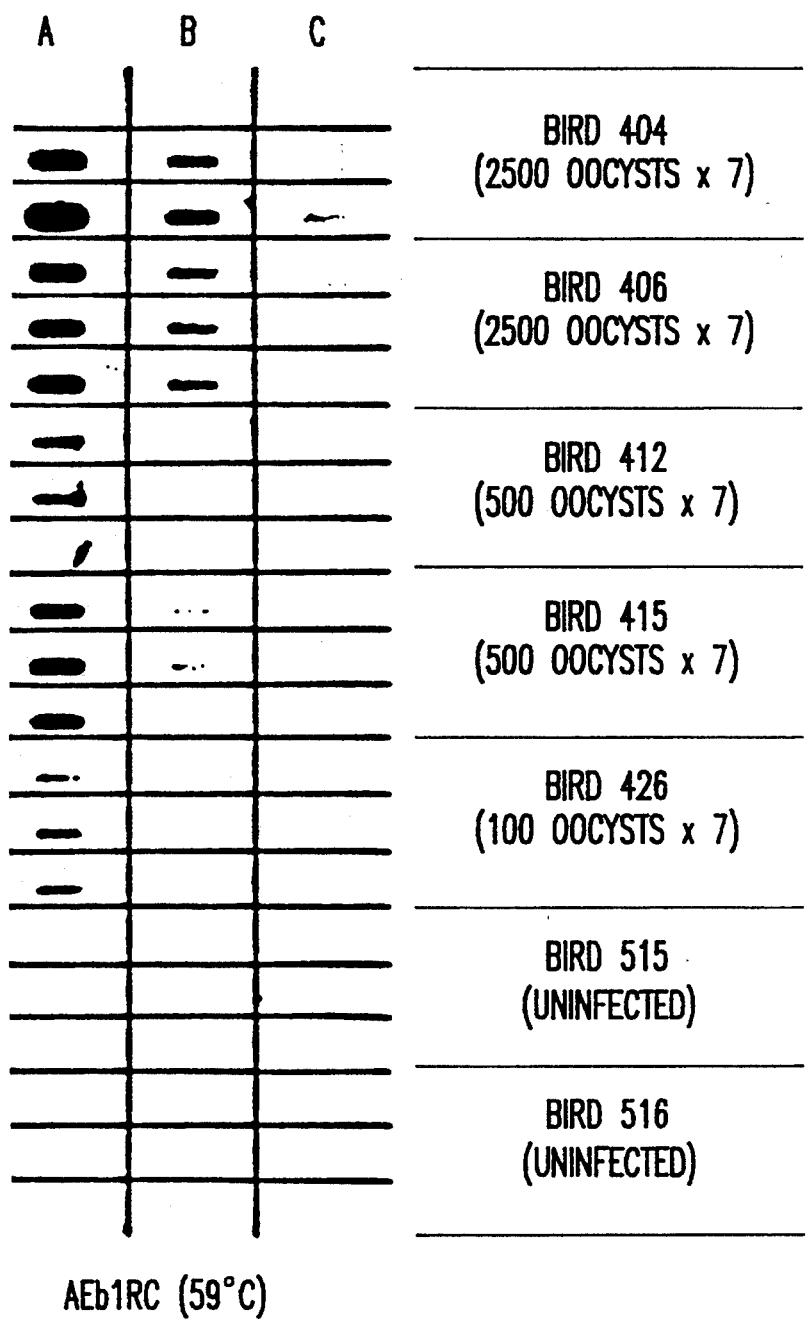
FIG. 11. Species-specific detection of Eimeria in the intestinal mucosa of heptavalent infected chickens.

The vaccine dose however was considerably fewer than 2500 oocysts and was composed of all seven species of chicken Eimeria. In the next experiment an equal number of oocysts from all seven species were mixed together and birds were dosed by gavage with a titration of this heptavalent mixture. The range of the dose titration was from 100 oocysts of each of the seven species to 2500 oocysts of each of the seven species. Five days following infection intestinal epithelia and mucosa was scraped and genomic DNA was extracted and quantitated (as described in Example 2). Two hundred nanograms of each sample were used as reaction substrates in the PCR using the ERIB 1 (SEQ ID NO:1) and ERIB 2 (SEQ ID NO:3) amplification primers. The reactions were done in triplicate and the products from these individual reactions were immobilized in successive rows in the slot blot manifold as is indicated in the right hand margin of FIG. 11. In addition, 10 µl (10%), 1 µl (1%) and 0.1 µl (0.1%) of each reaction product was loaded in columns A, B and C respectively. Seven identical filters were prepared and each was hybridized with one of the species-specific probes. Results using the E. brunetti specific probe (AEblRC) (SEQ ID NO:8) are shown in FIG. 11. Importantly, an unequivocal hybridization signal was detected in bird 426 which received a dose of 100 oocysts of each species. This result indicates that the PCR/hybridization assay is sensitive enough to detect an infection in the intestine of a chicken that had received a 1X vaccine dose (100 oocysts for E.brunetti). Similar results were obtained with probes specific for the remaining six species.

FIG. 11 also serves to illustrate that triplicate polymerase chain reactions do not result in equivalent amounts of reaction products, despite starting with an equivalent amount of the same reaction substrate. This observation has led us to incorporate two standardization steps into the assay protocol. First, the products resulting from the PCR are quantitated in a small scale bisbenzimide assay which consumes only 5% of the reaction. Using this result, 800 ng of product were denatured and immobilized onto Nytran paper in eight equivalent aliquots of 100 ng each. The eighth replicate filter was routinely hybridized with the common probe (common RC) (SEQ ID NO:22) to confirm that an equivalent amount of denatured and immobilized hybridization target was present in each experimental slot on the filter.

EXAMPLE 4

Assay Method For Detecting Eimeria Ribosomal RNA With Species-Specific Oligonucleotides Isolation of Eimeria RNA from chicken intestines was carded out with care to avoid degradation of the RNA. The protocol is essentially the same as published in Chirgwin et al., Biochemistry 18:5294–5299 (1979). Chickens were orally infected with oocysts fom laboratory strains of *E. acervulina. E. brunetti. E. maxima. E.mitis. E. necatrix. E. praecox* and *E. tenella.* Five days later the chickens were sacrificed. Their intestines and ceca were taken out, cut along their length, and rinsed throughly with running tap water. The interior walls of the intestines and ceca were scraped with a sterile microscope slide. The mucosal scrapings from each chicken were taken and transferred to a 50 ml centrifuge tube. These scrapings were immediately placed into 24 ml of about 4 M guanidine thiocyanate, pH 7.0, 0.5% sodium N-lauroylsarcosine, 25 mM sodium citrate, 0.1 M 2-mercaptoethanol, and 0.1% Sigma 30% Antifoam A. The samples were quickly homogenized with a Polytron (Brinkmann) at full speed three times for 20 seconds; between samples the Polytron was rinsed 2 times with sterile distilled water. The samples were then centrifuged at approximately 8000 RPM for 10 minutes at about 10° C. in a swinging bucket rotor (JS-13, Beckman). The supernatant fluids were decanted and precipitated with 0.6 ml of I M acetic acid and 18 ml of 100% ethanol at −20° C., overnight. The next day the samples were centrifuged again at 8000 RPM for 10 minutes at 10° C. The pellets were resuspended in 12 ml of 7.5 M guanidine hydrochloride, pH 7.0, 25 mM sodium citrate, and 5 mM dithiothreitol, shaken vigorously, and heated to 68° C. until dissolved. The samples were precipitated with 0.3 ml of 1 M acetic acid and 6 ml of 100% ethanol at −20° C., overnight. Again the samples were centrifuged, resuspended, and precipitated overnight at −20° C. as before, except with one-half the previous volumes, i.e. 6 ml, 0.15 ml, and 3 ml respectively. The samples were pelleted once again, triturated with about 10 ml of room-temperature 95% ethanol, transferred to baked Corex centrifuge tubes, and repelleted at 10,000 RPM for 30 minutes at about 10° C. The RNA pellets were dried under vacuum in a Speed-Vac (Savant Instruments), dissolved at 68 ° C in 2 ml diethyl pyrocarbonate-treated sterile distilled water, repelleted, re-extracted with about 1 ml diethyl pyrocarbonate-treated sterile distilled water, and repelleted again. The extractions were reprecipitated with 300 µl of 2 M potassium acetate, pH 5.0, and 8 ml of 100% ethanol at −20° C. overnight. The final RNA was pelleted and resuspended in 1 ml of diethyl pyrocarbonate-treated sterile water. Absorbance readings at 260 nm and 280 nm (Beckman spectrophotometer) were taken to determine RNA concentrations; about 3 µg of RNA was then subjected to electrophoresis on a 1.2% agarose gel to check the RNA quality, size, and relative concentration. RNA samples were stored at −70° C. One milligram of RNA was subjected to DNase-1 digestion using RQ1 DNase (Promega) for 40 minutes at 37° C. as per the manufacturer's specifications and then precipitated with 1/10th volume of 3M NaOAc and 2.5 volumes of 100% ethanol. Duplicate samples containing twenty micrograms of RNA were denatured in 100 µ 1 of 1 X denaturation solution (four times denaturation solution contained 1 ml of formaldehyde, 56 µl of 1 M sodium phosphate, pH 6.5, and 344 µl of sterile distilled water.) at 68° C. for 20 minutes. The denatured samples were then placed on ice to cool. The denatured RNA samples were dotted in duplicate using a Bio-Rad dot-blot apparatus, Nytran filters (S & S), and 10X SSPE. The filters were dried for one hour in an 80° C. oven. The filters were probed with $^{32}$P-labelled oligos as in example 2. The filters were prehybridized and hybridized as per the manufacturer's specifications (Schleicher & Schull) for RNA hybridizations using oligonucleotide probes and using a $T_h$ as specified for each oligo as previously described. The results are shown in FIGS. 13 and 14.

Figure 13:
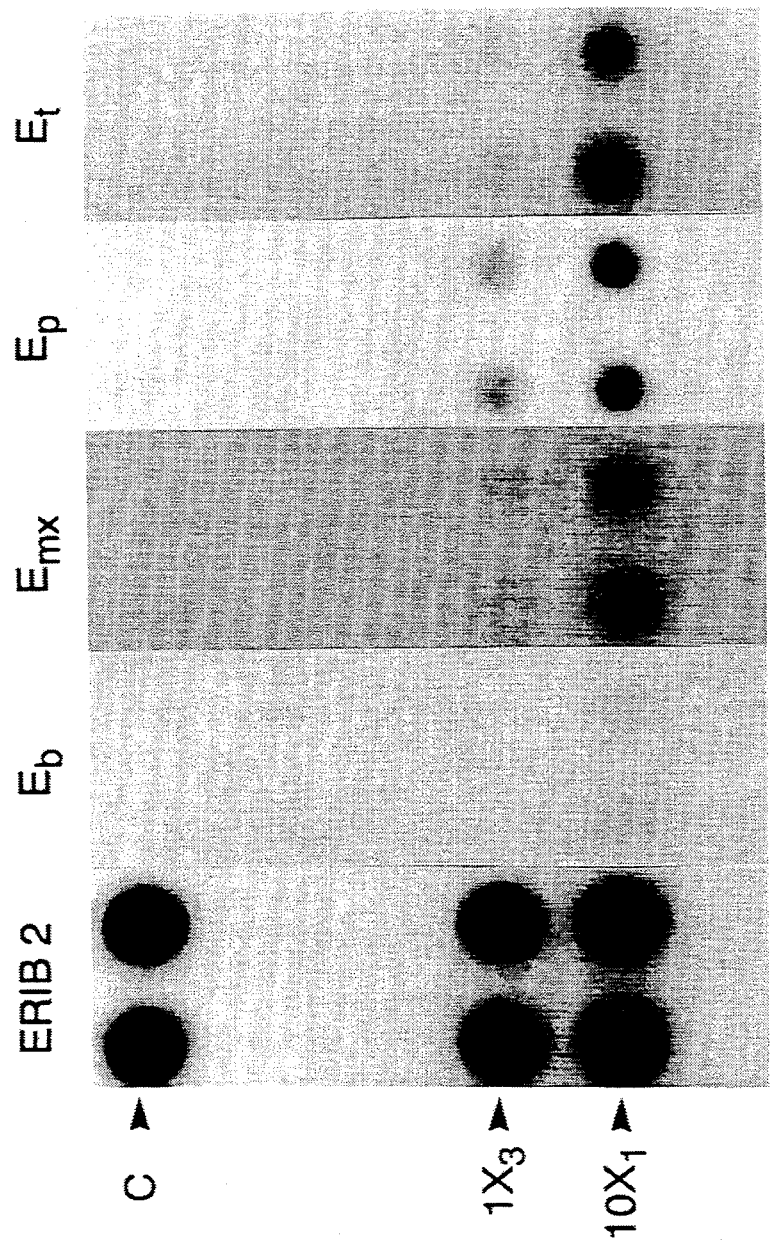
FIG. 13. DNA dot blot analysis using total RNA and species-specific oligonucleotide probes.

FIG. 13 is a composite of five Nytran filters (Schleicher & Schull) on which approximately 30 µg of DNase 1 digested total cellular RNA was spotted. The RNA was derived from duplicate chickens given a heptavalent mixture of oocysts. The filters were processed as described above. The row labeled 'C' was an uninfected chicken control. The rows labeled 'IX' and 'lOX' represented the vaccine dosage used while the adjacent rows represent duplicate samples. The panel labeled 'ERIB2' was a control panel to establish equal loading. It was probed with the Erib2 oligonucleotide (SEQ ID NO 3) the sequence of which is derived from a highly conserved region of the ssrRNA genes and which hybridized to both the infected and uninfected controls. The panel labeled 'Eb' was probed with the oligonucleotide AEbIRC (SEQ ID NO: 8) and at the lOX dose a faint *E. brunetti* signal was seen. The panel labeled 'Emx' was probed with WEmxlRC (SEQ ID NO: 11). A faint *E. maxima* signal was seen at lX and clearly seen at the lOX dose. The panel labeled 'Ep" was probed with WEplRC (SEQ ID NO: 18) and *E. praecox* was demonstrated in both the lX and lOX doses. The panel labeled 'Et' was probed with WEtlRC (SEQ ID NO:20) and a faint *E. tenella* signal was seen at the lX dose, while the lOX dose is clearly seen.

Figure 14:
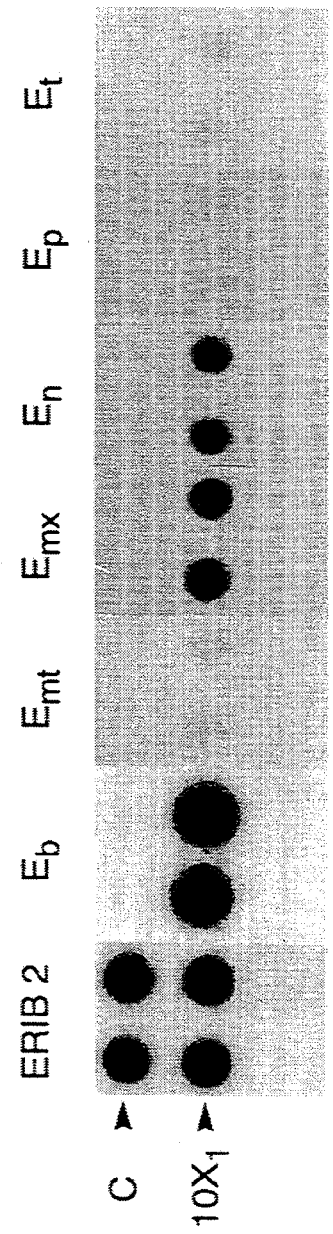
FIG. 14. DNA dot blot analysis using total RNA and species-specific oligonucleotide probes.

FIG. 14 is similar to FIG. 13 except that only the lOX dose was used and different oligonucleotides were used as hybridization probes. The panel labeled 'ERIB2' was probed with the oligonucleotide Erib2 (SEQ ID NO 3) and it hybridized to both infected and uninfected controls with equal intensity. The panel labeled 'Eb' was probed with the oligonucleotide PEb4e-RC (SEQ ID NO: 36) and an *E. brunetti* signal was clearly observed. The panel labeled 'Emt' was probed with PEmt4-RC (SEQ ID NO: 15) and *E. mitis* was detectable at this level. The panel labeled 'Emx' was probed with PEmx-4a-RC (SEQ ID NO: 37) and an *E. maxima* signal was seen. The panel labeled 'En' was probed with the oligonucleotide PEn4-RC (SEQ ID NO: 17) and an *E. neca-*

*trix* signal was observed. The panel labeled 'Ep' was probed with PEp4d-RC (SEQ ID NO: 39) and a faint *E. pnraecox* signal was detected. The panel labeled 'Et' was probed with PEt4a-RC (SEQ ID NO: 40) and an *E. tenella* signal was observed.

EXAMPLE 5

A METHOD FOR DESIGNING SPECIES SPECIFIC OLIGONUCLEOTIDE HYBRIDIZATION PROBES

Once the ssrRNA sequences from all seven avian Eimeria were determined and aligned nonconserved regions were identified. The sequences within the non-conserved regions were analyzed to determine if there were sufficient differences to allow the construction of species specific oligonucleotide hybridization probes. There were three constraints which we placed on the design of our hybridization probes. One was that the probes be species specific. Due to the nature of the assay cross hybridization could not be tolerated. The second was to have a set of oligonucleotide hybridization probes which had melting temperatures ($T_m$) which were as close as possible to a single temperature so as to allow the use of a single hybridization temperature. This constraint was more a matter of convenience than necessity. The last constraint was to make the oligonucleotides the reverse compliment of the sense strand, so the the probes could be used for probing either DNA or RNA. Starting with the sequence for the nonconserved region an oligonucleotide was found which had a $T_m$ of approximately 60° C. The probe was synthesized and tested for specificity.

The target DNA for these specificity studies was obtained in the following manner. Genomic DNA from each of the seven Eimeria species was used as DNA template in the PCR using two amplification primers 5ERIB (SEQ ID NO: 4) and 3ERIB (SEQ ID NO: 5). The use of this particular primer pair is important since they would not produce an amplification product when the DNA temple was derived from either chicken or *E. coli*, i.e. the primer pair is specific for Eimeria ssrRNA genes. This primer pair flanks the nonconserved region to which the oligonucleotide hybridization probes were designed. The reactions were run in the Perkin-Elmer Cetus DNA thermal cycler. The reactions contained about 25 ng of Eimeria genomic DNA and were set up as previously described for this machine. The Perkin-Elmer Cetus DNA thermal cycler was programmed as follows:

a.) about 35 cycles Consisting of 940 C for about I minute to denature, about 50° C. for about 1.5 minutes to anneal and about 72° C. for about 2 minutes for polymerization.

b) about one cycle at about72° C. for about 10 minutes. About 5 ml of the reaction mixture is then assayed for DNA content using the small scale bisbenzimide assay. About 5 ml of the reaction mixture is electrophoresed on an about 2% agarose gel to ensure that the reaction produced a single amplification product. About 10 ng of the PCR product was adjusted to a final volume of about 100 μl with water, and applied to Nytran sheets (prewetted in water) in a slot-blot manifold as described in the manufacturer's specifications (Schleicher and Schuell, Inc.). To each sample was added about 1 volume of 1 M NaOH. The samples were then incubated at about room temperature for about 5 minutes to denature the DNA and were neutralized by adding about 1 volume of 1 M Tris-HCl (pH 7.3). A vacuum was then applied to the apparatus to filter the samples. Each sample was then rinsed with about 500 ml of 4M ammonium acetate (pH 6.8). Appropriate buffer controls and blank controls were included. The Nytran sheets were air dried then baked under vacuum at about 80° C. for about 2 or more hours. The test probe was labelled for hybridization. The preferred method was to end label the test oligonucleotides with gamma $^{32}$P-ATP by methods which have been previously described. Prehybridizations, hybridizations and washes were also carried out as previously described (pages 33-34) Since specificity was the major issue being addressed, a probe was considered species-specific when only the slot containing the targeted species DNA yielded signal. If any other slot gave a signal the probe was not species-specific and not useful in this context.

Figure 15:
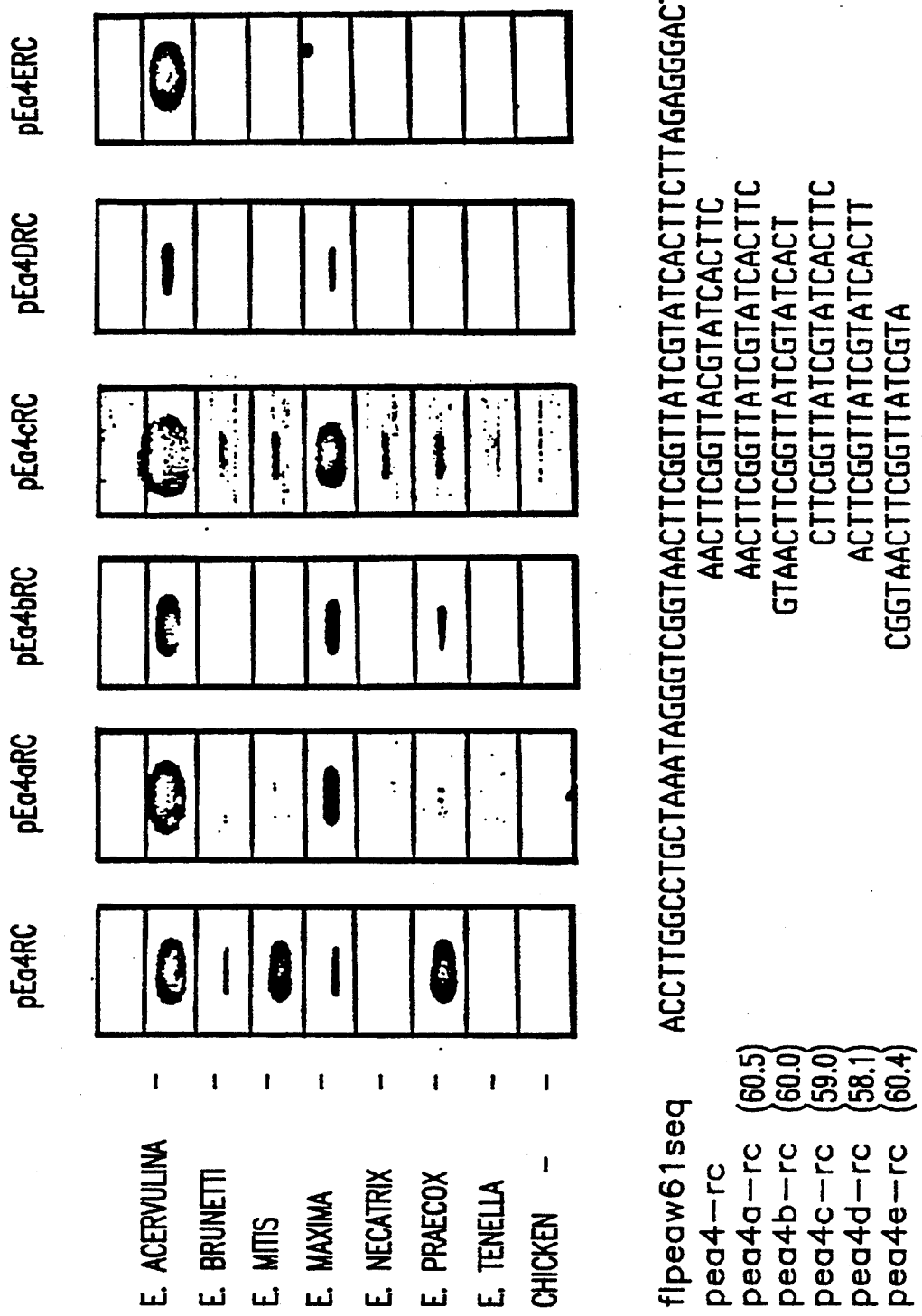
FIG. 15. Design of species-specific oligonucleotide probes.

FIG. 15 illustrates the development of a species-specific hybridization probe for *E. acervulina* in region 10. The first oligonucleotide synthesized was pEa4-RC (SEQ. ID NO: 7) which hybridized with the *E. acervulina* target as well as *E. bruneti*. *E. mitis*. *E. maxima* and *E. praecox*. Further analysis revealed that a single base had been omitted (a T at position #12) so this probe was resynthesized to yield pEa4a-RC (SEQ. ID. NO: 46), which hybridized to the target *E. acervulina* as well as *E. maxima* A dramatic improvement in the species-specificity was obtained by the addition of one base, however, some cross-hybridization did occur. The next oligonucleotide tested was pEa4b-RC (SEQ. ID. NO: 47) which not only hybridized to the target *E. acervulina* but also *E. maxima* and *E. praecox* as well. Oligonucleotide pEa4c-RC (SEQ. ID. NO: 48) was synthesized and tested and found to be as good as pEa4a-RC. (SEQ. ID. NO: 46) When pEa4d-RC (SEQ. ID. NO: 49) was synthesized and tested it also was found to be as good as pEa4a-RC (SEQ. ID. NO: 46). Species-specificity was finally demonstrated when oligonucleotide pEa4e-RC (SEQ. ID. NO: 5) was synthesized and tested. A similar approach was used to develop species specific hybridization probes for the other six chicken Eimeria species.

EXAMPLE 6

Direct Hybridization to Genomic DNA Prepared from Fecal Oocysts as a Method for Parasite Detection and Quantitation Fecal oocysts from birds infected with a monovalent or a mixed inoculum of Eimeria oocysts were collected. Oocysts were purified from fecal material. Sporocysts were isolated and purified from sporulated oocysts. Methods for collection, purification and sporulation of oocysts, and subsequent purification of sporocysts have been described in Example 1. The number of sporocysts in each monovalent collection sample were counted either by Coulter counter or haemocytometer. Genomic DNA was prepared from a known number of each monovalent population of sporocysts as well as from the mixed population of sporecysts from the heptavalent infected groups of birds. The isolation of genomic DNA from sporocysts is described in Example 1. Methods for denaturation and immobilization of genomic DNA on nylon membranes for hybridization are described in Example 3.

Panels I and II in FIG. 16 illustrate typical results which demonstrate the feasibility of this particular method. The two panels are identically loaded and the order of loading is indicated by the text between the panels. Genomic DNA prepared from fecal oocysts of monovalent infected birds is immobilized in rows one through thirteen. A titration of sporocyst equivalents of this genomic DNA from each species is loaded in columns A, B and C. However, the absolute number of sporocyst equivalents differs among the species. For example, there are $1.24 \times 10^6$ E. maxima sporocyst equivalents in slots 7A, but only $1.0 \times 10^6$ E. tenella sporocyst equvalents in slots 11A. Slots 15A, B and C contain a titration of chicken genomic DNA and are included to serve as a negative hybridization control. Slots 17A, 17B, 17C and 18A contain 10% of the genomic DNA prepared from an unknown number of sporocysts purified from four separate heptavalent experimental infections.

Filters I and II were prehybridized in individual bags and then hybridized with the E. maxima (WEmxlRC, SEQ ID NO:11) and the E. tenella (WEtlRC, SEQ ID NO:20) species specific probes, respectively. In panel I hybridization specificity is demonstrated by the observation that only row 7, which contains the E. maxima DNA target, shows a significant signal. Moreover, the signal intensity decreases from slot 7A to 7B to 7C which correlates with the titration of immobilized target DNA in these slots. Only one of the four experimental slots (number 19A) containing genomic DNA from heptavalent infected birds hybridized with the E. maxima probe. The intensity of the signal corresponds to the intensity seen with the signal in slot 7C, or roughly $0.3 \times 10^6$ sporocyst equivalents. Since 10% of the entire experimental sample was loaded in slot 19A, we estimate that the total number of E. maxima sporocysts in the mixed sporocyst population was on the order of $3 \times 10^6$. The lack of hybridization to DNA immobilized in slots 17A, 17B and 17C suggests that these experimental samples contain less than $1 \times 10^6$ E. maxima sporocyst equivalents.

Hybridization specificity with the E. tenella probe is demonstrated in panel II by the fact that only one of the seven monovalent infected experimental samples (row 11) generates a positive signal. The hybridization signal titrates in a manner which correlates with the relative mount of E. tenella sporocyst genomic DNA equivalents immobilized in slots 11A, 11B and 11C. The approximate number of sporocyst equivalents is indicated by the numbers over these slots. Two of the four experimental slots (numbers 17C and 19A) that contain genomic DNA from heptavalent infected birds hybridized with the E. tenella probe. By comparison to the hybridization signals in row 11, we estimate that slots 17C and 19A contain $<0.25 \times 10^6$ and $0.5 \times 10^6$ sporocyst equivalents, respectively. Since these slots contain 10% of the total genomic DNA prepared from the experimental samples, the total number of E. tenella sporocysts in the mixed sporocyst population was on the order of $<2.5 \times 10^6$ and $5 \times 10^6$, respectively. By analogy, heptavalent infected experimental samples corresponding to slots 17A and 17B appear to contain less than $1 \times 10^6$ E. tenella sporocyst equivalents.

---

What is claimed is:

1. A DNA probe, the DNA probe being selected from the group consisting of 5' CACCATGACTCCACAAAAGTG 3' (SEQ ID NO: 18) and 5' TGATACAGTAACCGAAGTTACTG 3' (SEQ ID NO: 39).

2. A DNA probe consisting of composition, consisting essentially of 5' CACCATGACTCCACAAAAGTG 3' (SEQ ID NO: 18), 5' TGATACAGTAACCGAAGTTACTG 3' (SEQ ID NO: 39), and mixtures thereof.

* * * * *